United States Patent
Ho et al.

(10) Patent No.: US 7,084,154 B2
(45) Date of Patent: Aug. 1, 2006

(54) 2-(AMINOMETHYL) ARYLAMIDE ANALGESICS

(75) Inventors: Koc-Kan Ho, West Windsor, NJ (US); John J. Baldwin, Gwynedd Valley, PA (US); Adolph C. Bohnstedt, Burlington, NJ (US); Steven G. Kultgen, Dayton, NJ (US); Edward McDonald, Surrey (GB); Tao Guo, Dayton, NJ (US); John Richard Morphy, Stirling (GB); Zoran Rankovic, Airdrie (GB); Robert Horlick, San Diego, CA (US); Kenneth C. Appell, Skillman, NJ (US)

(73) Assignee: Pharmacopeia Drug Disclovery, Inc., Cranbury, NJ (US)

( * ) Notice: Subject to any disclaimer, the term of this patent is extended or adjusted under 35 U.S.C. 154(b) by 248 days.

(21) Appl. No.: 10/364,039

(22) Filed: Feb. 11, 2003

(65) Prior Publication Data

US 2004/0167119 A1 Aug. 26, 2004

(51) Int. Cl.
*A61P 25/00* (2006.01)
*A61K 31/44* (2006.01)
*C07D 471/02* (2006.01)
(52) U.S. Cl. .................... 514/292; 546/86; 546/87
(58) Field of Classification Search ........... 514/292; 546/86, 87
See application file for complete search history.

(56) References Cited

FOREIGN PATENT DOCUMENTS

| CA | 2328720 | 4/1999 |
|----|---------|--------|
| WO | WO/2001/054694 | 8/2001 |

OTHER PUBLICATIONS

Isaac, Methvin et al., "5,5-Diaryl-2-amino-4-pentenoates as Novel, Potent, and Selective Glycine Transporter Type-2 Reuptake Inhibitors" Bioorganic and Medicinal Chemistry Letters, vol. 11, 2001, pp. 1371-1373.

Caulfield Wilson L. et al., "The First Potent and Selective Inhibitors of the Glycine Transporter Type 2", Journal of Medicinal Chemistry, American Chemical Society, Washington D.C., vol. 44, No. 17, Aug. 16, 2001, pp. 2679-2682.

Ho, Koc-Kan et al., "2-(Aminomethyl)-benzamide-based glycine transporter type-2 inhibitors", Bioorganic and Medicinal Chemistry Letters, vol. 14, 2004, pp. 545-548.

*Primary Examiner*—Brenda Coleman
(74) *Attorney, Agent, or Firm*—Heslin Rothenberg Farley & Mesiti, P.C.; Philip E. Hansen

(57) ABSTRACT

A chemical genus of 2-(aminomethyl)arylamides, which are useful as analgesics, is disclosed. The genus is represented by the formula I:

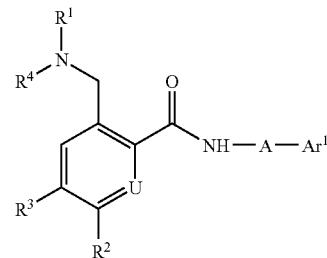

A representative example is:

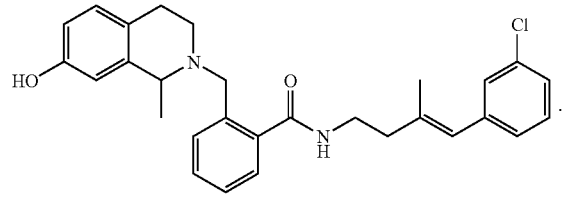

14 Claims, No Drawings

2-(AMINOMETHYL) ARYLAMIDE ANALGESICS

FIELD OF THE INVENTION

The present invention relates to a chemical genus of 2-(aminomethyl)arylamides which are useful as analgesics.

BACKGROUND OF THE INVENTION

Neurotransmitters are chemicals existing in the body, which execute the transfer of signals between neurons and target cells. After a neurotransmitter is released from a nerve terminal, it is actively transported back to the presynaptic nerve terminal by a specific reuptake transporter system. This reuptake mechanism controls the precise concentration and duration of neurotransmitter present in the synaptic space, and in turn controls the extent of stimulation of the target cell (for review, see *Mol. Endo.* 1993, 7, 1517–1529).

The amino acid glycine is a major neurotransmitter within the central nervous system (CNS) of vertebrates, functioning at both inhibitory and excitatory synapses. The synaptic levels of glycine are controlled by high affinity uptake systems (transporters) and two such transporters, $GlyT_1$ (*Neuron* 1992, 8, 927–935) and $GlyT_2$ (*FEBS Lett.* 1998, 439, 334–340), have recently been cloned.

The $GlyT_1$ transporter is closely associated with the excitatory system in which glycine and/or D-serine acts as a co-agonist for the glutamate receptors (*Nature* 1987, 325, 529–531). The $GlyT_2$ transporter is closely associated with the inhibitory system mediated through the strychnine-sensitive glycine receptor (ssGlyR) and is assumed to control the level of glycine in the synaptic space associated with this receptor (*J. Neurochem.* 1995, 65, 2800–2803). This inhibitory system is almost entirely confined to the spinal cord and hindbrain, where it participates in a variety of motor and sensory functions.

Selective inhibitors of the Glycine-$T_2$ transporter increase the synaptic glycine level and in turn alter the ssGlyR function. Such compounds are useful as muscle relaxant, anesthetic and analgesic agents.

SUMMARY OF THE INVENTION

In one aspect the invention relates to compounds of the formula I:

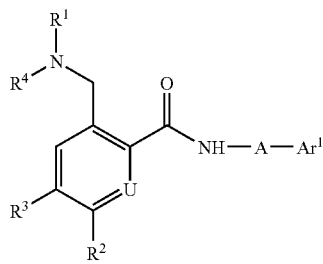

wherein
U is chosen from CH, N and $CR^5$;
A is chosen from the group consisting of ($C_2$ to $C_6$)alkane; ($C_2$ to $C_6$)fluoroalkane; ($C_2$ to $C_6$)alkene; ($C_2$ to $C_6$)alkyne; ($C_2$ to $C_6$)oxaalkane and ($C_2$ to $C_6$)thiaalkane;

B is chosen from the group consisting of a direct bond, ($C_1$ to $C_6$)alkane; substituted ($C_1$ to $C_6$)alkane; and ($C_2$ to $C_6$)azaalkane;
$Ar^1$ and $Ar^2$ are independently chosen from the group consisting of aryl, heteroaryl, substituted aryl and substituted heteroaryl;
$R^2$, $R^3$ and $R^5$ are independently chosen from —H, loweralkyl, fluoroloweralkyl, halo, loweralkoxy, fluoroloweralkoxy and $NO_2$; and
$R^1$ is hydrogen or lower alkyl; and
$R^4$ is —B—$Ar^2$, or
$R^1$ and $R^4$, together with the nitrogen to which they are attached, form a five-, six- or seven-membered nitrogen heterocyle, said nitrogen heterocycle substituted with or fused to $Ar^2$, and said nitrogen heterocycle optionally substituted with from one to three substituents chosen from the group consisting of hydrogen, lower alkyl, —$CH_2OH$, fluoroloweralkyl, —COOH and —COO (lower alkyl)

In another aspect the invention relates to pharmaceutical compositions comprising a pharmaceutically acceptable carrier and a compound of formula I.

In another aspect the invention relates to a method for treating pain comprising administering a therapeutically effective amount of a compound of formula I.

DETAILED DESCRIPTION OF THE INVENTION

In its broadest sense, the invention relates to compounds of the formula I:

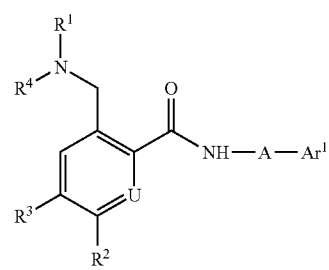

This genus breaks down into two primary subgenera: the 3-(aminomethyl)-2-picolinamides, Ia:

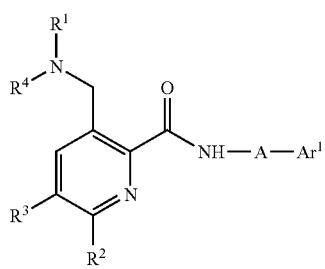

and the 2-(aminomethyl)benzamides, Ib:

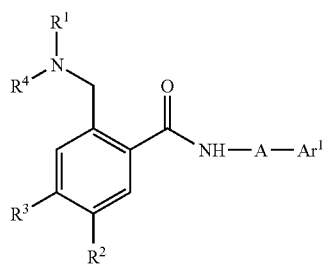

Ib

Because of the greater ease of synthesis, compounds in which $R^2$ and $R^3$ are hydrogen are preferred (in both subgenera), but therapeutically useful compounds are found among those with the $R^2$ and $R^3$ substituents listed.

Preferred values for A are ($C_3$ to $C_6$)alkane; ($C_3$ to $C_5$)alkene; ($C_3$ to $C_5$)alkyne; ($C_3$ to $C_5$)oxaalkane and ($C_3$ to $C_5$)thiaalkane. Examples include —$CH_2CH_2CH=CH$—; —$(CH_2)_5$—; —$(CH_2)_4$—; —$(CH_2)_3$—; —$CH_2CH_2C(CH_3)=CH$—; —$CH_2CH_2C(CF_3)=CH$—; —$CH_2CH_2OCH_2$—; —$CH_2CH_2CH=CH$—; —$(CH_2)_3O$—; —$CH_2CH_2SCH_2$—; and

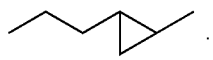

Most preferred are those in which A is ($C_3$ to $C_5$)alkane or ($C_3$ to $C_5$)alkene.

Preferred aryl groups $Ar^1$ are phenyl, halophenyl, dihalophenyl, methoxyphenyl, trifluoromethoxyphenyl, trifluoromethylphenyl, loweralkylphenyl, hydroxyphenyl, and pyridinyl.

The substitution pattern on the aminomethyl ($R^1R^4N$—) breaks down into two major subclasses: (1) those in which $R^1$ is hydrogen or methyl (IIa and IIb):

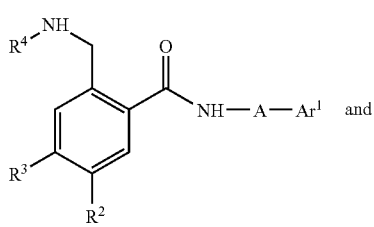

IIa

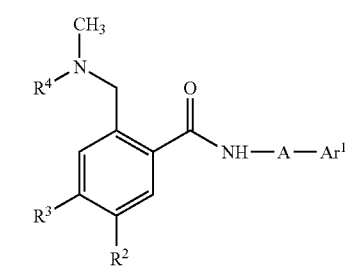

IIb and (2) those in which $R^1$ and $R^4$, together with the nitrogen to which they are attached, form a five-, six- or seven-membered nitrogen heterocycle, which is either fused to $Ar^2$ (IIIa) or substituted with $Ar^2$ (IIIb):

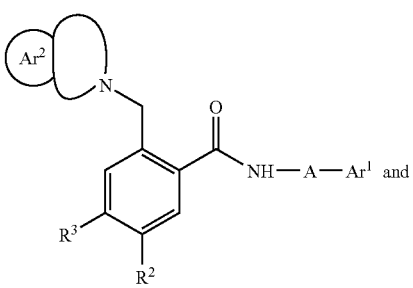

IIIa

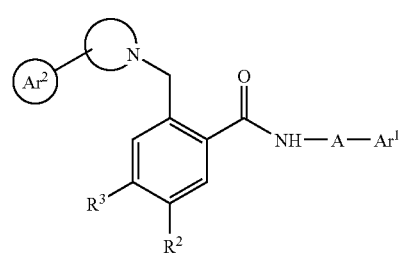

IIIb

In the subgenus II, in which $R^1$ is hydrogen or methyl, B is preferably a direct bond; a ($C_1$ to $C_3$)alkane; or a ($C_2$ or $C_3$)alkane substituted with hydroxy or loweralkoxycarbonyl; or a ($C_2$ or $C_3$)azaalkane. Examples include those in which B is —$CH_2$—; —$CH_2CH_2$—; —$CH_2C(CH_3)$—; —$CH(OH)CH_2$—; —$CH_2CH(COOCH_3)$—; —$NHCH_2CH_2$—; —$N(CH_3)CH_2CH_2$—; and a direct bond. $Ar^2$ is preferably indole; methylindole; hydroxyindole; methoxyindole; haloindole; hydroxytetralin; hydroxybenzocycloheptane; hydroxyindane; phenyl or phenyl substituted with from one to three substituents. The substituents are chosen from methyl, methoxy, hydroxy, amino, trifluoromethyl, hydroxymethyl, formylamino, methanesulfonylamino, aminosulfonyl and loweralkoxycarbonyl. More preferably, $Ar^2$ is hydroxyindole, hydroxytetralin, hydroxyphenyl or formylaminophenyl.

In the class in which $R^1$ and $R^4$, together with the nitrogen to which they are attached, form a five-, six- or seven-membered nitrogen heterocycle, i.e. compounds IIIa and IIIb, the nitrogen heterocycle may be substituted with from one to three substituents chosen from the group consisting of lower alkyl, fluoroloweralkyl, —$CH_2OH$, —$COOH$ and —$COO$(lower alkyl). Examples of cyclic residues in class IIIa, i.e. having $Ar^2$ fused to the heterocycle, include:

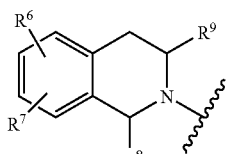
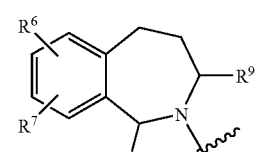
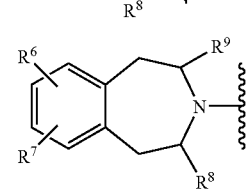
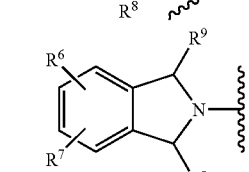

-continued

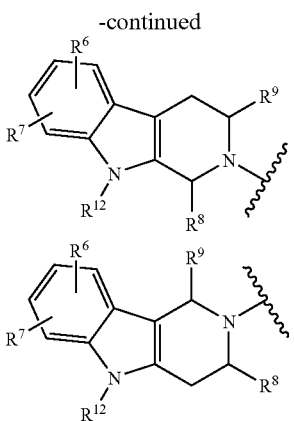

In these exemplary compounds, $R^6$ is hydrogen, hydroxy, loweralkyl, fluoroloweralkyl, loweralkoxyl, fluoroloweralkoxyl or halo; $R^7$ is —$R^{16}$, —$OR^{16}$, —$NH_2$, —$NO_2$, —CN, —NH(CO)NHR$^{17}$, —CONH$_2$, —NH(CO)CH$_3$, —SO$_2$NHR$^{17}$, -halo, —CH$_2$OH, —COOR$^{17}$, —NH(SO$_2$)CH$_3$, or —NH(CO)H; $R^8$ and $R^9$ are independently chosen from —$R^{16}$, —CH$_2$OH, and —COOR$^{17}$; $R^{16}$ is hydrogen, loweralkyl or fluoroloweralkyl; and $R^{12}$ and $R^{17}$ are independently hydrogen or loweralkyl. Examples of cyclic residues having Ar$^2$ as a substituent on the heterocycle formed from the combination of $R^1$, $R^4$ and N (the class of formula IIIb) include:

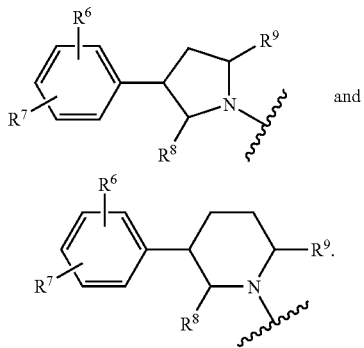

In preferred embodiments, $R^6$ is hydrogen or hydroxy; $R^7$ is hydrogen; $R^8$ is hydrogen or methyl; and $R^9$ is hydrogen, methyl or —CH$_2$OH. PCT application WO2001/054694 discloses tetrahydropyrimidones substituted on one nitrogen with aryl and on the other nitrogen with benzamidomethyl. The compounds are said to be useful for treating type II diabetes. Therefore, applicants have excluded from the claims class IIIb compounds in which the heterocycle is a tetrahydropyrimidone (2-oxopyrimidine).

In general, for classes IIIa and IIIb it is preferred that the heterocycle nitrogen shown in the structures above retain basic character. Thus nitrogen heterocycles in which the basicity of the nitrogen is below a pK$_b$ of about 9 are preferred. More preferred are nitrogen heterocycles in which the nitrogen exhibits a pK$_b$ below 7. Examples of preferred heterocycles for the invention include pyrrolidine, piperidine, morpholine, thiazolidine, oxazoline, oxazolidine, piperazine, dihydro-, tetrahydro- and hexahydroazepine, dihydro-, tetrahydro- and hexahydrothiazepine, dihydro-, tetrahydro- and hexahydrooxazepine, pyrazolidine, imidazole, imidazoline, imidazolidine, benzimidazole, dihydropyrazine, isoxazolidine, isothiazolidine, tetrahydro- and hexahydropyrimidine, thiamorpholine, thiamorpholinesulfoxide, and thiamorpholinesulfone. Also preferred are partially reduced polynuclear nitrogen heterocycles such as tetrahydroisoquinoline and tetrahydrocarboline. In these partially reduced polynuclear nitrogen heterocycles, when one ring remains aromatic, it may furnish Ar$^2$ in structure IIIa, as in the case of tetrahydroisoquinoline and tetrahydrocarboline.

Definitions

Throughout this specification the terms and substituents retain their definitions.

Alkyl and alkane are intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of C$_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

(C$_1$ to C$_n$)Hydrocarbon includes alkyl, cycloalkyl, alkenyl, alkynyl, aryl and combinations thereof containing only hydrogen and one to n carbons. Examples include vinyl, allyl, cyclopropyl, propargyl, phenethyl, cyclohexylmethyl, camphoryl and naphthylethyl. Saturated (C$_1$ to C$_n$)hydrocarbon is identical in meaning to (C$_1$ to C$_n$)alkyl or (C$_1$ to C$_n$)alkane as used herein.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Fluoroalkyl refers to alkyl residues in which one or more hydrogens have been replaced by fluorine. It includes perfluoroalkyl, in which all the hydrogens have been replaced by fluorine. Examples include fluoromethyl, difluoromethyl, trifluoromethyl, trifluoroethyl and pentafluoroethyl.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S. As commonly understood, when referring to aryl as a substituent, it is intended that the point of attachment is a ring carbon of the aryl group (or ring carbon or heteroatom of the heteroaryl). For the purpose of the present invention, aryl and heteroaryl refer to systems in which at least one ring, but not necessarily all rings, are fully aromatic. Thus aromatic 6- to 14-membered carbocyclic rings include, e.g., benzene, naphthalene, indane, tetralin, benzocycloheptane and fluorene and the 5- to 10-membered aromatic heterocyclic rings include, e.g., imidazole, pyridine, indole, isoindoline, thiophene, benzopyranone, thiazole, furan, benzimidazole, quinoline, isoquinoline, tetrahydroisoquinoline, quinoxaline, tetrahydrocarboline, pyrimidine, pyrazine, tetrazole and pyrazole.

Alkylaryl means an alkyl residue attached to an aryl ring. As commonly understood, when referring to alkylaryl as a substituent, it is intended that the point of attachment is the alkyl group. Examples of $C_1$–$C_3$ alkylaryl are benzyl, phenethyl, phenylpropyl and naphthylethyl. Alkylheteroaryl means an alkyl residue attached to a heteroaryl ring. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. It is to be noted that heteroaryl is a subset of heterocycle in which the heterocycle is aromatic. Examples of heterocyclyl residues additionally include piperazinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Substituted alkyl, aryl, cycloalkyl, heterocyclyl etc. refer to alkyl, aryl, cycloalkyl, or heterocyclyl wherein up to three H atoms in each residue are replaced with loweralkyl, halogen, haloalkyl, hydroxy, hydroxymethyl, loweralkoxy, perfluoroloweralkoxy, carboxy, carboalkoxy (also referred to as alkoxycarbonyl), carboxamido (also referred to as alkylaminocarbonyl), sulfonamido, aminosulfonyl, alkylaminosulfonyl, cyano, carbonyl, nitro, amino, alkylamino, dialkylamino, ureido, alkylureido, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

As used herein, reference to "treatment" or "treating" a patient are intended to include prophylaxis. The terms include amelioration, prevention and relief from the symptoms and/or effects associated with these disorders. The terms "preventing" or "prevention" refer to administering a medicament beforehand to forestall or obtund an attack. Persons of ordinary skill in the medical art (to which the present method claims are directed) recognize that the term "prevent" is not an absolute term. In the medical art it is understood to refer to the prophylactic administration of a drug to diminish the likelihood or seriousness of a condition, and this is the sense intended.

Abbreviations

The following abbreviations and terms have the indicated meanings throughout:

| | |
|---|---|
| Ac = | acetyl |
| BNB = | 4-bromomethyl-3-nitrobenzoic acid |
| Boc = | t-butyloxy carbonyl |
| Bu = | butyl |
| c- = | cyclo |
| DBU = | diazabicyclo[5.4.0]undec-7-ene |
| DCM = | dichloromethane = methylene chloride = $CH_2Cl_2$ |
| DEAD = | diethyl azodicarboxylate |
| DIC = | diisopropylcarbodiimide |
| DIEA = | N,N-diisopropylethyl amine |
| DMAP = | 4-N,N-dimethylaminopyridine |
| DMF = | N,N-dimethylformamide |
| DMSO = | dimethyl sulfoxide |
| DVB = | 1,4-divinylbenzene |
| EEDQ = | 2-ethoxy-1-ethoxycarbonyl-1,2-dihydroquinoline |
| Et = | ethyl |
| FCC = | flash column chromography |
| Fmoc = | 9-fluorenylmethoxycarbonyl |
| GC = | gas chromatography |
| HATU = | O-(7-Azabenzotriazol-1-yl)-1,1,3,3-tetramethyluronium hexafluorophosphate |
| HOAc = | acetic acid |
| HOBt = | hydroxybenzotriazole |
| Me = | methyl |
| mesyl = | methanesulfonyl |
| MTBE = | methyl t-butyl ether |
| NMO = | N-methylmorpholine oxide |
| PEG = | polyethylene glycol |
| Ph or κ = | phenyl |
| PhOH = | phenol |
| PfP = | pentafluorophenol |
| PPTS = | pyridinium p-toluenesulfonate |
| PyBroP = | bromo-tris-pyrrolidino-phosphonium hexafluorophosphate |
| rt = | room temperature |
| sat'd = | saturated |
| s- = | secondary |
| t- = | tertiary |
| TBDMS = | t-butyldimethylsilyl |
| TFA = | trifluoroacetic acid |
| THF = | tetrahydrofuran |
| TMOF = | trimethyl orthoformate |
| TMS = | trimethylsilyl |
| tosyl = | p-toluenesulfonyl |
| Trt = | triphenylmethyl |

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Procedure A

One method for preparing compounds of the invention is shown in Scheme 1. A typical solid support (Ⓢ) would be ArgoGel™-NH₂ (Argonaut Technologies, U.S.A.) resin. The linker,

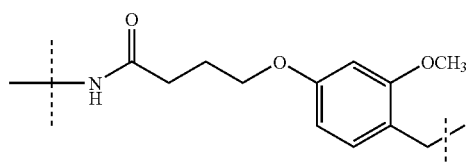

(also represented by ┊), is an aldehyde that is reacted with a primary amine (e.g. 4-phenylbutylamine) under reductive amination conditions to generate a resin bound amine. Acylation of this resin bound amine with 2-chloromethylbenzoyl chloride affords a resin bound amide with a reactive benzylic chloride group. Subsequent reaction with an amine (e.g. tyramine) completes the synthesis and the product is released from the resin by treatment with trifluoroacetic acid. A representative procedure for the solid phase synthesis (Procedure A) and cleavage methods (Procedure C and D) are illustrated below.

Procedure A—Step 1. To a suspension of 2 g (~0.4 mmol/g) of resin-bound aldehyde in 1,2-dichloroethane (20 mL) was added 4-phenylbutylamine (1.08 g, Lancaster, U.S.A.), acetic acid (0.46 mL) and sodium triacetoxyborohydride (1.69 g). The resin suspension was shaken at 25° C. for 16 h. The vessel was drained and the resin was washed with 20 mL portions of dimethylformamide (3×), methanol (3×) and dichloromethane (3×).

Procedure A—Step 2. To a suspension of 0.6 g of resin-bound amine in dichloromethane (6 mL) was added 2-chloromethylbenzoyl chloride (0.11 g, *Tetrahedron Lett*. 1981, 22, 2651–2654) and 2,6-lutidine (0.14 mL). The resin suspension was shaken at 25° C. for 16 h. The vessel was drained and the resin was washed with 6 mL portions of dimethylformamide (3×), methanol (1×) and dichloromethane (3×).

Procedure A—Step 3. To a suspension of 0.2 g resin-bound chloride in dimethylformamide (2.0 mL) was added tyramine (0.11 g), N,N-diisopropylethylamine (0.14 mL) and tetrabutylammonium iodide (0.15 g). The resin suspension was shaken at 25° C. for 16 h. The vessel was drained and the resin was washed with 5 mL portions of dimethylformamide (3×), methanol (3×) and dichloromethane (3×).

Procedure B

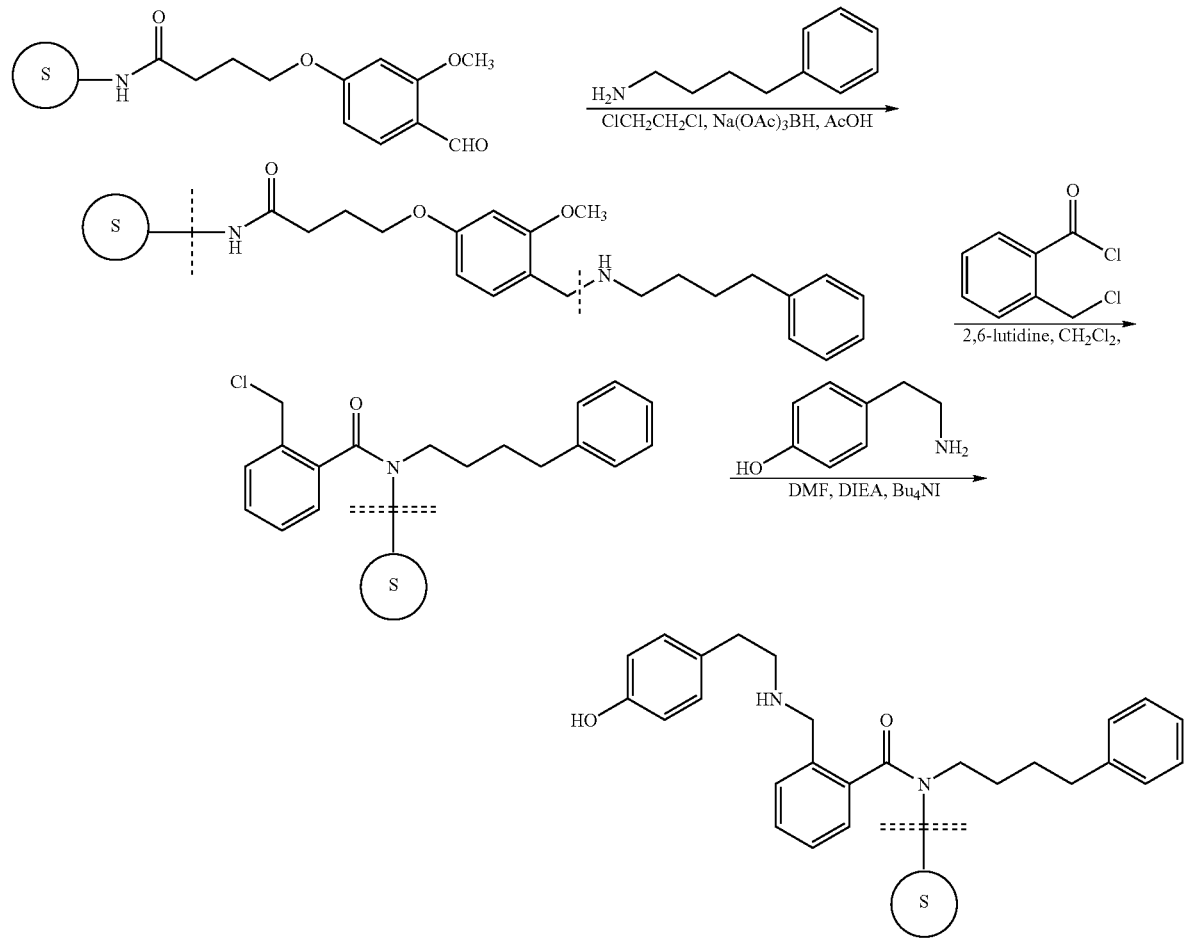

Scheme 1

Compounds of the invention may also be prepared by the route shown in Scheme 2. The resin bound amine (prepared by the same method as Procedure A—Step 1) is acylated with a cyclic anhydride (e.g. 4,5-dichlorophthalic anhydride) to give a resin-bound carboxylic acid, which is activated with pentafluorophenol and reduced to the alcohol. Conversion of the alcohol to bromide or mesylate (bromide is shown here as an example) and subsequent reaction with an amine (e.g. 6-hydroxyl-tetrahydroisoquinoline) completes the synthesis. The product is released from the resin by treatment with trifluoroacetic acid (Procedure C and D). The following is a representative procedure for the solid phase synthesis (Procedure B).

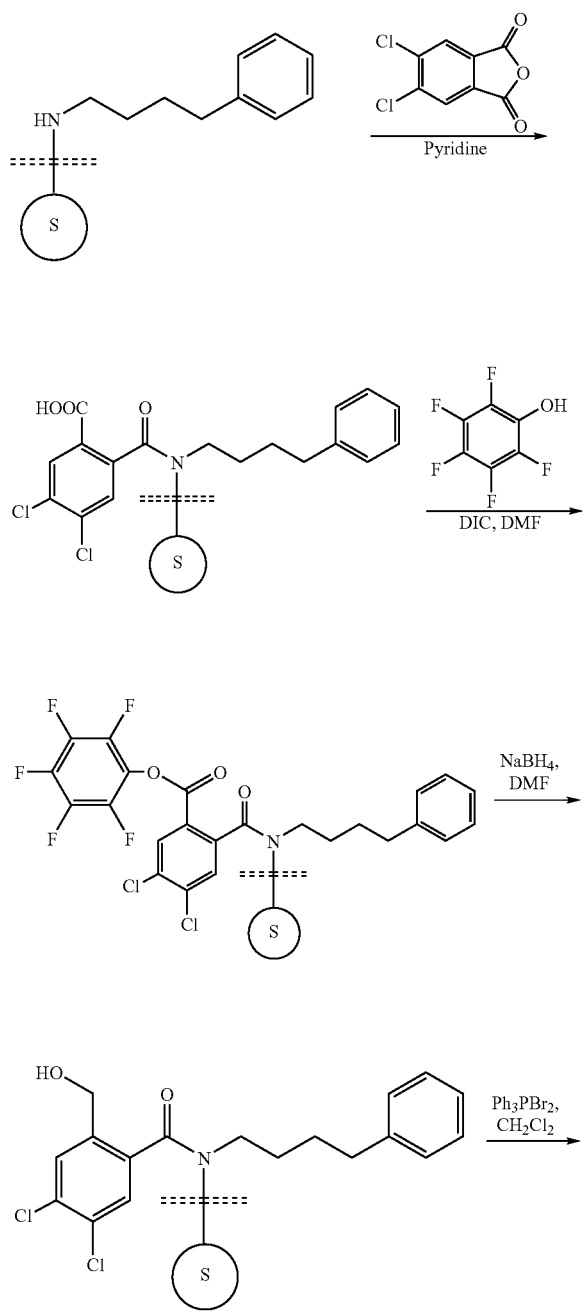

Procedure B—Step 1. To a suspension of 2.0 g (~0.40 mmol/g) of resin-bound amine (prepared by the same procedures as shown in Procedure A—Step 1) in pyridine (15 mL) was added 4,5-dichlorophthalic anhydride (2.6 g). The resin suspension was shaken at 25° C. for 16 h. The vessel was drained and the resin was washed with 15 mL portions of dimethylformamide (3×), methanol (3×) and dichloromethane (3×). The resin was dried in vacuo.

Procedure B—Step 2. A solution of pentafluorophenol (1.47 g, Aldrich, U.S.A.) and diisopropylcarbodiimide (DIC, 1.01 g, Aldrich, U.S.A.) in dimethylformamide (15 mL) was added to resin-bound acid (2.0 g). The resin suspension was shaken at 25° C. for 3 h. The vessel was drained and the resin was washed with 15 mL portions of dimethylformamide (3×).

Procedure B—Step 3. A solution of sodium borohydride (0.15 g) in dimethylformamide (15 mL) was added to 2.0 g of resin-bound ester. The resin suspension was shaken at 25° C. for 1 h. The vessel was drained and the resin was washed with 15 mL portions of dimethylformamide (5×) and dichloromethane (5×).

Procedure B—Step 4. A solution of dibromotriphenylphosphorane (0.21 g, Aldrich, U.S.A.) in dichloromethane (2.5 mL) was added to 0.25 g of resin-bound alcohol. The resin suspension was shaken at 25° C. for 16 h. The vessel was drained and the resin washed with 15 mL portions of dimethylformamide (5×) and dichloromethane (5×).

Procedure B—Step 5. To a suspension of resin-bound bromide (0.25 g) in dimethylformamide (2.5 mL) was added 6-hydroxyl-tetrahydroisoquinoline hydrogen bromide (0.23 g), diisopropylethylamine (0.17 mL) and tetrabutylammonium iodide (0.18 g). The resin suspension was shaken at 25° C. for 16 h. The vessel was drained and the resin washed with 15 mL portions of dimethylformamide (3×), methanol (3×) and dichloromethane (3×).

Procedure C

The resin bound products obtained from Procedure A or B can be cleaved from the resin by treatment with 50% trifluoroacetic acid in dichloromethane. Two representative examples are shown below.

EXAMPLE 1

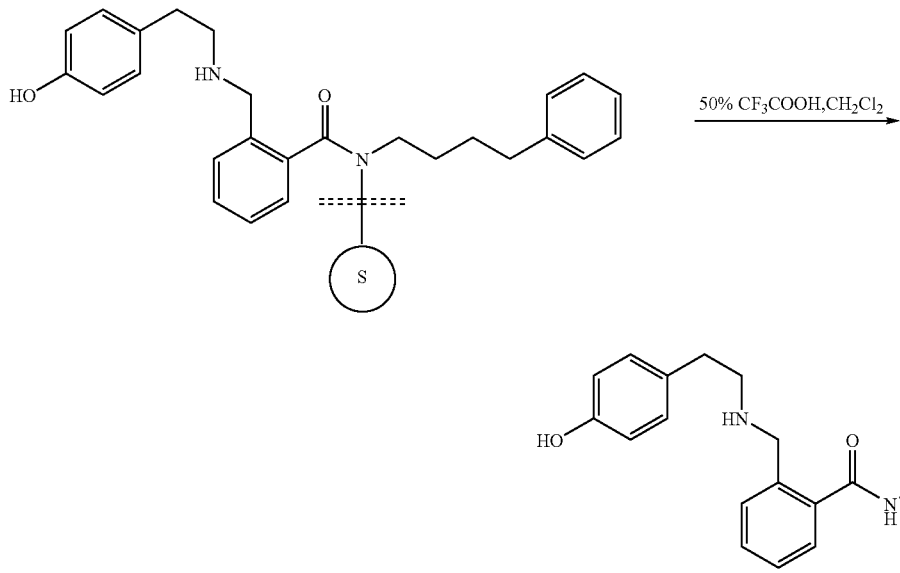

Resin-bound product (~0.20 g) obtained from Procedure A—Step 3 was suspended in 50% TFA/CH$_2$Cl$_2$ (5 mL) and sat at 25° C. for 2 h. The resin was removed by filtration and washed with methanol. The filtrate was concentrated in vacuo and crude product was purified by semi-preparative HPLC to afford 2-{[2-(4-hydroxy-phenyl)-ethylamino]-methyl}-N-(4-phenyl-butyl)-benzamide (37 mg). MS: m/z 403 (m+H).

EXAMPLE 2

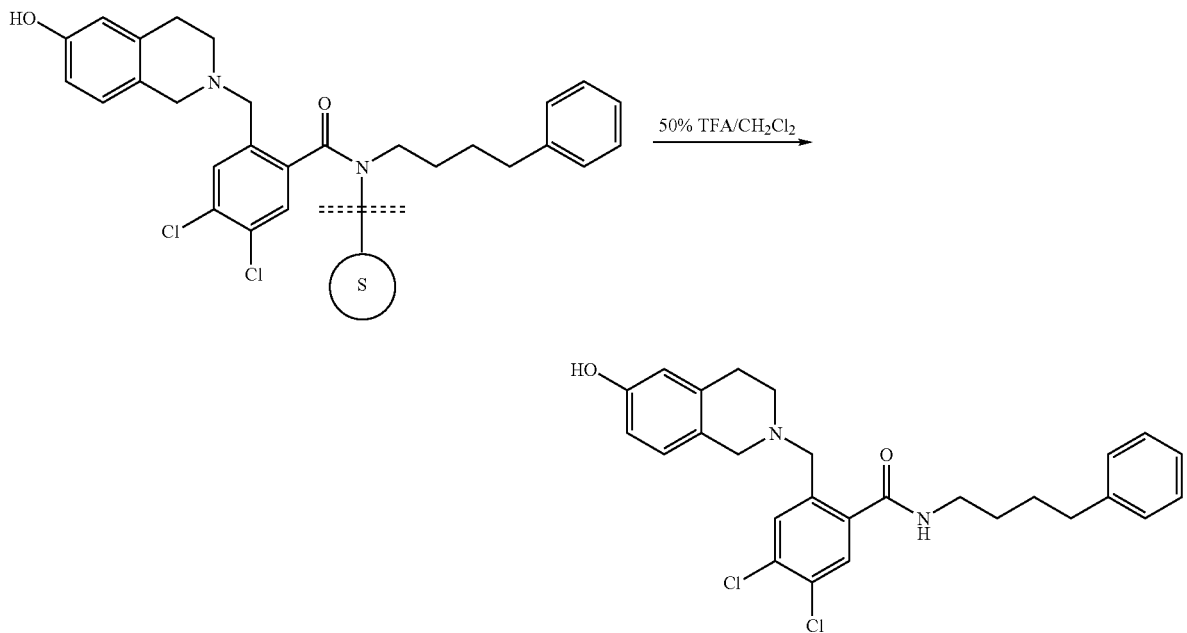

Resin-bound product (~0.25 g) obtained from Procedure B—Step 5 was suspended in 50% TFA/CH$_2$Cl$_2$ (5 mL) and sat at 25° C. for 3 h. The resin was removed by filtration and washed with methanol. The filtrate was concentrated in vacuo and the crude product was purified by semi-preparative HPLC to give 4,5-dichloro-2-(6-hydroxy-3,4-dihydro-1H-isoquinoline-2-ylmethyl)-N-(4-phenyl-butyl)-benzamide (4.4 mg). MS: m/z 483.0 (m+H).

Procedure D

In some cases, the resin-bound product prepared by Procedure A or B contains an indole moiety, 30% trifluoroacetic acid in dichloromethane is used to cleave the product from the resin in order to prevent decomposition of the indole substituent. A representative example is shown below.

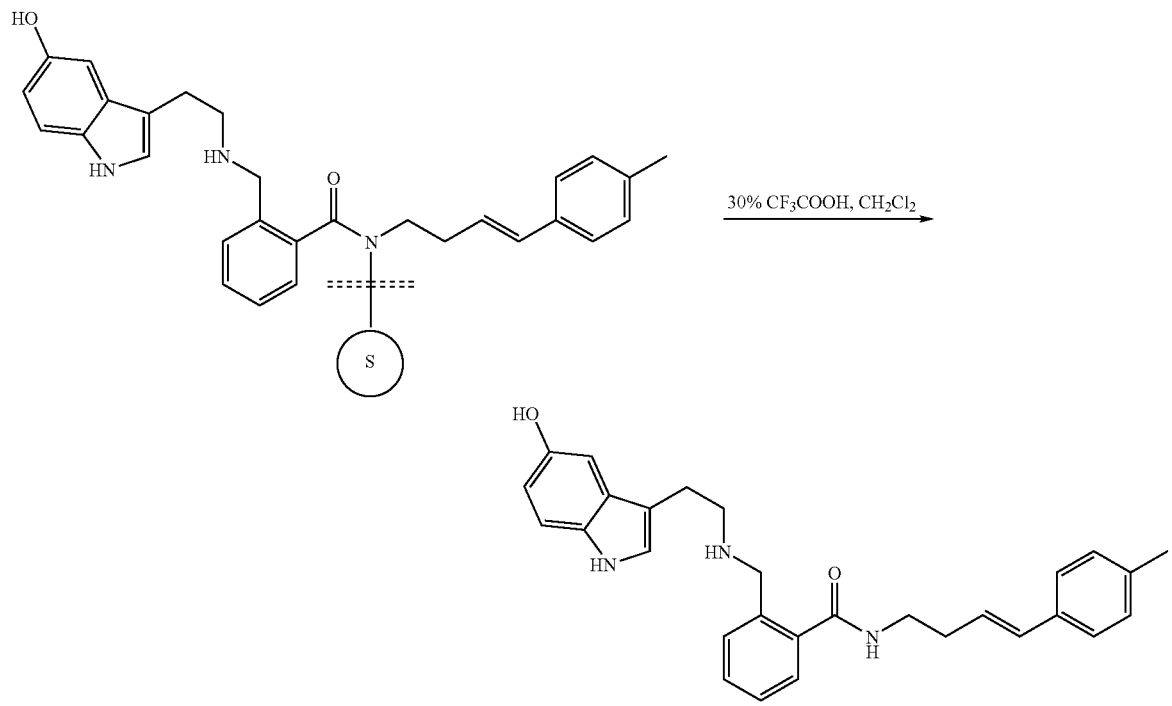

Resin-bound product (1.8 g) was suspended in 30% TFA/CH$_2$Cl$_2$ (20 mL) and allowed to sit at 25° C. for 1 h. The resin was removed by filtration and washed with methanol. The filtrate was concentrated in vacuo and the crude product was purified by semi-preparative HPLC to give 2-{[2-(5-Hydroxy-1H-indol-3-yl)-ethylamino]-methyl}-N-(4-p-tolyl-but-3-enyl)-benzamide (54.9 mg). MS: m/z 454.1 (m+H).

Procedure E

In some cases, a methyl ether product is obtained after the acid cleavage. The methyl ether can be converted to the corresponding phenol by treatment of boron tribromide in dichloromethane. A representative example is shown below.

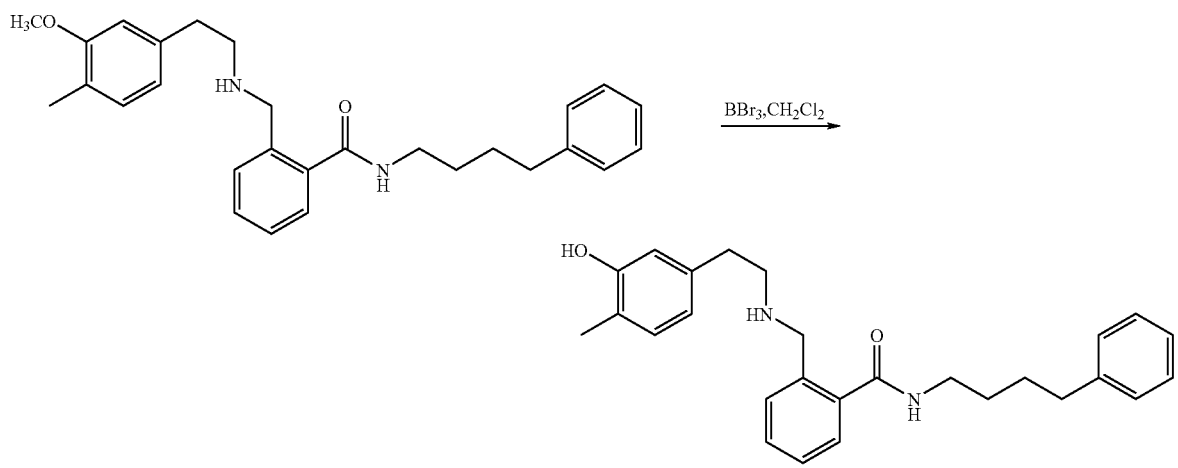

Crude 2-{[2-(3-methoxy-4-methyl-phenyl)-ethylamino]-methyl}-N-(4-phenyl-butyl)-benzamide (derived via Procedure C from 200 mg resin) is dissolved in 3 mL of dichloromethane and treated with 0.5 mL of 1 M of boron tribromide in dichloromethane for 16 h. Methanol (3 mL) is carefully added and the volatiles are removed. The crude residue is purified via semi-preparative HPLC to give 2-{[2-(3-hydroxy-4-methyl-phenyl)-ethylamino]-methyl}-N-(4-phenyl-butyl)-benzamide (28 mg). MS: m/z 417 (m+H).

Synthesis of Amines for Procedure A—Step 1

The amines listed below replaced commercially available 4-phenylbutylamine in Procedure—A Step 1 to provide the compounds shown in Table 1 and 2. Commercially unavailable amines or amine salts used for Procedure A—Step 1 can be prepared by one of the following methods.

Several amines used in Procedure—A Step 1 were synthesized by esterification/amidation of a carboxylic acid, followed by reduction of the resulting amide with either lithium aluminum hydride or diisobutylaluminum hydride.

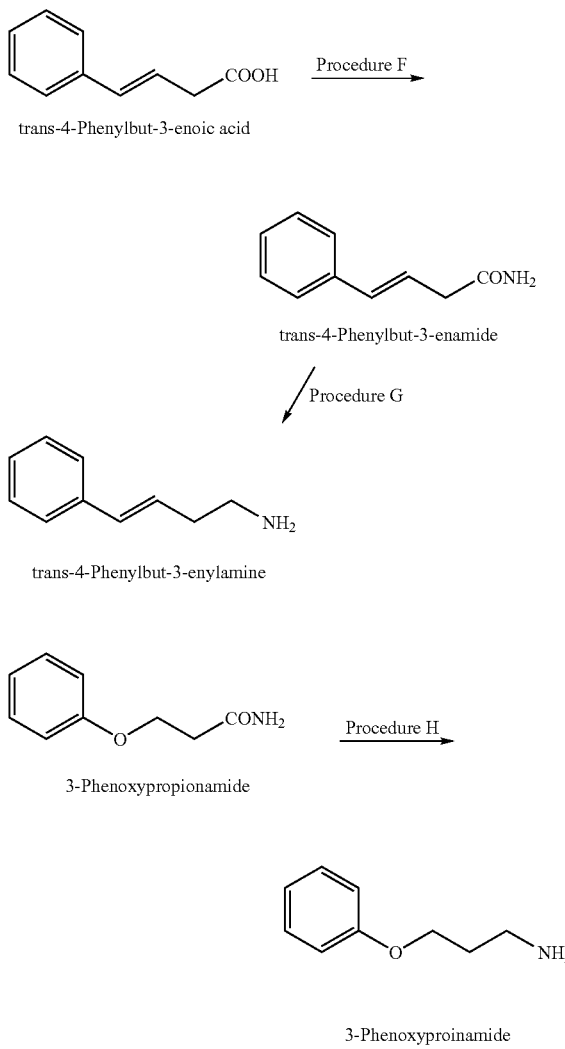

Procedure F—Esterification/Amidation

A solution of chlorotrimethylsilane (40 mL) and 4-phenyl-but-3-enoic acid (40 g, Aldrich, U.S.A.) in methanol (700 mL) was stirred for 20 h. The volatile material was removed by a rotary evaporator and the resulting residue was re-dissolved in methanol (700 mL). The flask was cooled to 0° C. and gaseous ammonia was bubbled into the solution for five minutes. The resulting mixture was sealed and stirred for 6 hours at rt. The flask was unsealed and cooled to 0° C. Ammonia was again bubbled into the solution for five minutes. The flask was resealed and the reaction stirred for 2 days. The volatile material was removed via a rotary evaporator and the crude residue was triturated with diethyl ether to give of 4-phenyl-but-3-enoic acid amide (24 g).

Procedure G—Reduction of Amides with Diisobutylaluminum Hydride

A suspension of 4-phenyl-but-3-enoic acid amide (5.0 g, 31 mmol) in 250 mL dichloromethane was cooled to 0° C. Diisobutylaluminum hydride (1 M in dichloromethane, 250 mL) was added and the resulting homogeneous mixture was allowed to slowly warm to rt. The reaction was stirred for 4 days then quenched by carefully pouring the mixture onto 200 mL of 1:1 water/methanol at 0° C. The aluminum salts were removed by filtration and washed with methanol. The combined filtrate was collected and the volatile material was removed by a rotary evaporator to give of 4-phenyl-but-3-enylamine (3.62 g, 79%) as a pale yellow oil.

Procedure H—Reduction of Amides with Lithium Aluminum Hydride

A solution of 3-phenoxy-propionamide (1.0 g, 6.0 mmol) in diethyl ether (30 mL) was cooled to 0 C. Lithium aluminum hydride (0.46 g, 12 mmol) was added in portions to the stirring amide solution. The resulting slurry was allowed to warm to rt and stirred for 20 h. The mixture was cooled to 0° C. and carefully quenched by the sequential addition of 0.5 mL of water, followed by 0.5 mL of 3 N sodium hydroxide and 1.5 mL of water. The mixture was stirred for 15 min, then filtered to remove the aluminum salts. The filtrate was collected and the volatile material was removed by a rotary evaporator to give 3-phenoxy-propylamine (0.55 g) as a pale green oil.

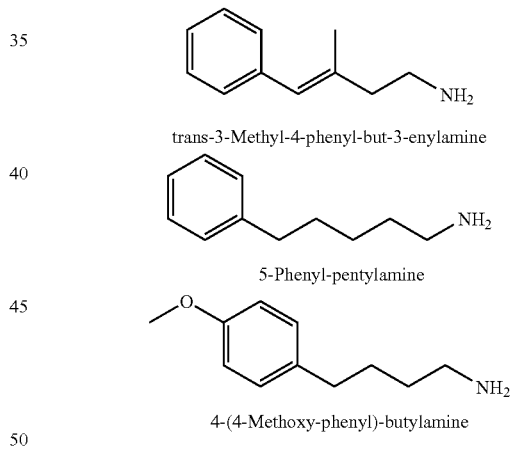

The amines shown above were also made using the esterification/amidation/reduction protocols described above. Procedure G was used to obtain 3-methyl-4-phenyl-but-3-enylamine from commercially available 3-methyl-4-phenyl-but-3-enoic acid amide. Procedure F and H were used to obtain 5-phenyl-pentylamine and 4-(4-methoxy-phenyl)-butylamine from the commercially available carboxylic acid precursors.

Several amines used in Procedure—A Step 1 were synthesized by employing a Wittig reaction between 3-phthalimidopropyltriphenylphosphonium bromide and various aryl aldehydes (J. Med. Chem., 1998, 41, 4080–4100). The cis-alkene intermediates formed from the Wittig reaction were used to make numerous arylbutylamine derivatives via phthalimide group removal followed by hydrogenation. Alternatively, isomerization of the cis double bond in these intermediates to a trans double bond, followed by deprotection with methylamine provided access to several trans-arylbut-3-enylamines.

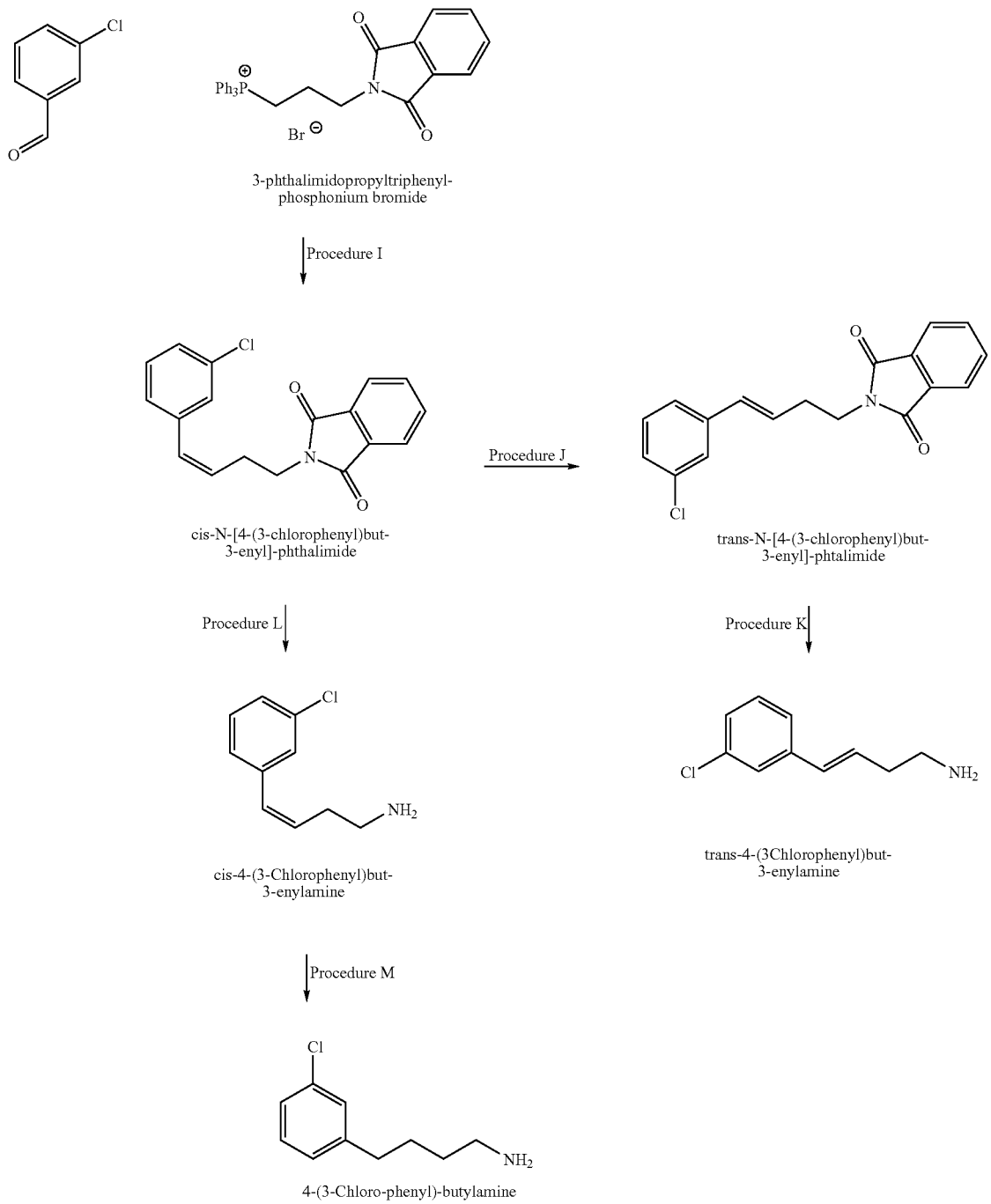

Procedure I—Wittig Reaction of Aryl Aldehydes with 3-Phthalimidopropyltriphenyl-phosphonium bromide.

The 3-phthalimidopropyltriphenylphosphonium bromide was prepared as follows. To a solution of triphenylphosphine (24.5 g, Aldrich, U.S.A.) in toluene (200 mL) was added N-(3-bromopropyl)phthalimide (25 g, Aldrich, U.S.A.). The mixture was heated to reflux overnight. The white solid so formed was isolated by filtration and dried under vacuum to yield 3-phthalimidopropyltriphenylphosphonium bromide (22.8 g).

A mixture of 3-phthalimidopropyltriphenylphosphonium bromide (15.1 g) and 3-chlorobenzaldehyde (4.0 g, Aldrich, U.S.A.) in tetrahydrofuran (150 mL) was cooled to −78° C. in a dry ice/acetone bath. Potassium tert-butoxide (3.2 g) was added and the mixture was stirred for 20 min, then allowed to warm to 0° C. After four hours, the solution was poured into 200 mL water and extracted three times with ethyl acetate. The combined ethyl acetate layers were dried over sodium sulfate, and reduced in vacuo. The residue was dissolved in 200 mL of a 1:1 mixture of ethyl acetate/hexanes, and filtered through a short silica gel plug to remove the triphenylphosphine oxide byproduct. Evaporation of the filtrate yielded 5.7 g of cis-N-[4-(3-chlorophenyl)-but-3-enyl]-phthalimide in a 10:1 ratio of cis:trans isomers.

Procedure J—Isomerization of cis-Alkenes to trans-Alkenes.

A solution of cis-N-[4-(3-chlorophenyl)-but-3-enyl]-phthalimide (1.9 g) and iodine (50 mg) in 500 mL toluene was irradiated for 5 days with a 100-watt incandescent light bulb. The solvent was removed in vacuo and the residue was recrystallized from toluene/methanol to give 0.50 g of trans-N-[4-(3-chlorophenyl)-but-3-enyl]-phthalimide (no cis-isomer was observed by $^1$H-NMR).

Procedure K—Deprotection of the Phthalimido Group with Methyl Amine

A solution of trans-N-[4-(3-chlorophenyl)-but-3-enyl]-phthalimide (0.50 g) and methylamine (2 M in tetrahydrofuran, 8 mL) in 20 mL ethanol was heated to reflux for 4 h. The solution was cooled to rt and the solvent was removed in vacuo. The resulting residue was dissolved in ethyl acetate and extracted 3 times with 1 M hydrochloric acid. The combined acid layers were made basic with potassium hydroxide to pH 9 and extracted with ethyl acetate. The ethyl acetate layer was dried over sodium sulfate and the solvent was removed in vacuo to yield 0.20 g of trans-4-(3-chlorophenyl)-but-3-enylamine.

Procedure L—Deprotection of the Phthalimido Group with Hydrazine

A solution of cis-2-[4-(3-chlorophenyl)-but-3-enyl]-isoindole-1,3-dione (5.7 g) and hydrazine hydrate (1.8 mL) in ethanol (180 mL) was heated at reflux for 16 h. The solution was allowed to cool to rt and the volatiles were removed in vacuo. The resulting residue was dissolved in 2 M sodium hydroxide and extracted three times with ethyl acetate. The organic layers were combined, washed with brine, dried over magnesium sulfate and reduced in vacuo to yield cis-4-(3-chlorophenyl)-but-3-enylamine (2.5 g).

Procedure M—Hydrogenation with Platinum(IV) Oxide as Catalyst.

A solution of cis-4-(3-chlorophenyl)-but-3-enylamine (1.2 g) in 20 mL methanol was added to platinum(IV) oxide monohydrate (0.12 g). The mixture was stirred under 1 atm of hydrogen for 16 h. The mixture was filtered through celite, and the methanol was removed in vacuo to yield 0.9 g of 4-(3-chlorophenyl)-butylamine.

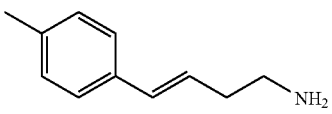

4-p-Tolyl-but-3-enyl amine

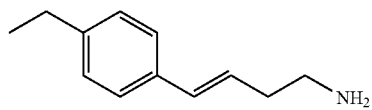

4-(4-Ethyl-phenyl)-but-3-enylamine

-continued

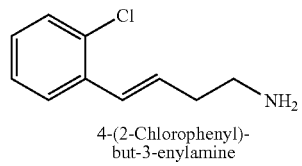

4-(2-Chlorophenyl)-but-3-enylamine

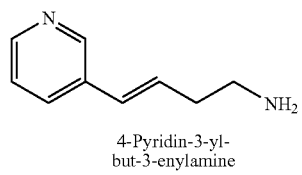

4-Pyridin-3-yl-but-3-enylamine

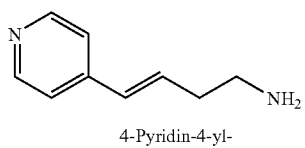

4-Pyridin-4-yl-but-3-enylamine

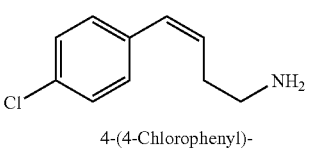

4-(4-Chlorophenyl)-but-3-enylamine

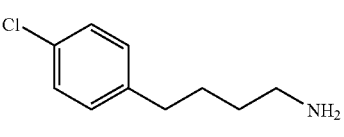

4-(4-Chloro-phenyl)-butylamine

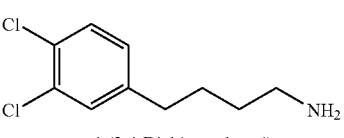

4-(3,4-Dichloro-phenyl)-butylamine

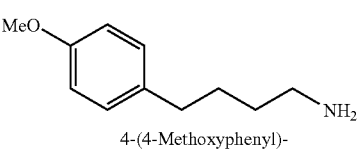

4-(4-Methoxyphenyl)-butylamine

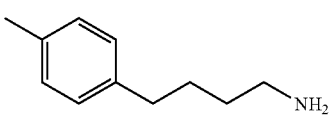

4-p-Tolyl-butylamine

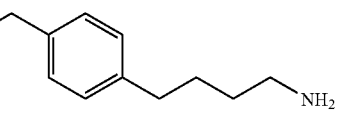

4-(4-Ethyl-phrnyl)-butylamine

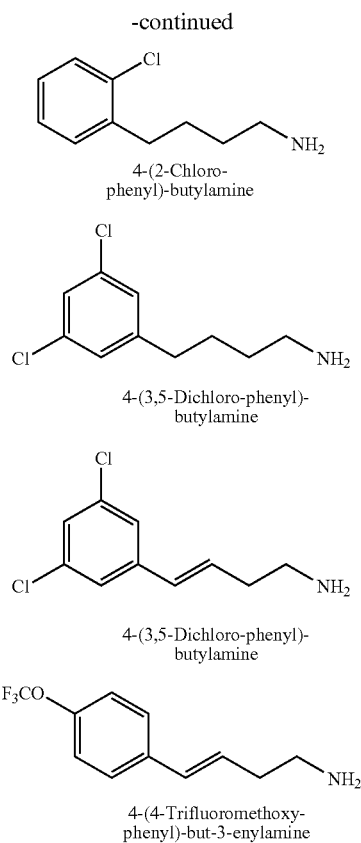
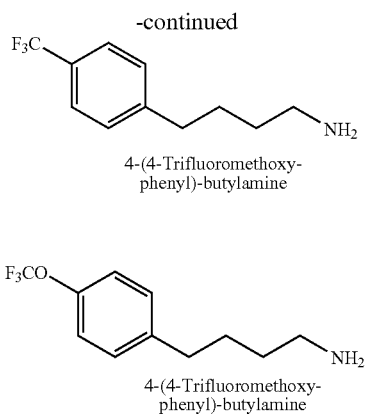

The amines shown above were prepared using the same protocols described in the previous section. The arylbut-3-enylamines were obtained via Procedures I, J, and K, except for 4-(4-chlorophenyl)but-3-enylamine which was prepared by Procedure I and L. The arylbutylamines were obtained by Procedures I, L, and M.

Two amines used in Procedure—A Step 1 were synthesized from pent-4-ynoic acid using a Heck reaction, followed by a Curtius rearrangement. Deprotection of the tert-butoxycarbonyl-intermediate obtained from this reaction sequence gave 4-phenyl-but-3-ynylamine. The tert-butoxycarbonyl-intermediate was also converted to cis-4-phenyl-but-3-enylamine by hydrogenation with Lindlar catalyst and Boc-deprotection.

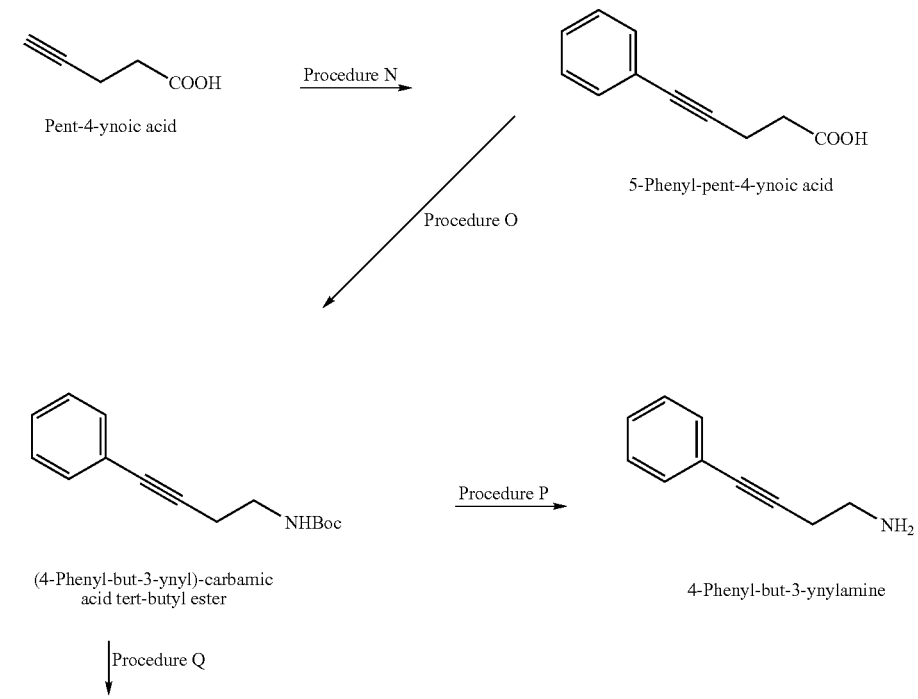

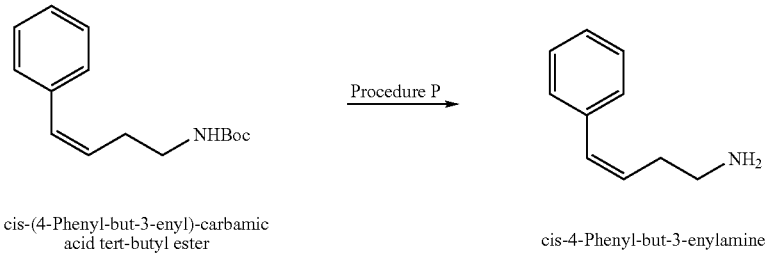

cis-(4-Phenyl-but-3-enyl)-carbamic acid tert-butyl ester cis-4-Phenyl-but-3-enylamine Procedure N—Heck Reaction A solution of pent-4-ynoic acid (1.0 g, 10 mmol), iodobenzene (2.3 ml, 20 mmol), copper(I) iodide (75 mg, 0.40 mmol) and dichlorobis(triphenylphosphine)-platinum(II) (140 mg, 0.20 mmol) in 20 mL of diethylamine was stirred at rt for 3 days. The volatile material are evaporated by a rotary evaporator and the resulting residue was dissolved in 50 mL dichloromethane and washed with 1 M HCl (50 mL). The dichloromethane layer was dried over sodium sulfate and evaporated to dryness under vacuum. The residue was purified by column chromatography (ethyl acetate/dichloromethane) to afford 5-phenylpent-4-ynoic acid (0.49 g).

Procedure O—Curtius Rearrangement

A solution of 5-phenylpent-4-ynoic acid (0.49 g), diphenylphosphoryl azide (0.66 mL) and triethylamine (0.43 mL) was refluxed in 15 mL toluene for 3 h. The reaction was cooled to rt and t-butyl alcohol was added. The reaction was refluxed for 16 h, then the volatile materials were removed via a rotary evaporator. The residue was purified by column chromatography on silica (2–6% ethyl acetate in hexanes) to give (4-phenyl-but-3-ynyl)-carbamic acid tert-butyl ester (0.3 g).

Procedure P—TFA-Mediated Deprotection of the Boc Group.

A solution of (4-phenyl-but-3-ynyl)-carbamic acid tert-butyl ester (98 mg) was stirred for 0.5 h in 1:1 trifluoroacetic acid/dichloromethane (10 ml). The volatile materials were evaporated to give the crude 4-phenyl-but-3-ynylamine, which was used in subsequent transformations without further purification.

Procedure Q—Lindlar Hydrogenation

A suspension of palladium on barium sulfate (15 mg) was stirred for 15 min in 1 mL pyridine. (4-phenyl-but-3-ynyl)-carbamic acid tert-butyl ester (66 mg) was added and the solution was purged with hydrogen then stirred for 1 h under a hydrogen-filled balloon. The solution was diluted with ethyl acetate (10 ml) and washed 3 times with 1 N hydrochloric acid (10 ml). The ethyl acetate layer was dried over sodium sulfate and filtered. The filtrate was evaporated and the resulting residue (54 mg) is primarily cis-(4-phenyl-but-3-enyl)-carbamic acid tert-butyl ester along with (4-phenyl-but-3-ynyl)-carbamic acid tert-butyl ester, 4-phenylbutylamine, and trans-(4-phenyl-but-3-enyl)-carbamic acid tert-butyl ester. The combined minor products constitute ~20% of the crude material. The tert-butoxycarbonyl group of the desired product was removed by Procedure P to give cis-4-phenyl-but-3-enylamine, which was used in subsequent transformations without further purification.

2-(2-Phenyl-cyclopropyl)-ethylamine was prepared by a literature procedure (*Tetrahedron*, 1974, 30, 2173–2181).

4-Phenyl-butylamine, 3-phenyl-propylamine and 2-benzylsulfanyl-ethylamine were obtained form commercial sources.

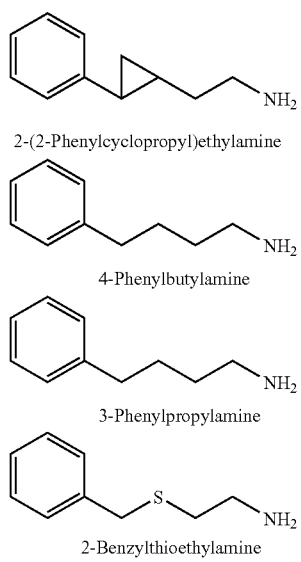

2-(2-Phenylcyclopropyl)ethylamine

4-Phenylbutylamine

3-Phenylpropylamine

2-Benzylthioethylamine

Synthesis of Amines for Procedure A—Step 3 and Procedure B—Step 5

The amines listed below replaced the tyramine in Procedure—A Step 3 and the 6-hydroxyltetrahydroisoquinoline in Procedure B—Step 5 to provide the compounds shown in Table 1 and 2. Commercially unavailable amines or amine salts used for either procedures can be prepared by one of the following methods.

Several amines used in Procedure—A Step 3 and/or Procedure—B Step 5 were synthesized by esterification/amidation of a carboxylic acid followed by reduction of the resulting amide with lithium aluminum hydride. For example, the two amines shown below were synthesized from the corresponding carboxylic acids by employing Procedures F and H previously described.

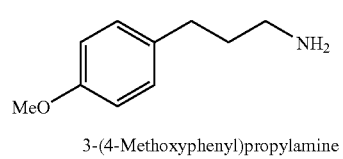

3-(4-Methoxyphenyl)propylamine

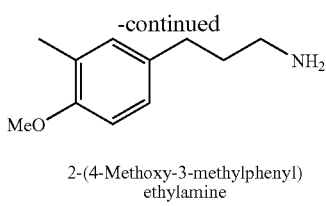

2-(4-Methoxy-3-methylphenyl)
ethylamine

However, some compounds were prepared by a protection/deprotection scheme (Procedures S and T) and a modified esterification/amidation procedures (Procedure R). For example, 2-[4-(tert-butyldimethylsilanyloxy)-3-chlorophenyl]acetamide prepared from (3-chloro-4-hydroxy-phenyl)-acetic acid by Procedure R and S, was subsequently reduced to the corresponding amine using lithium aluminum hydride (Procedure H) and loaded on to resin according to the Procedure A—Step 3. This was then deprotected by Procedure T before cleavage from the resin.

ethyl acetate was evaporated and the intermediate methyl ester was stirred for 16 h in 50 mL of concentrated ammonium hydroxide. Evaporation of the ammonium hydroxide gave 2.3 g of 2-(3-chloro-4-hydroxy-phenyl)-acetamide.

Procedure S—Protection with the tert-Butyldimethylsilyl Group.

A solution of 2-(3-chloro-4-hydroxy-phenyl)-acetamide (100 mg), imidazole (184 mg), and tert-butyldimethylsilyl chloride (163 mg) was stirred for 2 h in 5 mL of dimethylformamide. The solution was diluted with 50 mL of ethyl acetate and washed with 50 mL of sodium carbonate. The ethyl acetate was evaporated to afford 125 mg of 2-[4-(tert-butyldimethylsilanyloxy)-3-chlorophenyl]acetamide.

Procedure T—Deprotection of the tert-Butyldimethylsilyl Group

Solid tetrabutylammonium fluoride (105 mg) was added to a suspension of the resin-bound tert-butyldimethylsilyl ether (100 mg, 0.04 mmol) in 15 mL tetrahydrofuran. The

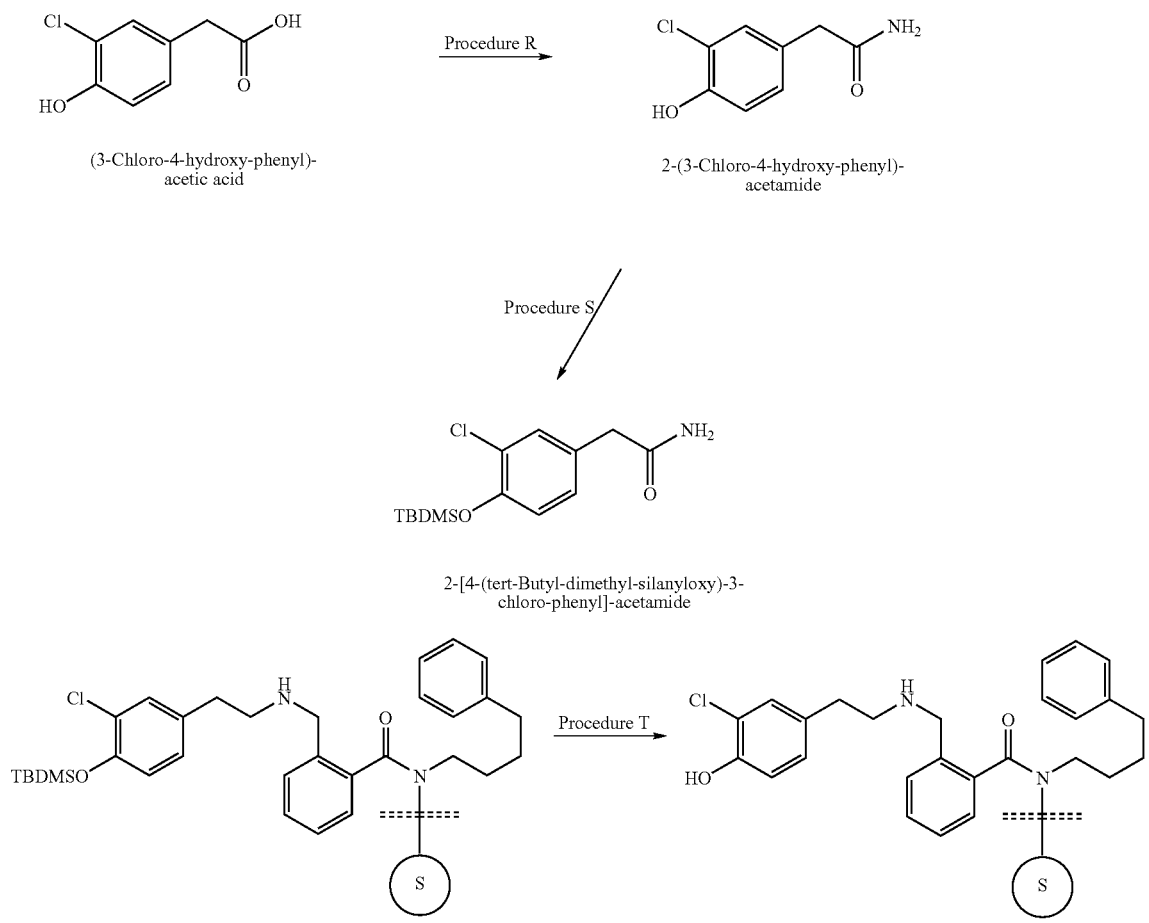

Procedure R—Synthesis of (3-Chloro-4-hydroxyphenyl)acetamide.

A solution of (3-chloro-4-hydroxyphenyl)acetic acid (5.5 g) and sulfuric acid (0.5 mL) was stirred for 16 h in 100 mL of methanol. The volatile material was removed by evaporation and the resulting residue was dissolved in 100 mL of ethyl acetate. The ethyl acetate solution was washed 3 times with brine (100 mL) and dried over sodium sulfate. The flask was shaken for 3 h and then the soluble material was drained. The beads were washed twice with 15 mL aliquots of dimethylformamide, twice with 15 mL aliquots of methanol, and twice with 15 mL aliquots of dichloromethane.

Secondary amide was obtained from a different esterification/amidation procedure (Procedure U) and was converted to the corresponding secondary amine by using Procedure H.

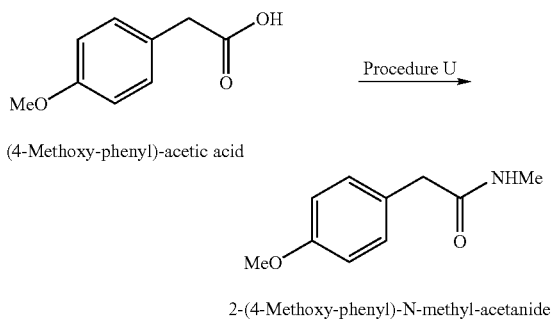

(4-Methoxy-phenyl)-acetic acid 2-(4-Methoxy-phenyl)-N-methyl-acetamide

Procedure U—Synthesis of 2-(4-Methoxyphenyl)-N-methylacetamide

Solid 1-(3-dimethylaminopropyl)-3-ethylcarbodiimide hydrochloride (0.60 g) was added to a stirred suspension of (4-methoxyphenyl)acetic acid (0.50 g) and 1-hydroxybenzotriazine hydrate (0.40 g) in 10 mL tetrahydrofuran. The mixture was stirred for 30 min, then methylamine (2.0 M in THF, 6.0 mL) was added. Stirring was continued for 12 h and the volatile material was subsequently evaporated. The crude residue was dissolved in 50 mL of EtOAc and washed twice with 50 mL of 1 M hydrochloric acid, twice with 50 mL of saturated sodium bicarbonate, and twice with 50 mL of saturated sodium chloride. Evaporation of the ethyl acetate gives 0.45 g of 2-(4-methoxyphenyl)-N-methylacetamide.

Several amines were synthesized by the reduction of the corresponding nitrites with lithium aluminum hydride (Procedure V).

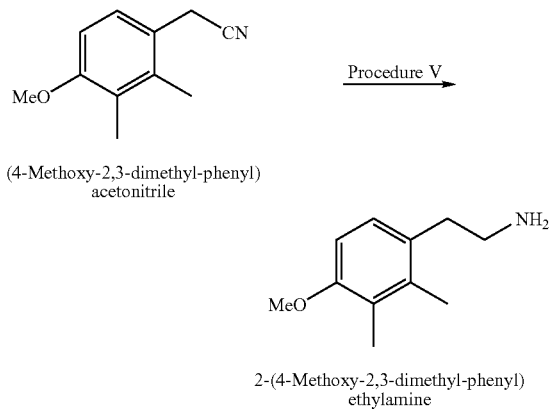

(4-Methoxy-2,3-dimethyl-phenyl) acetonitrile 2-(4-Methoxy-2,3-dimethyl-phenyl) ethylamine Procedure V—Standard Reduction of Nitriles to Amines with Lithium Aluminum Hydride.

A solution of (4-methoxy-2,3-dimethylphenyl)acetonitrile (0.20 g) in 15 mL diethyl ether was cooled to 0° C. Lithium aluminum hydride (0.20 g) was added in portions to the stirring nitrile solution. The resulting slurry was allowed to warm to rt and stirred for 20 h. The mixture was cooled to 0° C. and carefully quenched by the sequential addition of 0.2 mL of water, followed by 0.2 mL of 3 N sodium hydroxide and 0.6 mL of water. The mixture was stirred for 15 min to remove the aluminum salts. The filtrate was collected and the volatile material was removed by a rotary evaporator to give 130 mg of 2-(4-methoxy-2,3-dimethylphenyl)ethylamine.

The following amines were prepared from the corresponding nitrites by using Procedure V.

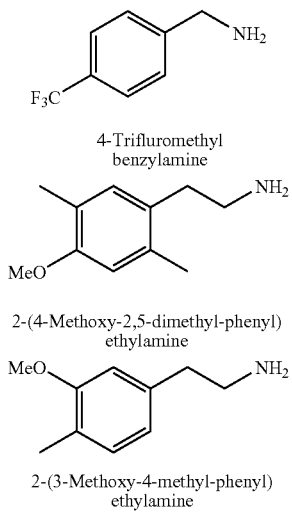

4-Trifluromethyl benzylamine 2-(4-Methoxy-2,5-dimethyl-phenyl) ethylamine 2-(3-Methoxy-4-methyl-phenyl) ethylamine Amines with α-substitution were prepared from the ketones by a reductive amination procedure (Procedure X). Similarly, tetrahydronaphthalenylamines were prepared from the corresponding tetralones by the same procedures.

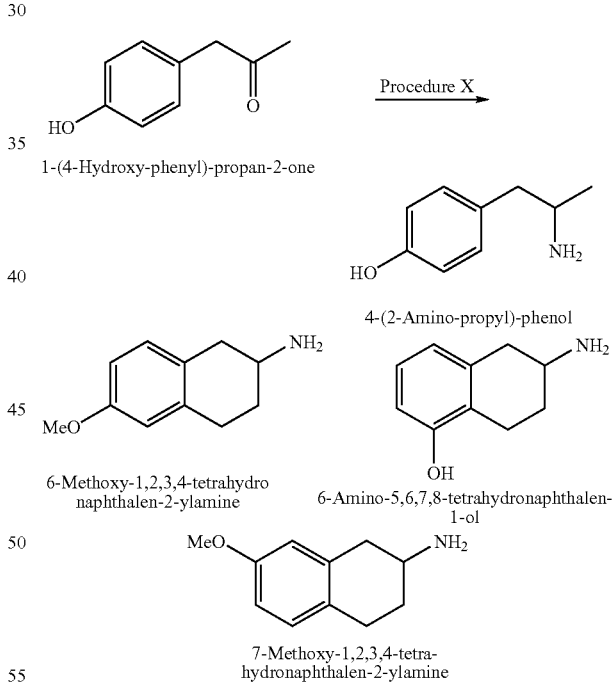

1-(4-Hydroxy-phenyl)-propan-2-one 4-(2-Amino-propyl)-phenol

6-Methoxy-1,2,3,4-tetrahydro naphthalen-2-ylamine

6-Amino-5,6,7,8-tetrahydronaphthalen-1-ol

7-Methoxy-1,2,3,4-tetrahydronaphthalen-2-ylamine

Procedure X—Standard Reductive Amination

To a solution of 4-hydroxyphenylacetone (0.5 g, Avocado, U.K.) and ammonium acetate (2.54 g, Aldrich, U.S.A.) in 10 mL methanol was added 0.17 g of sodium cyanoborohydride (Aldrich, U.S.A.). After stirring for 72 h at rt, concentrated hydrochloric acid was added dropwise until the solution reached pH 2. The solvent was evaporated and the resulting residue was dissolved in water, then extracted 3 times with diethyl ether. The aqueous layer was neutralized to pH 8 by the addition of potassium hydroxide and extracted with diethyl ether. The basic ether layer was dried over sodium sulfate and the solvent was removed in vacuo to give 0.23 g of 4-(2-amino-propyl)-phenol.

In one case, a secondary amine was obtained from a β-tetralone using methylamine instead of ammonia (Procedure Y).

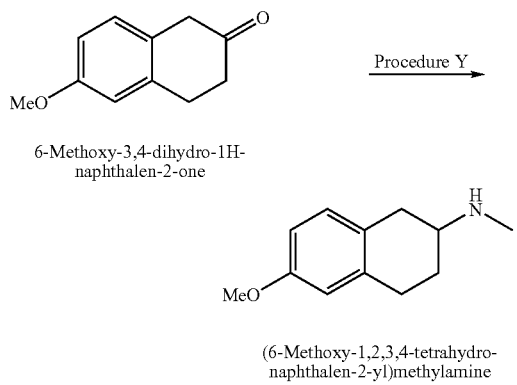

Procedure Y—Synthesis of (6-Methoxy-1,2,3,4-tetrahydro-naphthalen-2-yl)methylamine.

A solution of 6-methoxy-3,4-dihydro-1H-naphthalen-2-one (176 mg, Aldrich, U.S.A.), acetic acid (0.57 mL), methylamine (2.0 M in tetrahydrofuran, 5.0 mL), and sodium cyanoborohydride (64 mg) was stirred in 5 mL methanol for 20 h. The solution was acidified to a pH<2 with concentrated hydrochloric acid, diluted with water to a volume of 50 mL, and extracted with 50 mL of dichloromethane. The aqueous phase was made basic (pH>10) by the addition of 1 M sodium hydroxide and extracted with two 50 mL aliquots of dichloromethane. The basic dichloromethane extracts were dried in vacuo to yield 80 mg of (6-methoxy-1,2,3,4-tetrahydronaphthalen-2-yl)methylamine.

In two cases, aldehydes were converted to the corresponding nitroalkenes by condensation with nitromethane. The nitroalkenes were then reduced to amines via hydrogenation or by lithium aluminum hydride.

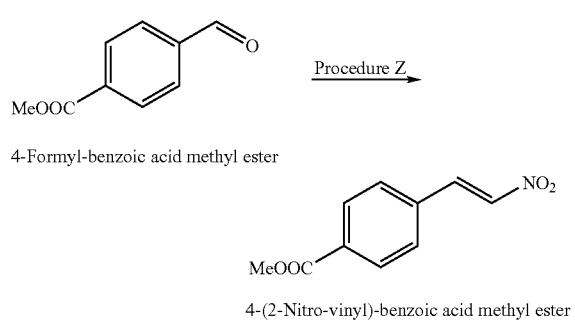

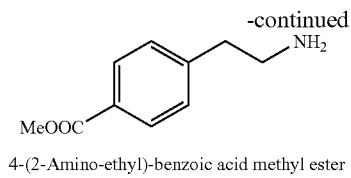

4-(2-Amino-ethyl)-benzoic acid methyl ester

Procedure Z—Nitromethane Condensation to an Aryl Aldehyde.

Sodium hydroxide (1 N, 2.3 mL) was added dropwise to 4-formyl-benzoic acid methyl ester (0.33 g) and nitromethane (0.11 ml) in 5 mL methanol at 0° C. The solution was acidified after 0.5 h and a precipitate was formed. The precipitate was isolated by filtration to give 228 mg of 4-(2-nitro-vinyl)-benzoic acid methyl ester.

Procedure AA—Reduction of a Nitroalkene via Hydrogenation.

Palladium on carbon (10%, 50 mg) was added to a solution of 4-(2-nitrovinyl)benzoic acid methyl ester (228 mg) in 5 mL of ethyl alcohol and 2 mL of acetic acid. The reaction vessel was saturated with hydrogen and stirred under a 1 atm hydrogen atmosphere for 20 h. The vessel was saturated with nitrogen and filtered through celite. Evaporation of the solvents gave 205 mg of crude 4-(2-amino-ethyl)-benzoic acid methyl ester.

In another example, tert-butyl-[2,6-dimethyl-4-(2-nitrovinyl)phenoxy]-dimethylsilane was reduced to the corresponding amine by lithium aluminum hydride.

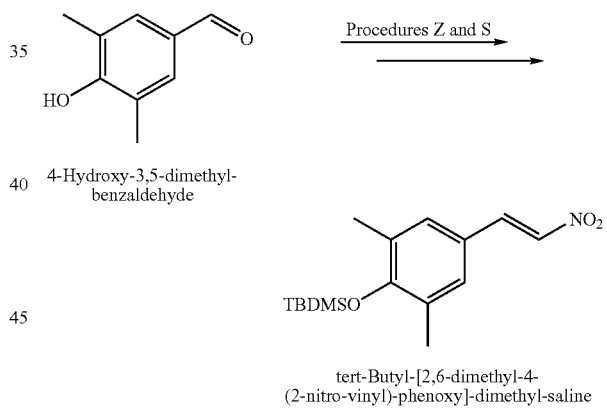

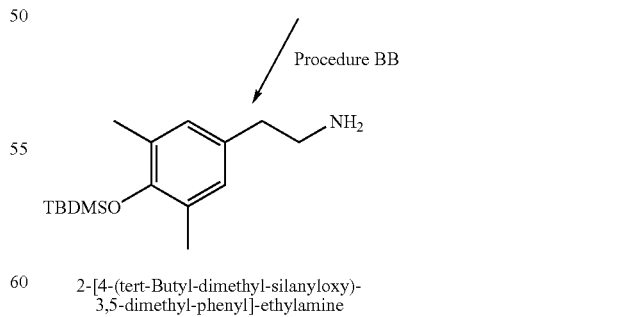

Procedure BB—Reduction of a Nitroalkene via Lithium Aluminum Hydride.

A solution of tert-butyl-[2,6-dimethyl-4-(2-nitrovinyl)phenoxy]dimethylsilane (0.20 g) in 15 mL diethyl ether was cooled to 0° C. Lithium aluminum hydride (0.20 g) was added in portions to the stirring nitroalkene solution. The resulting slurry was refluxed for 3 h and then cooled to 0° C. The mixture is carefully quenched by the sequential addition of 0.2 mL of water, followed by 0.2 mL of 3 N sodium hydroxide and 0.6 mL of water. The mixture was stirred for 15 min, then filtered to remove the aluminum salts. The filtrate was collected and the volatile material was removed by a rotary evaporator to give 100 mg of 2-[4-(tert-butyldimethylsilanyloxy)-3,5-dimethylphenyl]ethylamine.

N-[4-(2-Amino-ethyl)-phenyl]-formamide, N-[4-(2-Amino-ethyl)-phenyl]-methanesulfonamide and N-[4-(2-Amino-ethyl)-phenyl]-acetamide were prepared from 4-(2-aminoethyl)phenylamine by capping the aniline amino group with a formyl, methanesulfonyl, and acetyl group via the intermediate [2-(4-aminophenyl)-ethyl]-carbamic acid tert-butyl ester.

by the careful addition of 1 N hydrochloric acid. The aqueous solution was extracted twice with 50 mL aliquots of dichloromethane and the solvent is evaporated. The resulting residue is stirred in 30% trifluoroacetic acid for 2 h to afford, after evaporation of the solvent, 30 mg of N-[4-(2-aminoethyl)phenyl]methanesulfonamide.

Procedure FF

Acetyl chloride (59 µL) was added to an ice-cold solution of [2-(4-amino-phenyl)-ethyl]-carbamic acid tert-butyl ester (125 mg) in 10 mL of 1:1 dichloromethane: pyridine. The mixture was allowed to warm to rt and stirred for another 2 h. The solution was poured on 50 mL of water and acidified to pH 5 by the careful addition of 1 N hydrochloric acid. The aqueous solution was extracted twice with 50 mL aliquots of dichloromethane and the solvent was evaporated. The resulting residue was purified by silica gel chromatography (30%

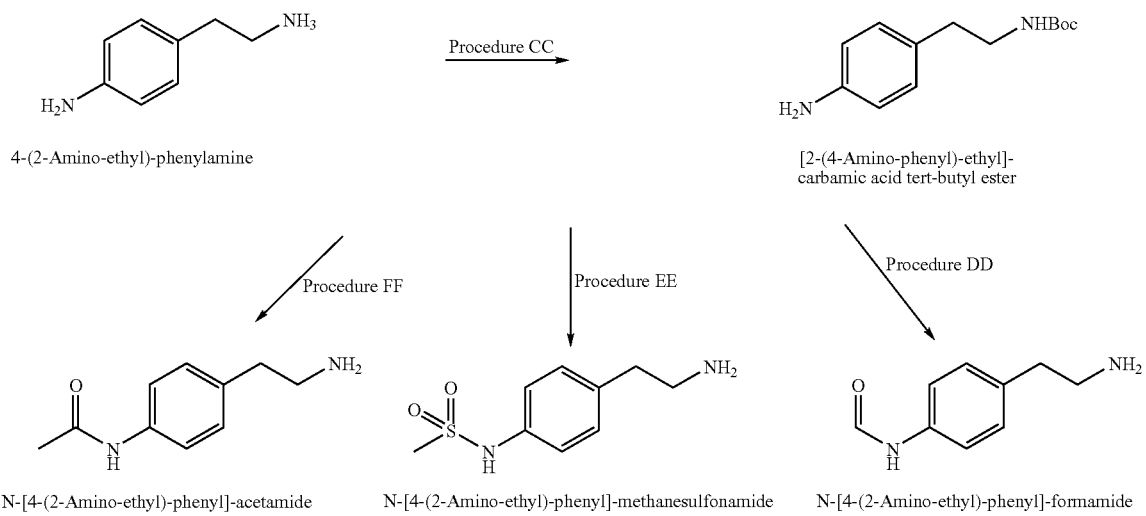

Procedure CC

A solution of 4-(2-aminoethyl)phenylamine (1.5 g) and di-tert-butyl dicarbonate (2.6 g) was stirred for 5 h in 20 mL of 1,4-dioxane. The solvent was evaporated and the crude residue was purified by silica gel chromatography (30% ethyl acetate in hexanes) to give 1.3 g of [2-(4-amino-phenyl)-ethyl]-carbamic acid tert-butyl ester.

Procedure DD

Acetic acid (283 µL) was added to a solution of formic acid (1.7 mL) in 5 mL of chloroform. The solution was stirred for 0.5 h and cooled to 0° C. A solution of [2-(4-amino-phenyl)-ethyl]-carbamic acid tert-butyl ester (350 mg) in 1 mL of chloroform was added to the solution. After the reaction was stirred for 1 h at rt, the solvent was evaporated. The crude residue was purified by silica gel chromatography (30% ethyl acetate in hexanes). The purified material was deprotected by treatment with 20% trifluoroacetic acid in dichloromethane for 2 h to give 150 mg of N-[4-(2-mino-ethyl)-phenyl]-formamide.

Procedure EE

Methanesulfonyl chloride (32 µL) was added to an ice-cold solution of [2-(4-Amino-phenyl)-ethyl]-carbamic acid tert-butyl ester (75 mg) in 5 mL of pyridine. The mixture was allowed to warm to rt and stirred for another 12 h. The solution is poured on 50 mL of water and acidified to pH 5 ethyl acetate in hexanes), then stirred in 30% trifluoroacetic acid for 2 h to afford, after evaporation of the solvent, 75 mg of N-[4-(2-Amino-ethyl)-phenyl]-acetamide.

Other methods (Procedure GG to LL) are employed to synthesize amines for Procedure A—Step 1.

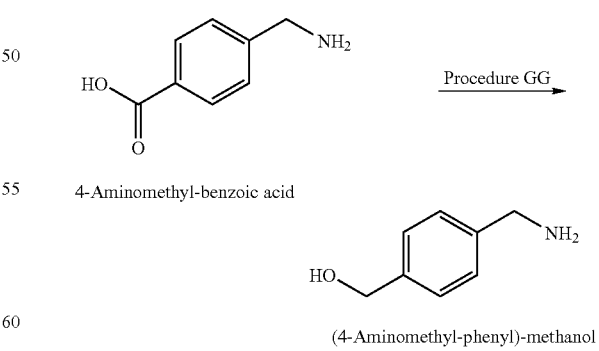

Procedure GG

A solution of 4-aminomethyl-benzoic acid (0.20 g) in 20 mL diethyl ether was cooled to 0° C. Lithium aluminum hydride (0.19 g) was added in portions to the stirring carboxylic acid solution. The resulting slurry was stirred for 20 h and then cooled to 0 C. The mixture was carefully quenched by the sequential addition of 0.2 mL of water followed by 0.2 mL of 3 N sodium hydroxide followed by 0.6 mL of more water. The mixture was stirred for 15 min, then filtered to remove the aluminum salts. The filtrate was collected and the volatile material was evaporated to give 150 mg of (4-aminomethyl-phenyl)-methanol.

Procedure II

Solid thallium(III) nitrate trihydrate (1.7 g) was added to a solution of 6-methoxy-1-methylene-1,2,3,4-tetrahydro-naphthalene (66–75% pure, 0.66 g) in 10 mL of methyl alcohol. The mixture was stirred for 5 min, then diluted with dichloromethane and filtered to remove the insoluble thallium byproduct. The filtrate was collected and washed with saturated sodium hydrogen carbonate. The volatile material

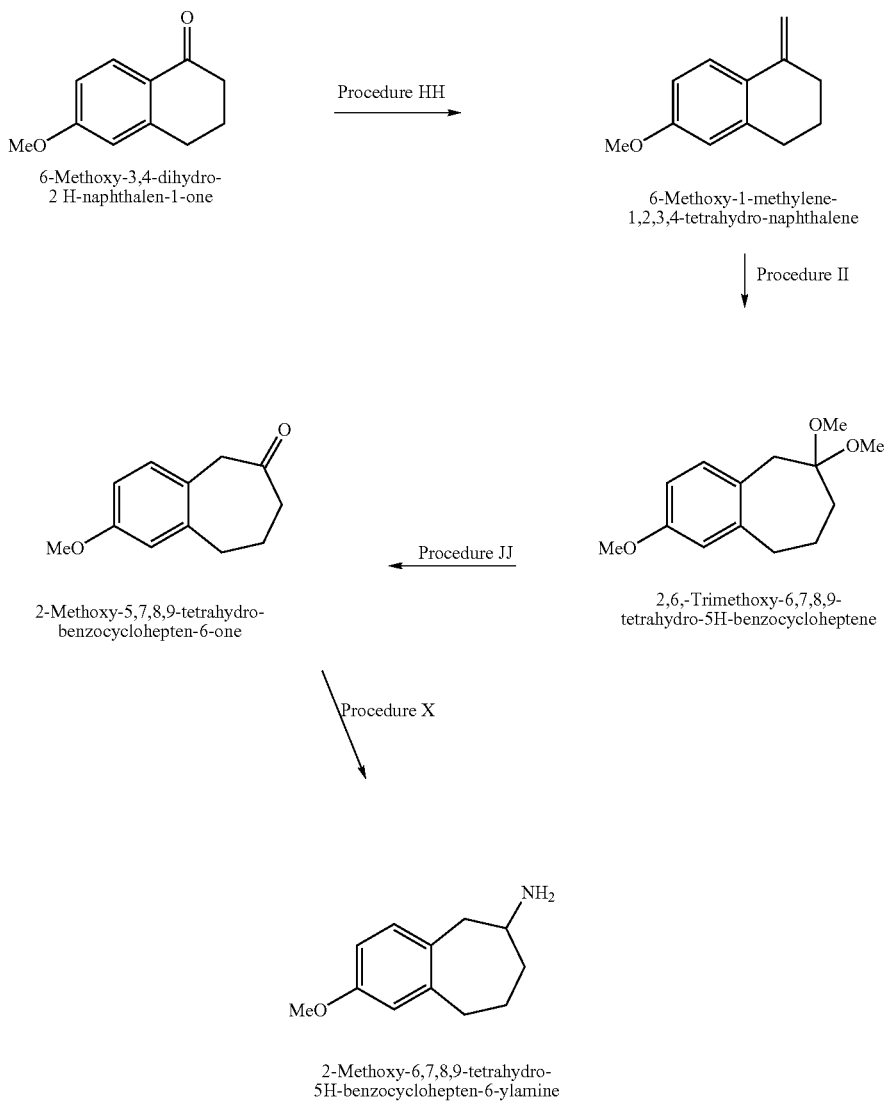

was evaporated and the residue was chromatographed (5–10% ethyl ether in hexanes) to give 0.61 g of 2,6,6-trimethoxy-6,7,8,9-tetrahydro-5H-benzocycloheptene.

Procedure HH

Tebbe's reagent (1 M in toluene, 5.3 mL, Aldrich, U.S.A.) was added dropwise to an ice-cold solution of 6-methoxy-3,4-dihydro-2H-naphthalen-1-one (0.92 g) in 8 mL of tetrahydrofuran. After stirring the mixture for 1.5 h at 0° C., 30 mL of ethyl ether was added followed by the dropwise addition of 0.1 M sodium hydroxide until gas evolution ceased. The resulting mixture was filtered through celite and the volatile material was evaporated. Silica gel chromatography of the residue (0.1% triethylamine, 2% ethyl ether in hexanes) gave 0.66 g of a colorless oil. NMR analysis indicates that the material was 66–75% pure.

Procedure JJ

A solution of 2,6,6-trimethoxy-6,7,8,9-tetrahydro-5H-benzocycloheptene (387 mg) and p-toluenesulfonic acid monohydrate (31 mg) was stirred in 5 mL of 1:1 water: acetone. The mixture was diluted with 50 mL of dichloromethane and 50 mL of saturated sodium hydrogen carbonate. The aqueous layer was re-extracted with 50 mL more dichloromethane and the combined organics were dried over sodium sulfate. Evaporation of the solvent gave 250 mg of 2-methoxy-5,7,8,9-tetrahydro-benzocyclohepten-6-one, which was converted to 2-methoxy-6,7,8,9-tetrahydro-5H-benzocyclohepten-6-ylamine by using Procedure X.

Procedure MM—Synthesis of (1H-indol-3-yl)methylamine.

Lithium aluminum hydride (100 mg) was added to a solution of 1H-indole-3-carbonitrile (100 mg) in 15 mL of

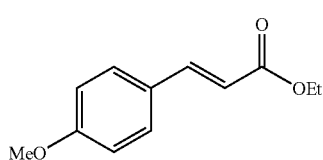

3-(4-Methoxyphenyl)
acrylic acid ethyl ester

Procedure KK →

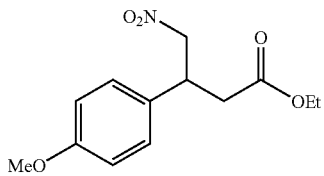

3-(4-Methoxyphenyl)-4-nitro-
butyric acid ethyl ester

↓ Procedure LL

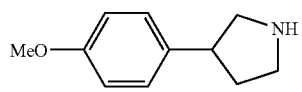

3-(4-Methoxyphenyl)-
pyrrolidine

← Procedure H

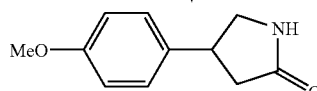

4-(4-Methoxyphenyl)-
pyrrolidin-2-one

Procedure KK

A solution of 3-(4-methoxy-phenyl)acrylic acid ethyl ester (1.0 g) and tetramethyl-guanidine (125 µL) was stirred for 24 h at 70° C. in 2.5 mL nitromethane. The solvent was evaporated and the resulting residue was partitioned in 50 mL 1 N hydrochloric acid and 50 mL ethyl ether. The ethyl ether phase was collected and washed with 50 mL 1 N hydrochloric acid. The ether phase was dried over sodium sulfate and the solvent was evaporated to furnish 1.15 g of 3-(4-methoxyphenyl)-4-nitrobutyric acid ethyl ester.

Procedure LL

A solution of 3-(4-methoxyphenyl)-4-nitrobutyric acid ethyl ester (1.15 g) in 30 mL of methyl alcohol was sparged with nitrogen. Raney nickel 2800 (0.6 mL) was added and the solution was saturated with hydrogen. The suspension was stirred at 60° C. for 7 h under 1 atm of hydrogen. The mixture was cooled, sparged with nitrogen, and filtered through celite. The filtrate was evaporated and the residue was refluxed for 24 h in ethanol. The solvent was evaporated and chromatography (1 to 3% methyl alcohol in dichloromethane) gave 250 mg of 4-(4-methoxyphenyl)pyrrolidin-2-one. The pyrrolidinone was reduced to the 3-(4-methoxyphenyl)-pyrrolidine by Procedure H.

Commercially unavailable tryptamines used in the present invention can be prepared by one of the following procedures.

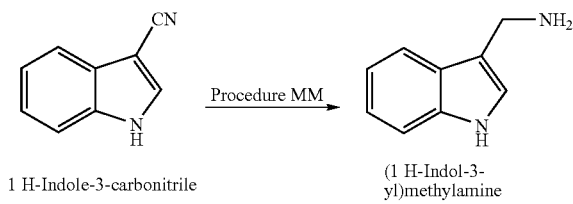

1H-Indole-3-carbonitrile

Procedure MM →

(1H-Indol-3-
yl)methylamine

2:1 dioxane:tetrahydrofuran. The mixture was refluxed for 0.5 h, then cooled to 0 C and quenched by the sequential addition of 0.1 mL water, 0.1 mL 3 N sodium hydroxide, and 0.3 mL more water. After the mixture was stirred for 15 min at rt, the aluminum salts were removed by filtration and the solvent was evaporated to give 56 mg of C-(1H-indol-3-yl)methylamine.

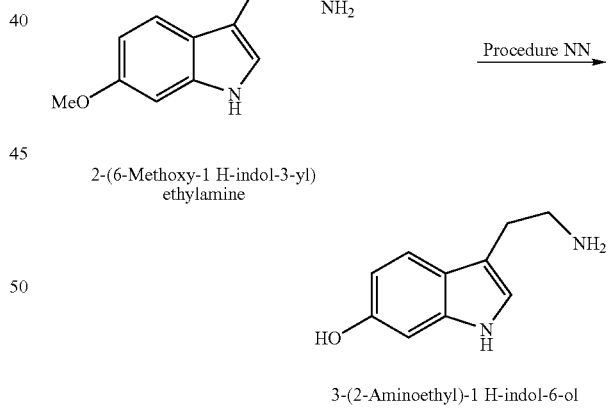

2-(6-Methoxy-1H-indol-3-yl)
ethylamine

Procedure NN →

3-(2-Aminoethyl)-1H-indol-6-ol

Procedure NN

Diisobutylaluminum hydride (1 M in toluene, 15 mL) was slowly added to a suspension of 2-(6-methoxy-1H-indol-3-yl)ethylamine (250 mg) in 20 mL of toluene. The resulting clear solution was refluxed for 10 h, then cooled to 0° C. and quenched by the careful addition of 20 mL of 1:1 methyl alcohol:water. The mixture was stirred for 15 min at rt and filtered to remove the precipitated aluminum salts. The solvent was evaporated to yield 158 mg of 3-(2-aminoethyl)-1H-indol-6-ol.

Most of the tetrahydro-1H-β-carbolines used in Procedure A—Step 3 and Procedure B—Step 5 were obtained by the Pictet-Spengler cyclization of the corresponding tryptamine. Four examples of carboline syntheses are shown below.

Procedure QQ—Pictet-Spengler Cyclization of Tryptamines with Trifluoroacetaldehyde Ethyl Hemiacetal.

A mixture of 3-(2-amino-ethyl)-1H-indol-5-ol hydrochloride (0.5 g), trifluoroacetaldehyde ethyl hemiacetal (0.35

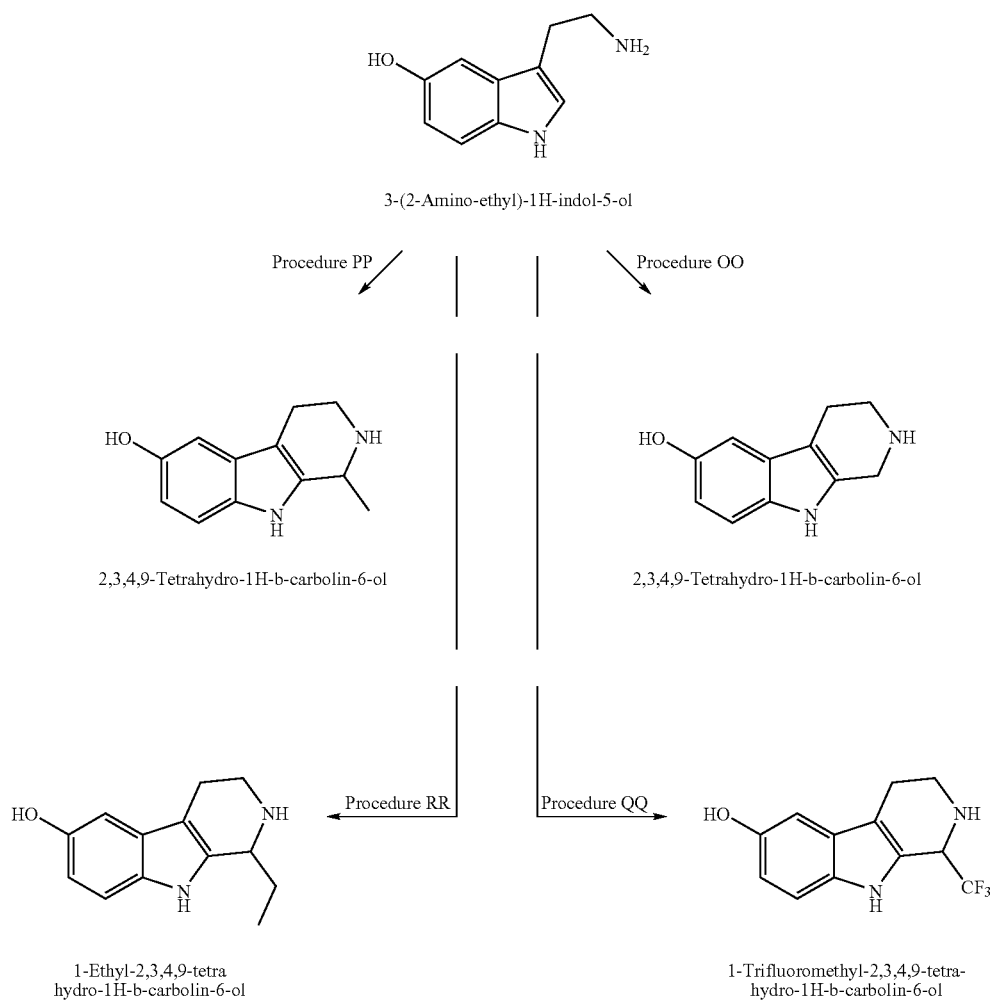

Procedure OO—Pictet-Spengler Cyclization of Tryptamines with Formaldehyde.

To a solution of 3-(2-amino-ethyl)-1H-indol-5-ol hydrochloride (10.0 g) in 450 mL of absolute ethanol was added 1.6 g of paraformaldehyde and 5.4 mL of glacial acetic acid. The mixture was heated to reflux for 1.5 h then allowed to cool to rt. The white precipitate so formed was collected by filtration and dried under vacuum to yield 5.9 g of 2,3,4,9-tetrahydro-1H-β-carbolin-6-ol hydrochloride.

Procedure PP—Pictet-Spengler Cyclization of Tryptamines with Acetaldehyde.

Acetic acid was added dropwise to a solution of 3-(2-amino-ethyl)-1H-indol-5-ol hydrochloride (200 mg) in 7 mL of methanol until the pH=4. Acetaldehyde (0.2 mL) was added and the mixture was heated at 75° C. in a sealed tube for 1 h. The tube was cooled to rt and unsealed. The solvent was evaporated yielding 160 mg of 2,3,4,9-tetrahydro-1H-β-carbolin-6-ol.

mL), acetic acid (0.32 mL) and ethanol (22.5 mL) was heated at reflux for 16 h. The solvent and excess reagents were evaporated to dryness under vacuum. The residue was washed with diethyl ether to afford 1-trifluoromethyl-2,3,4,9-tetrahydro-1H-β-carbolin-6-ol hydrochloride (0.5 g).

Procedure RR—Pictet-Spengler Cyclization of Tryptamines with Propionaldehyde.

Acetic acid was added dropwise to a solution of 3-(2-amino-ethyl)-1H-indol-5-ol hydrochloride (200 mg) in 7 mL methanol until the pH=4. Propionaldehyde (0.2 mL) was added and the mixture was heated at 75° C. in a sealed tube for 1 h. The tube was cooled to rt and unsealed. The solvent was evaporated to yield 190 mg of 2,3,4,9-tetrahydro-1H-β-carbolin-6-ol.

Some carbolines were prepared from custom synthesized intermediates. For examples, 6-methoxy-5-methyl-2,3,4,9-tetrahydro-1H-β-carboline, 9-methyl-6-triisopropylsilanyloxy-2,3,4,9-tetrahydro-1H-β-carboline, and 3-methyl-2,3,4,9-tetrahydro-1H-β-carbolin-6-ol were prepared by the following procedures.

was heated to reflux until it was clear. The solution was cooled to rt and a solution of 5-methoxy-4-methyl-indole (1.0 g) in 25 mL of ethanol was added. The reaction was

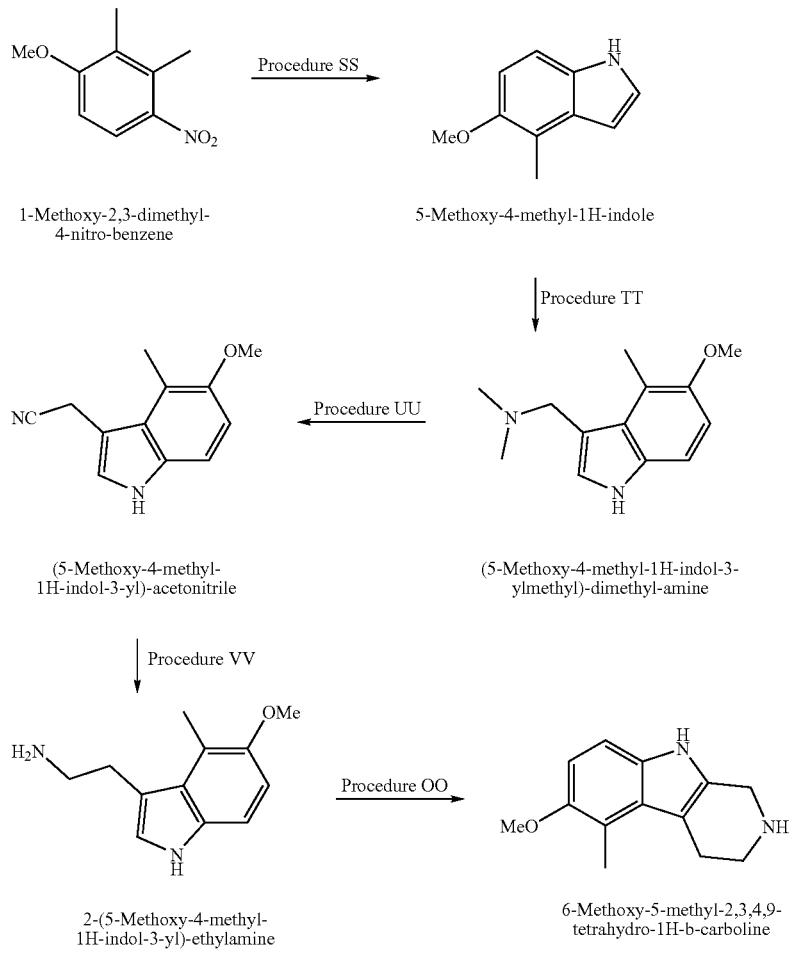

Procedure SS—Synthesis of 5-Methoxy-4-methyl-1H-indole.

A solution of 1-methoxy-2,3-dimethyl-4-nitro-benzene (5.0 g), N,N-dimethylformamide dimethylacetal (7.4 mL) and triethylamine (0.10 mL) in 25 mL of N,N-dimethylformamide was heated to reflux for 3 days under nitrogen. The volatiles were removed in vacuo and the resulting residue was dissolved in 40 mL of a 1:1 mixture of methanol and tetrahydrofuran. Raney nickel (50% slurry in water, 1 mL) was added to the solution, then hydrazine hydrate (2.7 mL) was added dropwise and the mixture was stirred for 40 min under nitrogen. The reaction mixture was filtered through a bed of celite and the filtrate was reduced in vacuo. The product was purified by column chromatography (30% ethyl acetate in hexanes) to yield 1.5 g of pure 5-methoxy-4-methyl-indole.

Procedure TT—Synthesis of (5-Methoxy-4-methyl-1H-indol-3-ylmethyl)dimethylamine.

Acetic acid (0.39 mL) and dimethylamine (0.85 mL of a 40% aqueous solution) were added to a suspension of paraformaldehyde (0.21 g) in 25 mL ethanol. The mixture heated to reflux for 3 h. The volatiles were removed in vacuo to yield (5-methoxy-4-methyl-1H-indol-3-ylmethyl)-dimethylamine (1.0 g).

Procedure UU—Synthesis of (5-Methoxy-4-methyl-1H-indol-3-yl)acetonitrile.

To a solution of potassium cyanide (0.74 g) in 20 mL water was added a solution of (5-methoxy-4-methyl-1H-indol-3-ylmethyl)dimethylamine (0.5 g) in 20 mL of N,N-dimethylformamide. The solution was heated to reflux for 40 min, cooled to rt, and 40 mL of ice water was added. The aqueous layer was extracted with three portions of toluene, and the combined toluene layers were washed with water and brine. The solvent was removed in vacuo and the product purified by column chromatography dichloromethane) as the mobile phase to yield (5-methoxy-4-methyl-1H-indol-3-yl)-acetonitrile (0.40 g).

Procedure VV—Synthesis of 2-(5-Methoxy-4-methyl-1H-indol-3-yl)-ethylamine.

A solution of (5-methoxy-4-methyl-1H-indol-3-yl)-acetonitrile (0.5 g) in 24 mL of diethyl ether was added dropwise to a suspension of lithium aluminum hydride (0.68 g) in 24 mL of diethyl ether. The mixture was heated to reflux for 3 h. The reaction was allowed to cool to rt, then cooled to 0° C. in an ice bath, and quenched by the dropwise, sequential addition of 0.75 mL water, 0.75 mL of 15% sodium hydroxide, and 2.25 mL of water. The white residue that formed was filtered off and washed with diethyl ether and the combined filtrate was reduced in vacuo. The product was purified by semi-preparative HPLC to yield the trifluoroacetate salt of 5-methoxy-4-methyl-tryptamine (487 mg). This material was cyclized to the 6-methoxy-5-methyl-2,3,4,9-tetrahydro-1H-β-carboline by Procedure OO.

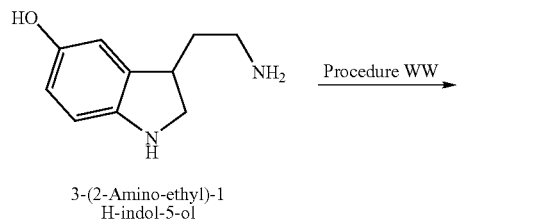

3-(2-Amino-ethyl)-1H-indol-5-ol

Procedure WW

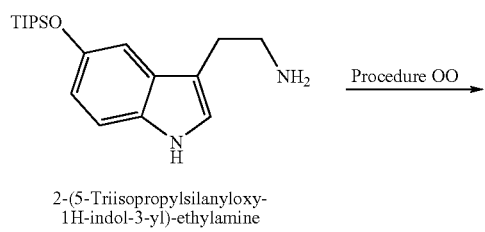

2-(5-Triisopropylsilanyloxy-1H-indol-3-yl)-ethylamine

Procedure OO

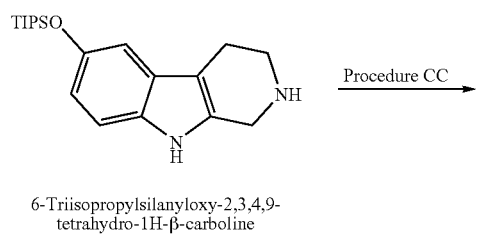

6-Triisopropylsilanyloxy-2,3,4,9-tetrahydro-1H-β-carboline

Procedure CC

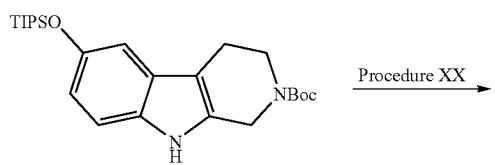

6-Triisopropylsilanyloxy-1,3,4,9-tetrahydro-β-carboline-2-carboxylic acid tert-butyl ester Procedure XX

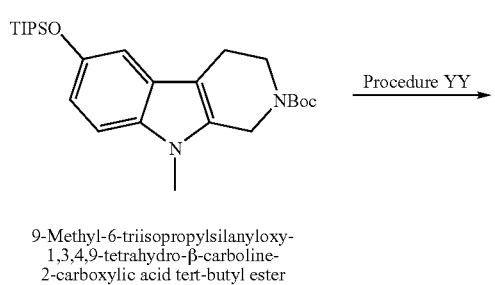

9-Methyl-6-triisopropylsilanyloxy-1,3,4,9-tetrahydro-β-carboline-2-carboxylic acid tert-butyl ester Procedure YY -continued

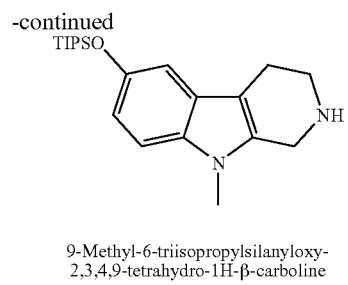

9-Methyl-6-triisopropylsilanyloxy-2,3,4,9-tetrahydro-1H-β-carboline

Procedure WW—Synthesis of 2-(5-triisopropylsilanyloxy-1H-indol-3-yl)-ethylamine

A solution of 3-(2-amino-ethyl)-1H-indol-5-ol (3.0 g), imidazole (9.6 g), and triisopropylsilyl chloride (4.5 mL) was stirred in 20 mL N,N-dimethylformamide for 6 h. The solution was diluted with 100 mL of ethyl acetate and washed with 100 mL of sodium carbonate and 100 mL of saturated sodium chloride (3 times). The organic phase was dried over sodium sulfate and the solvent was evaporated. Silica gel chromatography (2% methyl alcohol in dichloromethane) gave 2-(5-triisopropylsilanyloxy-1H-indol-3-yl)-ethylamine (2.6 g). This compound was cyclized with formaldehyde by Procedure OO to afford 6-triisopropylsilanyloxy-2,3,4,9-tetrahydro-1H-β-carboline, which was protected with tert-butoxycarbonyl group by Procedure CC to give 6-triisopropylsilanyloxy-1,3,4,9-tetrahydro-β-carboline-2-carboxylic acid tert-butyl ester.

Procedure XX—Synthesis of 9-methyl-6-triisopropylsilanyloxy-1,3,4,9-tetrahydro-β-carboline-2-carboxylic acid tert-butyl ester A solution of 6-triisopropylsilanyloxy-1,3,4,9-tetrahydro-β-carboline-2-carboxylic acid tert-butyl ester (175 mg, 0.39 mmol) in 3 mL of ethyl ether was added to a vigorously stirring solution of potassium tert-butoxide (263 mg) and 18-crown-6 (16 mg) in 10 mL ethyl ether. After 10 min, iodomethane (73 uL) in 0.5 mL of ethyl ether was added to the indole solution and the resulting mixture was stirred for 2 h. The solids were removed by filtration and the solvent was evaporated. Silica gel chromatography (10% ethyl acetate in hexanes) gave 9-methyl-6-triisopropylsilanyloxy-1,3,4,9-tetrahydro-β-carboline-2-carboxylic acid tert-butyl ester (75 mg).

Procedure YY—Synthesis of 9-methyl-6-triisopropylsilanyloxy-2,3,4,9-tetrahydro-1H-β-carboline trifluoroacetate A solution of 9-methyl-6-triisopropylsilanyloxy-1,3,4,9-tetrahydro-β-carboline-2-carboxylic acid tert-butyl ester (175 mg) and 0.5 mL of trifluoroacetic acid in 3 mL dichloromethane was stirred for 4 h. The solvent was removed to afford 9-methyl-6-triisopropylsilanyloxy-2,3,4,9-tetrahydro-1H-β-carboline trifluoroacetate (125 mg).

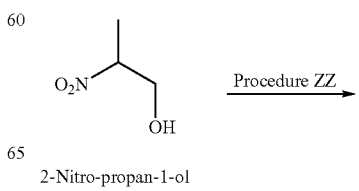

2-Nitro-propan-1-ol

Procedure ZZ

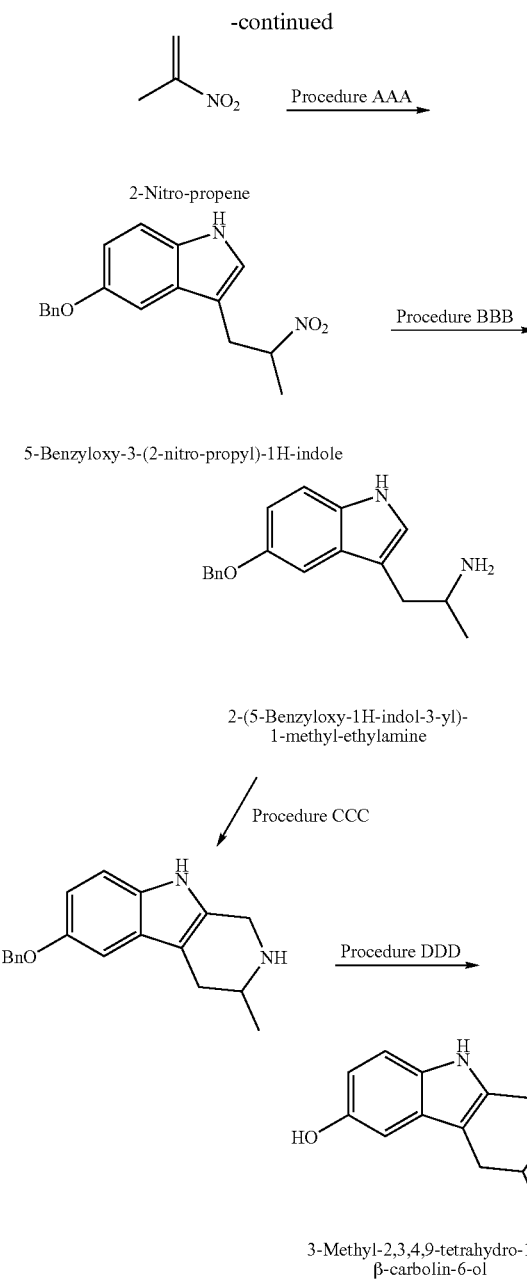

raphy (20% EtOAc/hexanes) to afford 5-benzyloxy-3-(2-nitro-propyl)-1H-indole (550 mg).

Procedure BBB

To a stirred suspension of lithium aluminum hydride (700 mg) in diethyl ether (25 mL) was slowly added a solution of 5-benzyloxy-3-(2-nitro-propyl)-1H-indole (650 mg) in diethyl ether (10 mL). The mixture was refluxed for 2 h. After cooling to rt, the reaction was quenched sequentially with 0.7 mL water, 0.7 mL 3 M aqueous sodium hydroxide, followed by 1.4 mL of water. The mixture was stirred at rt for 30 min and filtered. The filtrate was evaporated to afford 2-(5-benzyloxy-1H-indol-3-yl)-1-methyl-ethylamine (300 mg).

Procedure CCC

A mixture of 2-(5-benzyloxy-1H-indol-3-yl)-1-methyl-ethylamine (58 mg, 0.21 mmol), 37% formaldehyde (17 uL, 0.23 mmol) and ethanol (2 ml) was heated in a sealed tube at 80° C. for 2 h. The mixture was cooled to rt and acetic acid (60.6 uL, 1.05 mmol) was added. The mixture was heated again in a sealed tube at 80° C. for 5 h. Evaporation of volatiles yielded 6-benzyloxy-3-methyl-2,3,4,9-tetrahydro-1H-β-carboline (40 mg).

Procedure DDD

A solution of 6-benzyloxy-3-methyl-2,3,4,9-tetrahydro-1H-β-carboline (60 mg) in ethanol (4 mL) was added to a suspension of 10% Pd/C (100 mg) in ethanol (10 mL). The mixture was stirred at rt for 16 h under an atmosphere of hydrogen. The mixture was filtered through celite and evaporation of the filtrate yielded 3-methyl-2,3,4,9-tetrahydro-1H-β-carbolin-6-ol (30 mg).

Some tetrahydroisoquinolines in the present invention were prepared by the Bischler-Napieralski synthesis. This procedure is exemplified by the synthesis of 1-methyl-1,2,3,4-tetrahydro-isoquinolin-7-ol.

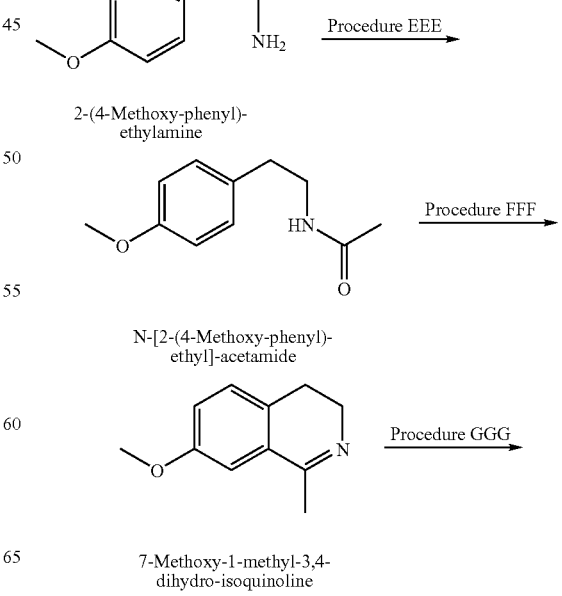

Procedure ZZ

2-Nitro-1-propanol (5 g) and phthalic anhydride (14.1 g) were combined in a round bottom flask equipped with a distillation apparatus. The reactants were heated until a homogeneous solution was formed and then the pale-green product was gently distilled and any water that co-distilled was removed with a pipet after the distillation. 2-Nitro-propene (~1.1 g) was obtained and was store at 0° C. as a 10% benzene solution.

Procedure AAA

To a stirred 0.5 M benzene solution of 5-benzyloxy-1H-indole (6 mL) was added 2-nitro-propene (5.2 mL of the 10% benzene solution). The reaction was heated at reflux under a nitrogen atmosphere overnight. The volatiles were removed and residue was purified by silica gel chromatog-

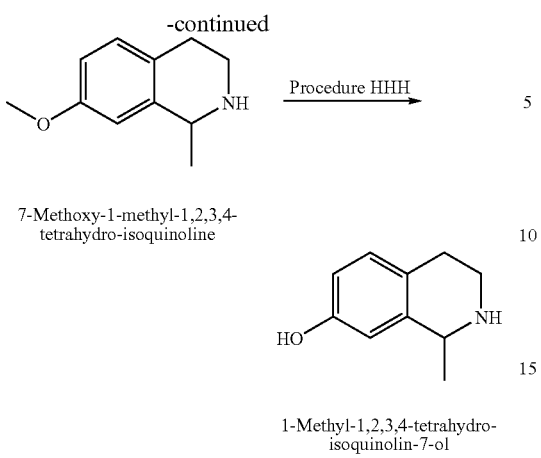

7-Methoxy-1-methyl-1,2,3,4-
tetrahydro-isoquinoline

Procedure HHH →

1-Methyl-1,2,3,4-tetrahydro-
isoquinolin-7-ol

Procedure EEE

To a mixture of (4-methoxy-phenyl)-ethylamine (10 g, Aldrich, U.S.A.) and triethylamine (10.1 mL) in dichloromethane (200 mL) was added acetic anhydride (7.4 g). The mixture was stirred at rt for 3 h and was washed successively with hydrochloric acid (1 M, 100 mL), 10% aqueous potassium carbonate (100 mL) and brine (100 mL). The dichloromethane layer was dried over sodium sulfate and filtered. The filtrate was evaporated to afford N-[2-(4-methoxy-phenyl)-ethyl]-acetamide (13.0 g).

Procedure FFF

Phosphorus oxychloride (22.5 mL) was added to a solution of N-[2-(4-methoxy-phenyl)-ethyl]-acetamide (6.5 g) in acetonitrile (200 mL). The mixture was heated at 120° C. in a sealed tube for 16 h. The solvent was evaporated. The residue was dissolved in dichloromethane (200 mL) and washed with aqueous sodium bicarbonate (saturated, 100 mL) and brine (100 mL). The dichloromethane layer was dried over sodium sulfate, filtered and evaporated. The crude product was purified by column chromatography (5% methanol in dichloromethane) to afford 7-methoxy-1-methyl-3,4-dihydro-isoquinoline (2.67 g).

Procedure GGG

Sodium cyanoborohydride (0.43 g) was added to a solution of 7-methoxy-1-methyl-3,4-dihydro-isoquinoline (2.67 g) in methanol (41 mL). The mixture was stirred at rt for 20 min. Aqueous sodium bicarbonate (saturated, 10 mL) was added to quench the excess hydride reagent. The methanol was evaporated under vacuum and the aqueous solution was diluted with sodium bicarbonate (saturated, 30 mL) and extracted with dichloromethane (2×30 mL). The combined organic layers were dried over sodium sulfate, filtered and evaporated to afford 7-methoxy-1-methyl-1,2,3,4-tetrahydro-isoquinoline (2.55 g).

Procedure HHH

Hydrobromic acid (48%, 46 mL) was added to the 7-methoxy-1-methyl-1,2,3,4-tetrahydro-isoquinoline (2.55 g) and the resulting mixture was heated at reflux for 16 h. Evaporation of the hydrobromic acid, followed by trituration with ethyl acetate (3×) afforded 1-methyl-1,2,3,4-tetrahydro-isoquinolin-7-ol hydrogen bromide (3.04 g).

Similarly, 1-ethyl-1,2,3,4-tetrahydro-isoquinolin-7-ol was prepared by the above procedures by replacing the acetic anhydride in Procedure EEE with propionyl chloride. 1-Methyl-1,2,3,4-tetrahydro-isoquinoline-6,7-diol and 1,6-dimethyl-1,2,3,4-tetrahydro-isoquinolin-7-ol were prepared by replacing the (4-methoxy-phenyl)-ethylamine in procedure EEE with 3,4-dimethoxyphenylethylamine and 3-methyl-4-methoxyphenylethylamine, respectively.

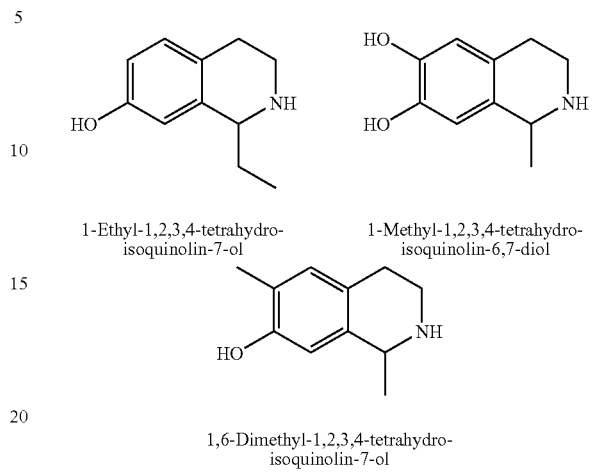

1-Ethyl-1,2,3,4-tetrahydro-
isoquinolin-7-ol

1-Methyl-1,2,3,4-tetrahydro-
isoquinolin-6,7-diol 1,6-Dimethyl-1,2,3,4-tetrahydro-
isoquinolin-7-ol Some tetrahydroisoquinolines in the current invention were prepared by the Pictet-Spengler synthesis (J. Am. Chem. Soc. 1934, 56, 1769–1771). For examples, 6-methoxy-1,2,3,4-tetrahydro-isoquinoline and 6,7-dimethoxy-1,2,3,4-tetrahydro-isoquinoline were prepared by the condensation of formaldehyde with 3-methoxyphenethylamine and 3,4-dimethoxyphenethylamine, respectively. These compounds could be converted to 1,2,3,4-tetrahydro-isoquinolin-6-ol and 1,2,3,4-tetrahydro-isoquinoline-6,7-diol by Procedure HHH.

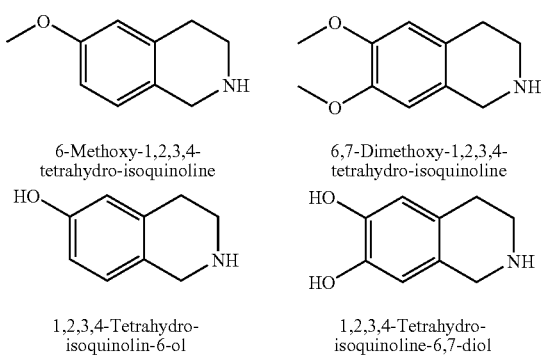

6-Methoxy-1,2,3,4-
tetrahydro-isoquinoline 6,7-Dimethoxy-1,2,3,4-
tetrahydro-isoquinoline 1,2,3,4-Tetrahydro-
isoquinolin-6-ol 1,2,3,4-Tetrahydro-
isoquinoline-6,7-diol 7-Methoxy-1,2,3,4-tetrahydro-isoquinoline and 1,2,3,4-tetrahydro-isoquinolin-7-ol were prepared by a literature procedure (J. Med. Chem. 1987, 30, 2208–2216). 2-(4-Methoxy-phenyl)-1-methyl-ethylamine required for the preparation of 3-methyl-1,2,3,4-tetrahydro-isoquinolin-7-ol was obtained from 1-(4-methoxy-phenyl)-propan-2-one by Procedure X and was subsequently converted to the tetrahydroisoquinoline by the same literature method.

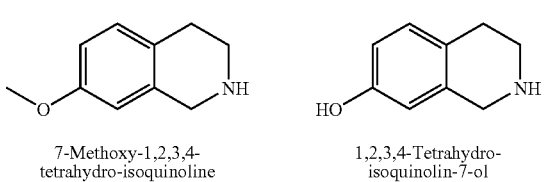

7-Methoxy-1,2,3,4-
tetrahydro-isoquinoline 1,2,3,4-Tetrahydro-
isoquinolin-7-ol

-continued

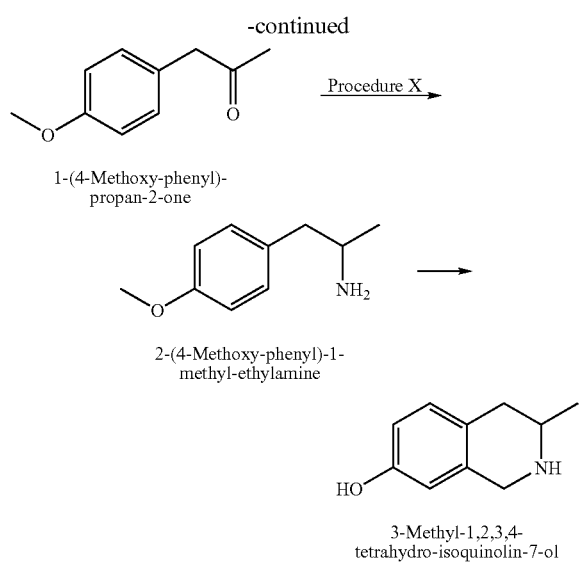

1-(4-Methoxy-phenyl)-propan-2-one

Procedure X 2-(4-Methoxy-phenyl)-1-methyl-ethylamine

3-Methyl-1,2,3,4-tetrahydro-isoquinolin-7-ol

The D- and L-3-hydroxymethyl-1,2,3,4-tetrahydro-isoquinolin-7-ol were prepared from the commercially available D- and L-Boc-7-hydroxy-1,2,3,4-tetrahydroisoquinoline-3-carboxylic acid by Procedure III, respectively.

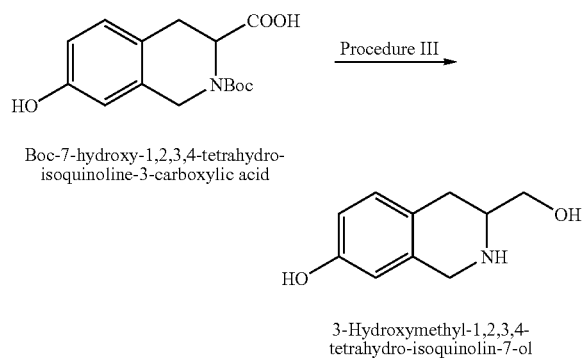

Boc-7-hydroxy-1,2,3,4-tetrahydro-isoquinoline-3-carboxylic acid

Procedure III

3-Hydroxymethyl-1,2,3,4-tetrahydro-isoquinolin-7-ol

Procedure III

A 1 M solution of borane-tetrahydrofuran complex in tetrahydrofuran (8 mL, Aldrich, U.S.A.) was added dropwise to a 0° C. solution of Boc-L-7-hydroxy-1,2,3,4-tetrahydroisoquinoline-3-carboxylic acid (1.0 g, Bachem, U.S.A.) in 8 mL tetrahydrofuran. The reaction was allowed to warm to rt and stirred for 2.5 h. The reaction was cooled to 0° C. and quenched by the dropwise addition of 8 mL of brine. The organic layer was separated and the aqueous layer was extracted twice with ethyl acetate. The organic layers were combined, washed with brine, dried over magnesium sulfate, and the solvent was removed in vacuo to give 1.0 g of a clear oil. The oil was dissolved in 10 mL of a 4 M solution of hydrogen chloride in 1,4-dioxane and allowed to stir for one hour at rt. The solvent was removed in vacuo to yield 0.65 g of L-3-hydroxymethyl-1,2,3,4-tetrahydro-isoquinolin-7-ol as an off-white powder. The D-isomer was prepared using the same synthesis and gave comparable yields.

7-Nitro-1,2,3,4-tetrahydro-isoquinoline, 1,2,3,4-tetrahydro-isoquinolin-7-ylamine and 1,2,3,4-tetrahydro-isoquinoline-7-carbonitrile were prepared by literature procedures (*J. Med. Chem.* 1999, 42, 118–124 and *J. Med. Chem.* 1997, 40, 3997–4005).

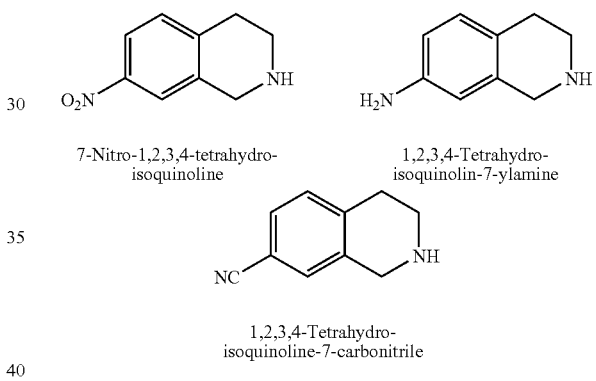

7-Nitro-1,2,3,4-tetrahydro-isoquinoline 1,2,3,4-Tetrahydro-isoquinolin-7-ylamine 1,2,3,4-Tetrahydro-isoquinoline-7-carbonitrile Other analogs were prepared from 1,2,3,4-tetrahydro-isoquinolin-7-ylamine and 1,2,3,4-tetrahydro-isoquinoline-7-carbonitrile by the following procedures.

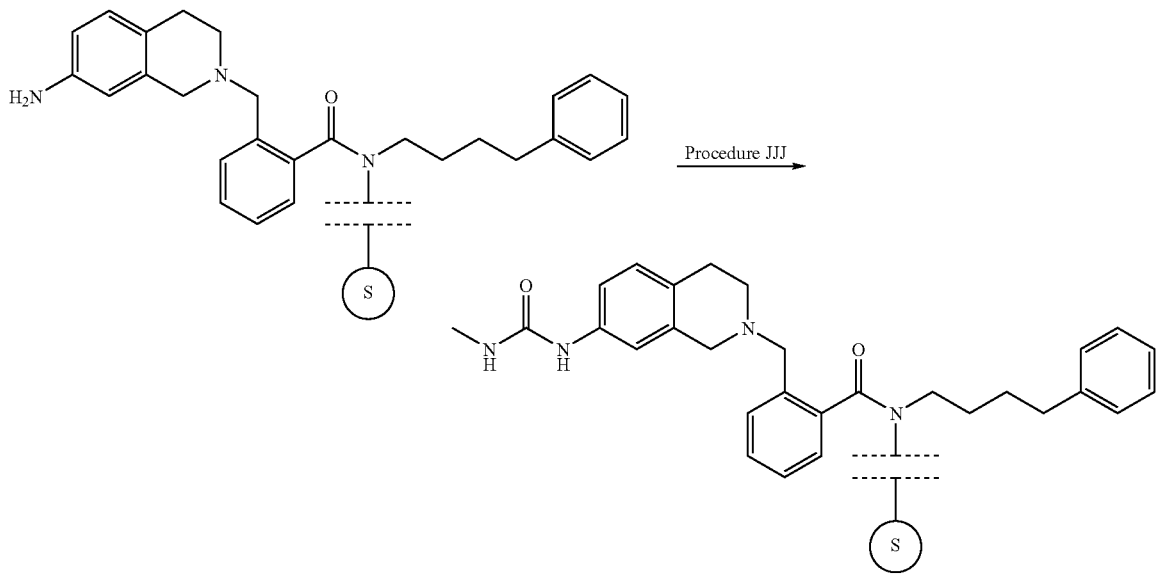

Procedure JJJ

Procedure JJJ

The resin-bound amine was prepared by Procedure A and converted to the urea by the following method: resin-bound amine (0.15 g) was suspended in dichloromethane (2 mL). Diisopropylethylamine (0.1 mL) and methylisocyanate (0.2 mL) were added. The resulting mixture was shaken at rt for 16 h. The resin was washed with dimethylformamide, methanol and dichloromethane (3× of each solvent). The resin was treated with TFA (Procedure C) to release the final product.

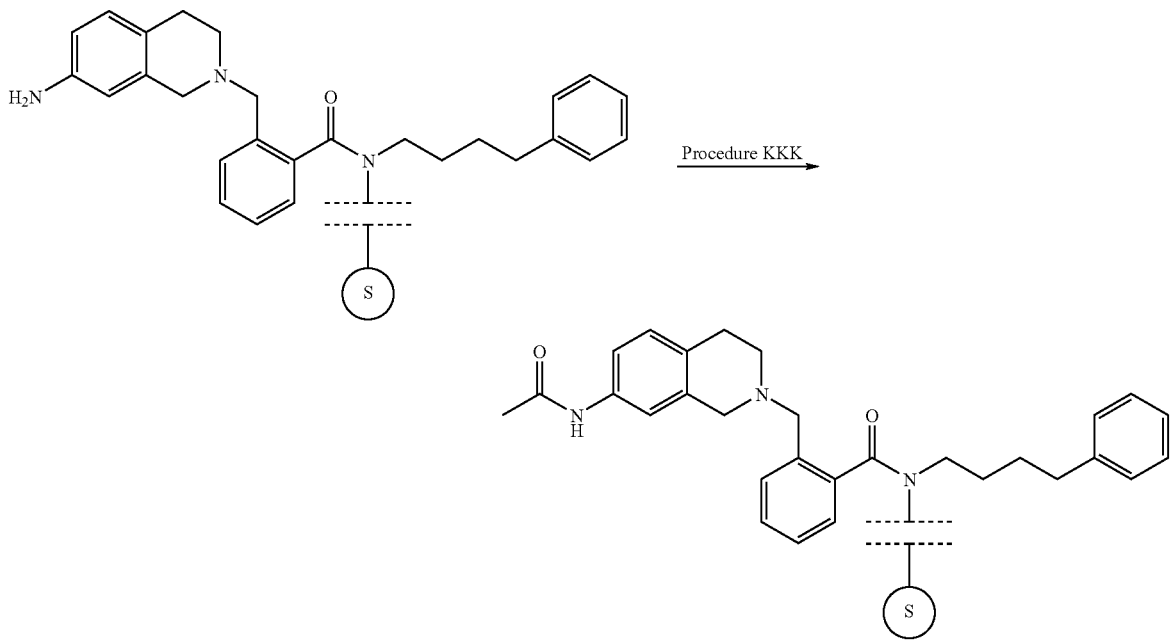

Procedure KKK

The resin-bound amine was prepared by Procedure A and converted to the acetamide by the following method: a premixed solution of acetic anhydride (47 uL) in chloroform (2 mL) was added to the resin-bound amine (0.15 g). The resulting mixture was shaken at rt for 16 h. The resin was washed with dimethylformamide, methanol and dichloromethane (3× of each solvent). The resin was treated with TFA (Procedure C) to release the final product.

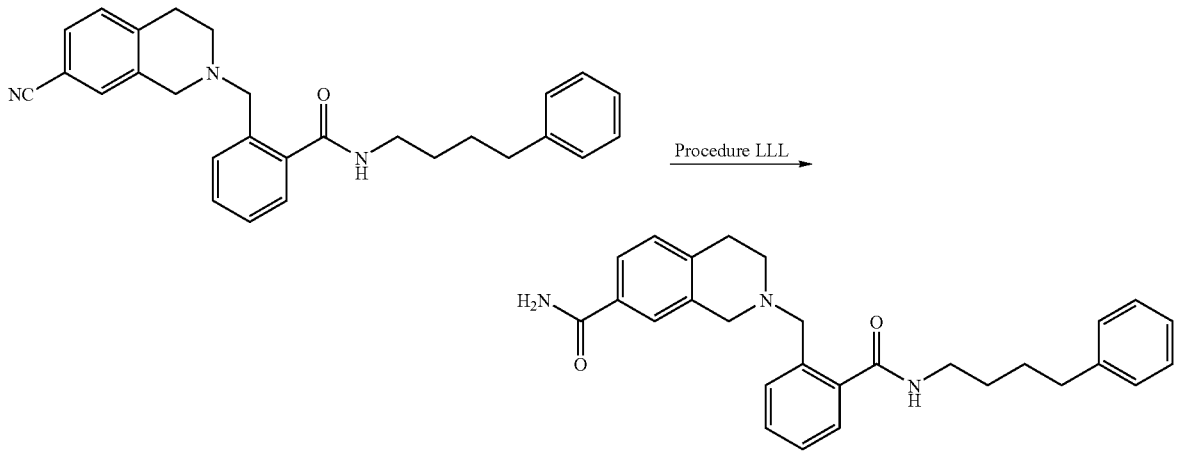

2-[2-(4-Phenylbutylcarbamoyl)benzyl]-1,2,3,4-tetrahydro-isoquinoline-7-carboxamide Procedure LLL The nitrile was prepared by Procedure A and cleaved from the resin by Procedure C. The nitrile was further converted to the amide by the following method: a premixed solution of hydrogen peroxide (28%, 1 mL), aqueous sodium hydroxide (6 M, 2 mL) and methanol (1 mL) was added to the nitrile (8.2 mg). The mixture was stirred at rt for 16 h and acidified by hydrochloric acid (2 M) to pH 1. The aqueous solution was evaporated under vacuum and the residue was purified by semi-preparative HPLC to afford 2-[2-(4-phenyl-butylcarbamoyl)-benzyl]-1,2,3,4-tetrahydro-isoquinoline-7-carboxylic acid amide (3.4 mg).

Tetrahydroisoquinolines containing sulfonamide group were prepared from 2-acetyl-1,2,3,4-tetrahydro-isoquinoline-7-sulfonyl chloride (*J. Med. Chem.* 1999, 42, 118–134) by the following procedures.

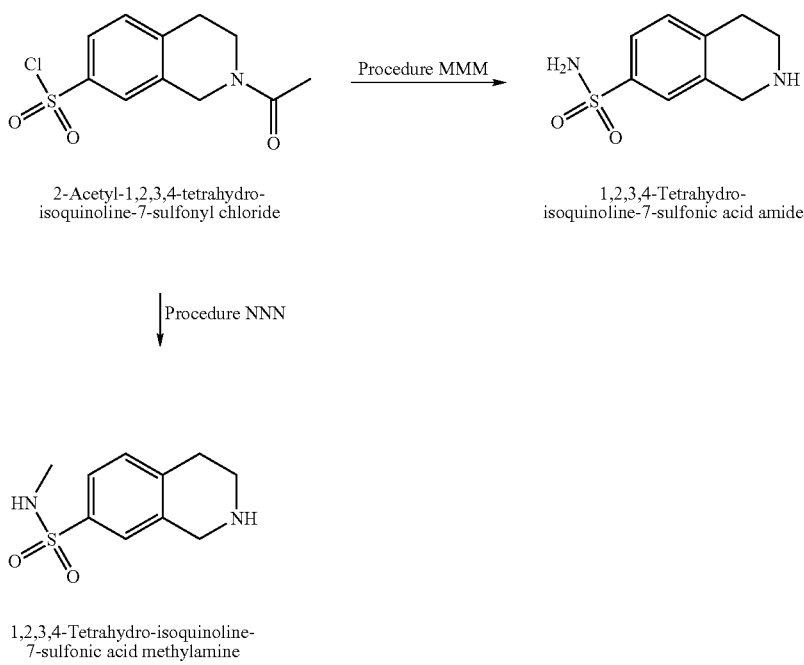

Procedure MMM

Ammonium hydroxide (conc., 20 mL) was added to 2-acetyl-1,2,3,4-tetrahydro-isoquinoline-7-sulfonyl chloride (2 g). The mixture was stirred at rt for 16 h. The ammonium hydroxide was evaporated under vacuum and hydrochloric acid (10%, 50 mL) was added to the residue. The mixture was heated at reflux for 4 h and the aqueous was evaporated under vacuum to afford 7-aminosulfonyl-1,2,3,4-tetrahydro-isoquinoline hydrochloride (1.5 g).

Procedure NNN

Methylamine in methanol (2 M, 20 mL) was added to 2-acetyl-1,2,3,4-tetrahydro-isoquinoline-7-sulfonyl chloride (2 g). The mixture was stirred at rt for 16 h. Excess methylamine and methanol were evaporated under vacuum and hydrochloric acid (10%, 30 mL) was added to the residue. The mixture was heated at reflux for 3 h and the aqueous solution was evaporated under vacuum. The residue was trituiated with ethyl acetate (2×20 mL) to afford 7-methylaminosulfonyl-1,2,3,4-tetrahydro-isoquinoline hydrochloride (1.9 g).

2,3-Dihydro-1H-isoindol-5-ol was prepared from 4-methoxy-phthalic acid dimethyl ester by the following procedures:

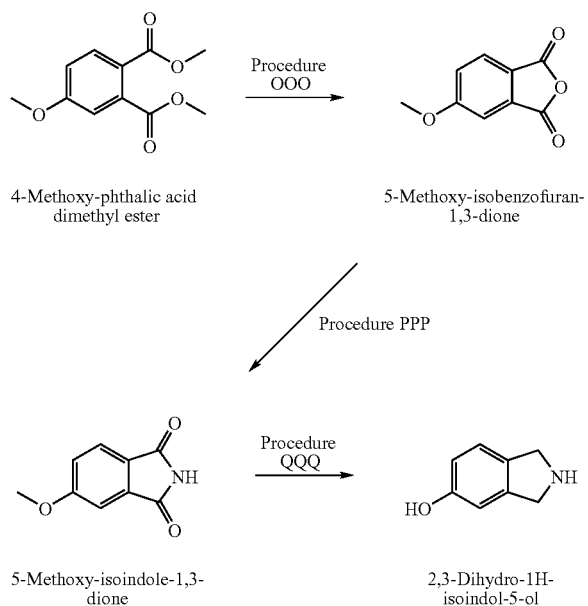

Procedure OOO

A solution of 4-methoxyphthalic acid dimethyl ester (3.1 g, Fluka, U.S.A.) in 10 mL methanol and 35 mL of a 1 M solution of aqueous sodium hydroxide was heated to reflux for 3 hours. The solution was allowed to cool to rt, acidified to pH 2 with 1 M hydrochloric acid, and extracted three times with ethyl acetate. The organic extractions were combined, dried over magnesium sulfate, and reduced in vacuo to cleanly yield 2.43 g of the corresponding diacid. The diacid (1.43 g) and 1.9 mL of acetic anhydride were dissolved in tetrahydrofuran and heated to reflux for 16 hours. The solvent was evaporated to give 5-methoxy-isobenzofuran-1,3-dione (1.25 g).

Procedure PPP

The anhydride (1.25 g) and 25 mL of formamide were heated to reflux for 5 hours. Upon cooling to rt, an off-white precipitate formed. This was filtered off and dried under vacuum to cleanly yield 5-methoxy-isoindole-1,3-dione (1.0 g).

Procedure QQQ

The 5-methoxy-isoindole-1,3-dione (0.5 g) was dissolved in 10 mL of tetrahydrofuran and cooled to 0° C. A 1 M solution of borane-tetrahydrofuran complex in tetrahydrofuran (8 mL, Aldrich, U.S.A.) was added dropwise. The mixture was heated to reflux for 5 hours, cooled to 0° C., and quenched by slow addition of methanol. To the reaction was added 2 mL of 6 M hydrochloric acid, and the mixture was refluxed for an additional hour. After cooling to 0° C., the reaction was made basic to pH≧10 with 6 M sodium hydroxide. The organic layer was separated, and the aqueous layer was extracted three times with diethyl ether. The organic layers were combined, dried over magnesium sulfate and reduced in vacuo. The product was purified by flash chromatography, using 15% methanol/dichloromethane to 100% methanol as the mobile phase. The purified yield was 0.20 g of 5-methoxy-2,3-dihydro-1H-isoindole. A solution of 5-methoxy-2,3-dihydro-1H-isoindole (0.20 g) in 48% hydrobromic acid (15 mL) was heated to reflux for 16 h. The solvent was removed in vacuo to yield 0.22 g of the hydrobromide salt of 2,3-dihydro-1H-isoindol-5-ol.

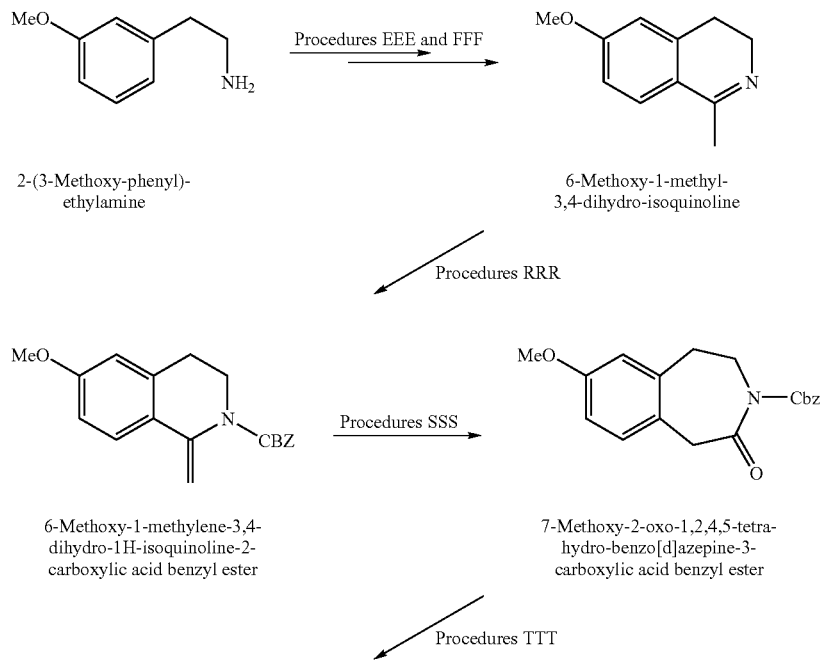

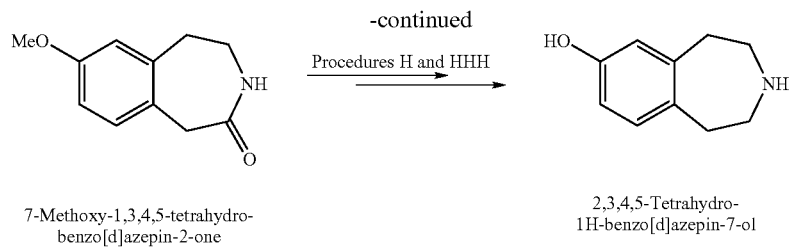

7-Methoxy-1,3,4,5-tetrahydro-benzo[d]azepin-2-one 2,3,4,5-Tetrahydro-1H-benzo[d]azepin-7-ol 2,3,4,5-Tetrahydro-1H-benzo[d]azepin-7-ol and 2,3,4,5-tetrahydro-1H-benzo[c]azepin-7-ol were prepared as shown below.

Procedure RRR

Benzyl chloroformate (0.30 mL) was added to an ice-cold solution of 6-methoxy-1-methyl-3,4-dihydroisoquinoline (0.36 g) and triethylamine (0.58 mL) in 10 mL dichloromethane. After 0.5 h, the volatile material was evaporated to furnish 0.66 g of 6-methoxy-1-methylene-3,4-dihydro-1H-isoquinoline-2-carboxylic acid benzyl ester.

Procedure SSS

To a solution of 6-methoxy-1-methylene-3,4-dihydro-1H-isoquinoline-2-carboxylic acid benzyl ester (0.66 g) in 20 mL of glacial acetic acid was added lead tetraacetate (1 g). The reaction was stirred overnight, then quenched by the addition of 2 mL of glycerol. The volatile material was evaporated and the resulting residue was partitioned between 50 mL of saturated sodium chloride and 50 mL of dichloromethane. The aqueous phase was re-extracted with 50 mL more dichloromethane and the combined extracts were dried over sodium sulfate. The volatile material was evaporated and chromatography (20% ethyl acetate in hexanes) yielded 0.20 g of 7-methoxy-2-oxo-1,2,4,5-tetrahydrobenzo[d]azepine-3-carboxylic acid benzyl ester.

Procedure TTT

A solution of 7-methoxy-2-oxo-1,2,4,5-tetrahydrobenzo[d]azepine-3-carboxylic acid benzyl ester (0.20 g) in 10 mL of 1:1 acetic acid/methyl alcohol was sparged with nitrogen. Palladium on carbon (10%, 50 mg) was added and the solution was saturated with hydrogen. The suspension was stirred for 20 h under 1 atm of hydrogen. The mixture was then sparged with nitrogen, and filtered through celite. The filtrate solvent was evaporated and chromatography (methyl alcohol in dichloromethane) gave 150 mg of 7-methoxy-1,3,4,5-tetrahydrobenzo[d]azepin-2-one.

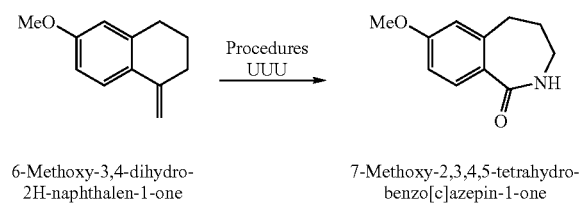

6-Methoxy-3,4-dihydro-2H-naphthalen-1-one

7-Methoxy-2,3,4,5-tetrahydro-benzo[c]azepin-1-one

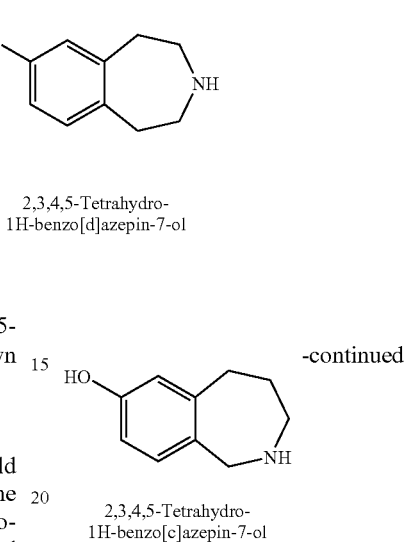

2,3,4,5-Tetrahydro-1H-benzo[c]azepin-7-ol

Procedure UUU

Sodium azide (0.37 g) was slowly added in portions to a stirring ice-cold suspension of 6-methoxy-3,4-dihydro-2H-naphthalen-1-one in 10 mL of concentrated hydrochloric acid. The mixture was allowed to slowly warm to room temperature and stirred for 20 h. The mixture was poured onto ice and carefully neutralized with solid potassium carbonate. The resulting mixture was extracted with two 50 mL aliquots of dichloromethane. The organic material was dried over sodium sulfate and the solvent was evaporated. Chromatography (ethyl acetate) gave 0.45 g of 7-methoxy-2,3,4,5-tetrahydrobenzo[c]azepine-1-one.

In some cases, elevated temperatures (~80° C.) are required to displace the resin-chloride with steric or electron-deficient amines. Two such examples are shown below:

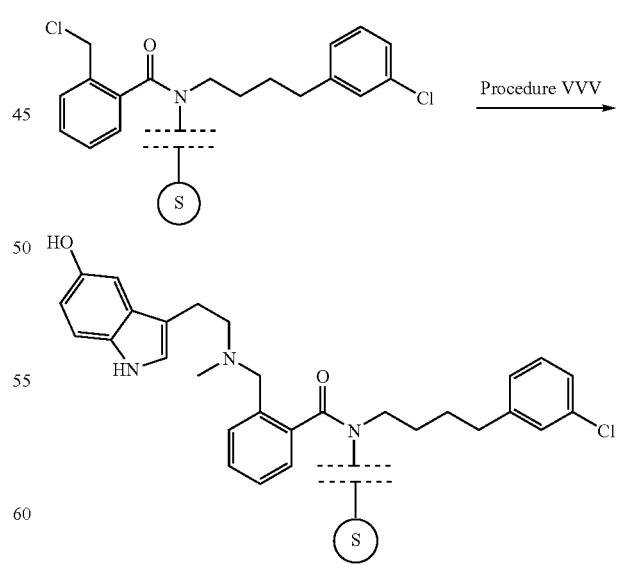

Procedure VVV

The resin-bound chloride was prepared by Procedure A and converted to the desired product by the following method: To a suspension of 0.15 g (~0.4 mmol/g) of resin-bound chloride in dimethylformamide (1 mL) was added 5-hydroxy-$N_\omega$-methyltryptamine oxalate (100 mg, Aldrich, U.S.A.), tetrabutylammonium iodide (0.11 g), followed by diisopropylethylamine (0.21 mL). The mixture was heated at 80° C. for 16 h. The vessel was drained and the resin was washed with dimethylformamide, methanol and dichloromethane (3× of each solvent). The resin was treated with TFA (Procedure D) to release the final product.

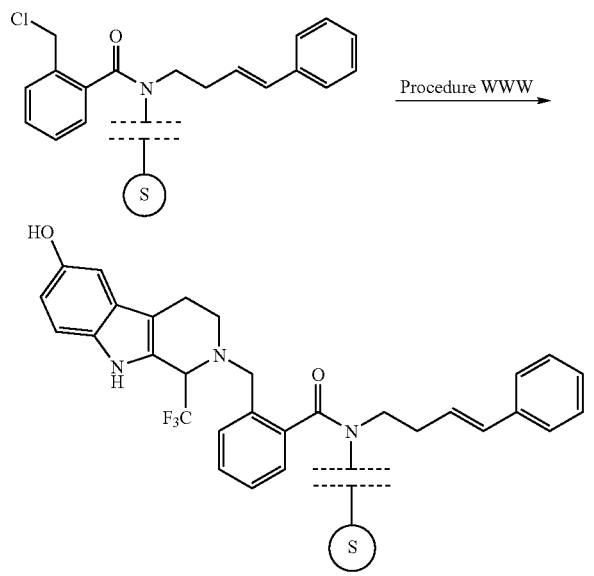

Procedure WWW

The resin bound chloride was prepared by Procedure A and converted to the desired product by the following method. A premixed solution of 1-trifluoromethyl-2,3,4,9-tetrahydro-1H-β-carbolin-6-ol hydrochloride (88 mg) and diisopropylethylamine (105 uL) in dimethylformamide (1.5 mL) was added to the resin bound chloride (0.15 g, ~0.4 mmol/g), followed by tetrabutylammonium iodide (111 mg). The mixture was heated at 80° C. for 16 h. The vessel was drained and the resin was washed with dimethylformamide, methanol and dichloromethane (3× for each solvent). The resin was treated with TFA (Procedure C) to release the final product.

Enantiomers of 2-(7-hydroxy-1-methyl-3,4-dihydro-1H-isoquinolin-2-ylmethyl)-N-(4-phenyl-but-3-enyl)-benzamide can be separated by a HPLC system equipped with a chiral semi-preparative column (Chiracel OD, 4.6×120 mm, Daicel Chemical Industrial, Ltd., U.S.A.). The isomers were eluted isocratically by a mixture of 9:1 hexanes/ispropanol.

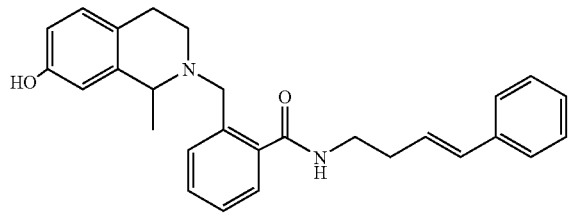

2-(7-Hydroxy-1-methyl-3,4-dihydro-1H-isoquinolin-2-ylmethyl)-N-(4-phenyl-but-3-enyl)-benzamide Anhydride Used in Procedure B—Step 1

Anhydride Used in Procedure B—Step 1

The 4,5-dichlorophthalic anhydride used in Procedure B—Step 1 was replace with one of the following commercially available anhydrides to prepare the example compounds shown in Table 2:

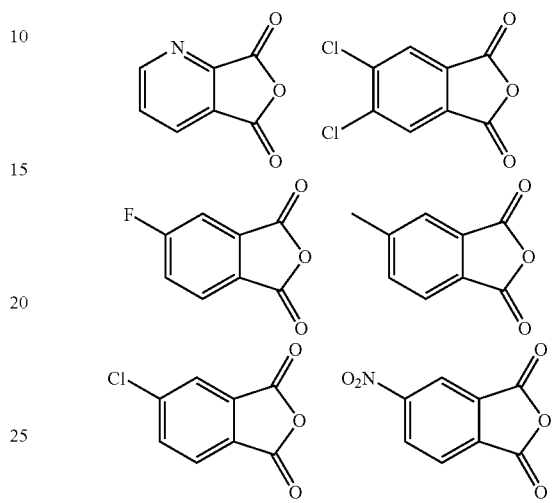

The Use of a Photo-labile Linker

A number of compounds included in the invention were acid-labile by nature. Thus, a photo-cleavable linker was employed in the synthesis of these derivatives. In these cases, a typical solid support would be Rapp Tentagel resin. The linker,

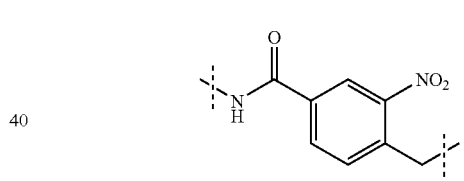

(also represented by ⋮), is a benzyl bromide that is reacted with a primary amine (e.g. 4-phenylbutylamine) to generate a resin-bound secondary amine. The amine is further elaborated via Procedures A—Step 2 and Step 3. Cleavage of the final derivative is accomplished by treatment of a suspension of the solid support in methanol containing 3% trifluoroacetic acid with light (365 nm). Representative examples are shown below.

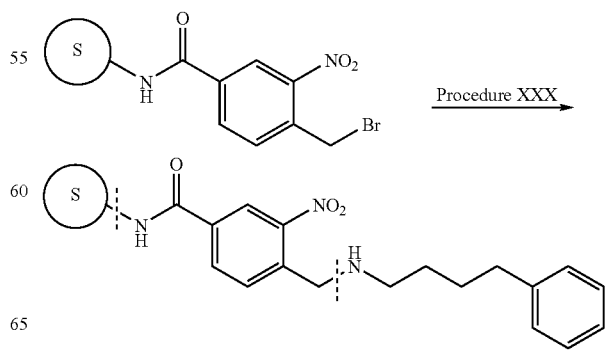

Procedure XXX

A suspension of resin-bound bromide (1.13 g, 0.6 mmol/g) was shaken in a solution of phenylbutylamine (1.1 mL), diisopropylethylamine (1.2 mL), and tetrabutylammonium iodide (0.25 g) in 10 mL of N,N-dimethylformamide for 22 h. The flask was drained and the resin was washed with three 10 mL portions of N,N-dimethylformamide, three 10 mL portions of methyl alcohol, and three 10 mL portions of dichloromethane. The resin is dried in vacuo. This resin was further modified by Procedure A—Step 2 and Step 3 to obtain the starting material for Procedure YYY.

to afford the trifluoroacetate salts. The molecular weight of the compound was confirmed by mass spectroscopy (m/z).

Inhibition of glycine transport by the compounds is determined using a recombinant Chinese hamster ovary (CHO) cell line expressing human $GlyT_2$ transporter. The pcDNA3 mammalian expression vector containing the full length hGlyT2 sequence was used to generate a stable cell line in CHO cells. Approximately 200 clones were screened for increased $^3$H-glycine uptake. One clone produced a 5–6 fold increase in glycine uptake over parental cells and was used in the assays. Assays were performed in 96-well microtiter

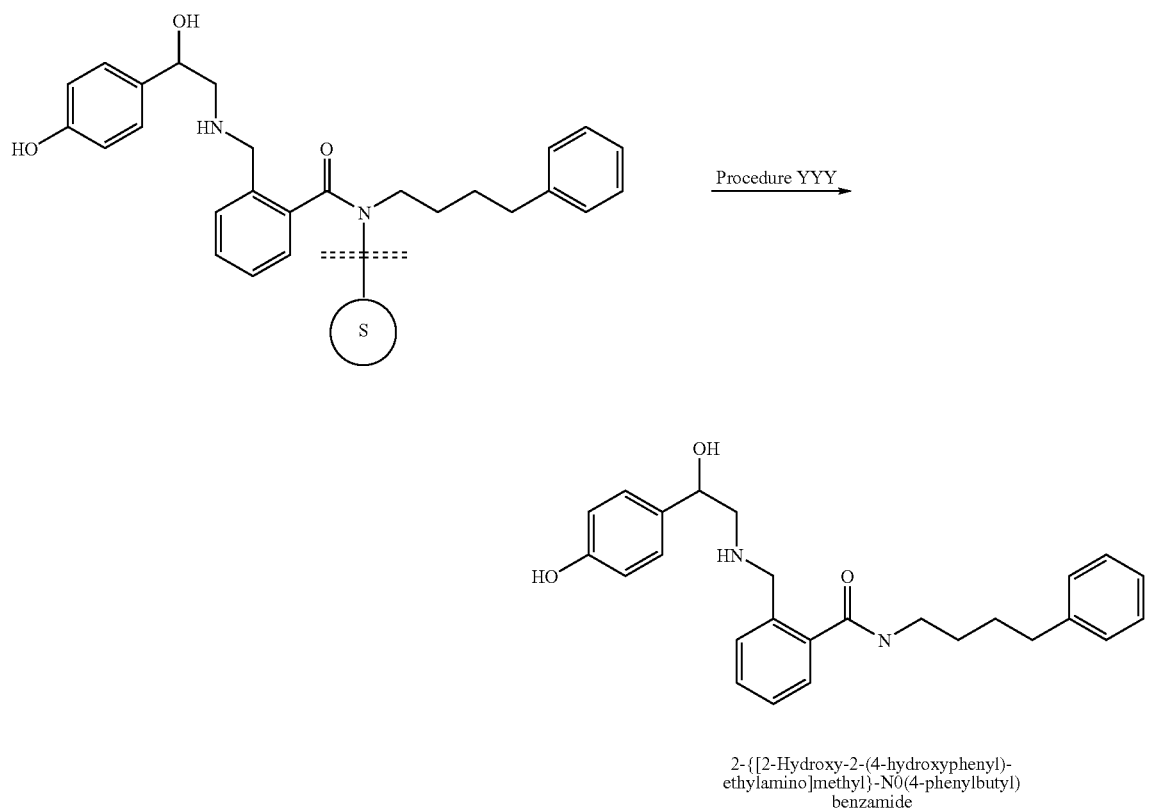

2-{[2-Hydroxy-2-(4-hydroxyphenyl)-ethylamino]methyl}-N0(4-phenylbutyl) benzamide

Procedure YYY

A stirred suspension of resin (100 mg) in 3 mL of methyl alcohol containing 3% v/v of trifluoroacetic acid was irradiated with light ((365 nm, intensity of lamp equal to 4.5 mW measured at 365 nm using a 365 nm bandpass filter with a bandwidth of +/−10 nm) at 50° C. for 3 h. The crude cleavage material was isolated by filtration and evaporation of solvent. Preparative HPLC gave 4.4 mg of 2-{[2-hydroxy-2-(4-hydroxy-phenyl)-ethylamino]-methyl}-N-(4-phenyl-butyl)-benzamide.

Table 1 illustrates several examples of compounds represented by Formula I. These compounds were synthesized using Procedure A or Procedure XXX. The compounds were cleaved from the resin by cleavage Procedures C, D, or YYY plates using adherent cells incubated in Hepes-buffered Hank's saline solution, pH 7.4 (HBSS) for 20 minutes at 37° C. The final concentration of glycine was 10 mM. Cell monolayers were washed three times with HBSS to remove excess radiolabel and glycine uptake was quantitated by liquid scintillation counting (Wallac MicroBeta). Under the above assay the compounds of the present invention were found to be potent inhibitors of human $GlyT_2$. All compounds in the tables below exhibited $IC_{50}$ values less than 10 μM. Entries in the 100 series exhibited $IC_{50}$ values less than 100 nM; entries in the 200 series exhibited $IC_{50}$ values less than 500 nM; and entries in the 300 series exhibited $IC_{50}$ values less than 1 μM.

TABLE 1

| Entry | Structure | Cleavage Procedure (Resin Cleaved in g) | Yield (mg) | m/z (M + H)+ |
|---|---|---|---|---|
| 101 | 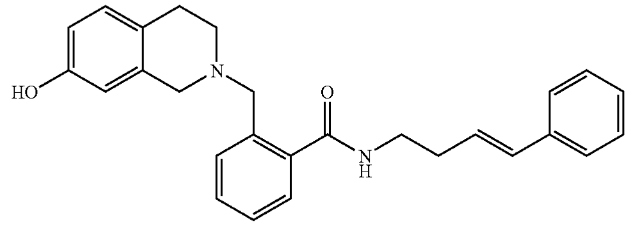 | Procedure C 0.20 g | 1.5 mg | 413 |
| 301 | 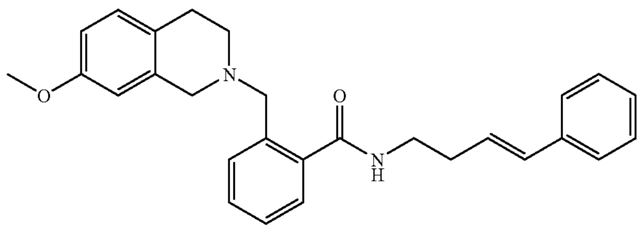 | Procedure C 0.10 g | 3.2 mg | 427 |
| 102 | 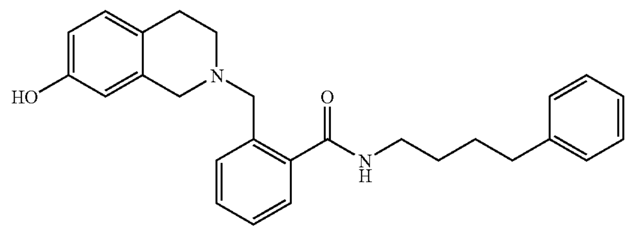 | Procedure C 0.10 g | 8.0 mg | 415 |
| 103 | 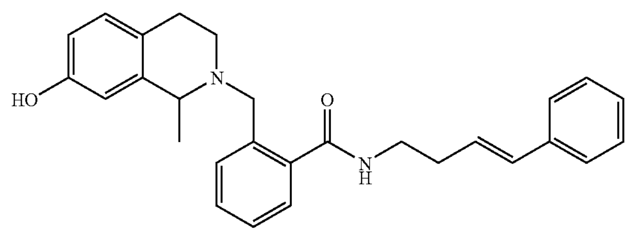 | Procedure C 0.15 g | 16 mg | 427 |
| 201 | 103-Enantiomer 1 | Procedure C 0.50 g | 7.4 mg | 427 |
| 104 | 103-Enantiomer 2 | Procedure C 0.50 g | 8.6 mg | 427 |
| 105 | 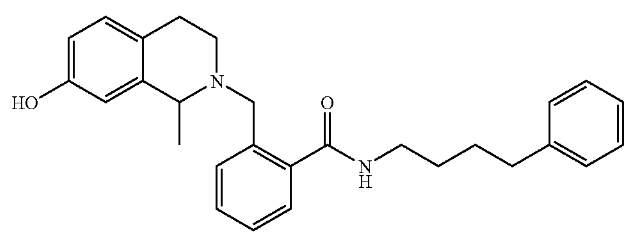 | Procedure C 0.25 g | 25 mg | 429 |
| 202 | 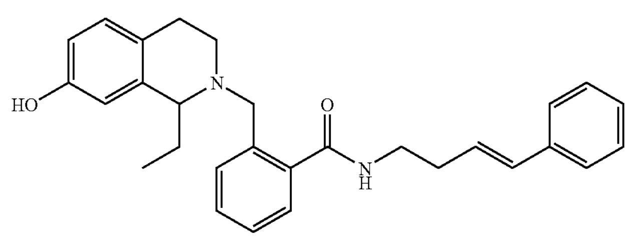 | Procedure C 0.13 g | 3.1 mg | 441 |

TABLE 1-continued

| Entry | Structure | Cleavage Procedure (Resin Cleaved in g) | Yield (mg) | m/z (M + H)+ |
|---|---|---|---|---|
| 106 | 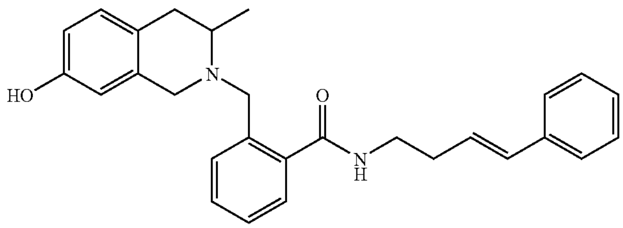 | Procedure C 0.15 g | 12 mg | 427 |
| 107 | 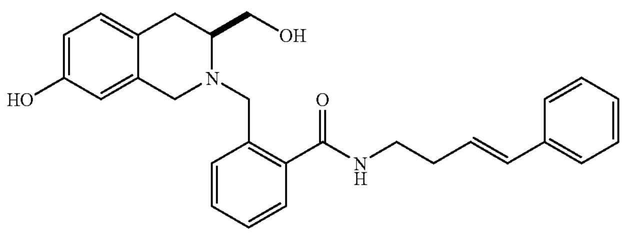 | Procedure C 0.25 g | 11 mg | 443 |
| 108 | 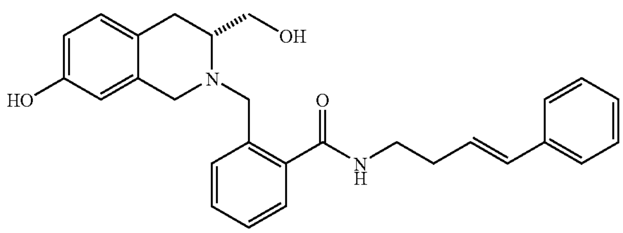 | Procedure C 0.30 g | 22 mg | 443 |
| 203 | 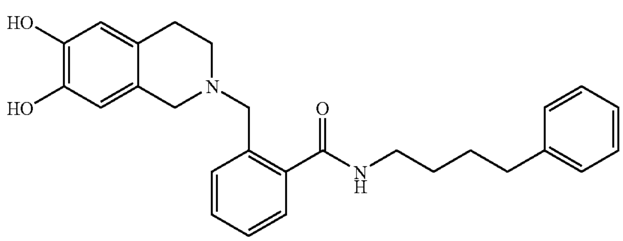 | Procedure C 0.07 g | 4.0 mg | 431 |
| 204 | 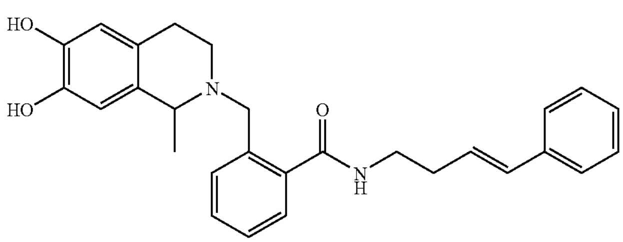 | Procedure C 0.02 g | 6.0 mg | 443 |
| 205 | 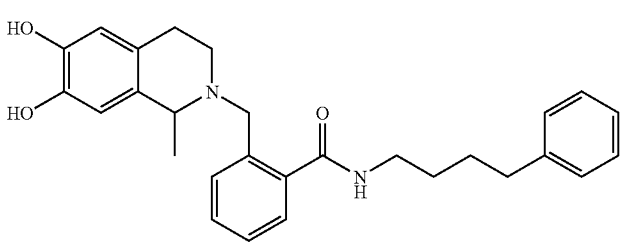 | Procedure C 0.13 g | 13 mg | 445 |

TABLE 1-continued

| Entry | Structure | Cleavage Procedure (Resin Cleaved in g) | Yield (mg) | m/z (M + H)+ |
|---|---|---|---|---|
| 401 | 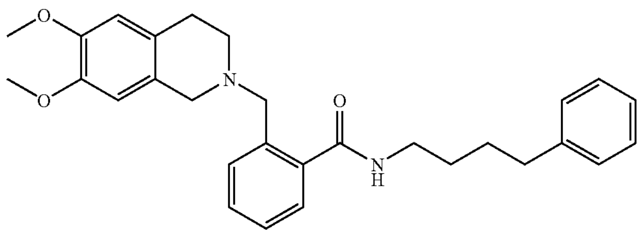 | Procedure YYY 0.13 g | 2.4 mg | 459 |
| 205 | 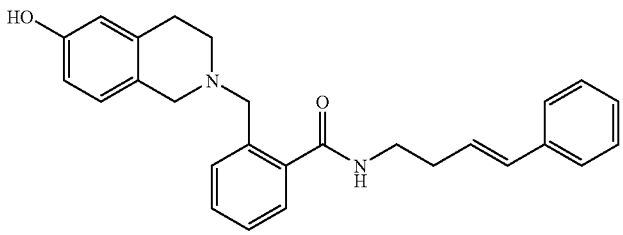 | Procedure C 0.20 g | 7.5 mg | 413 |
| 302 | 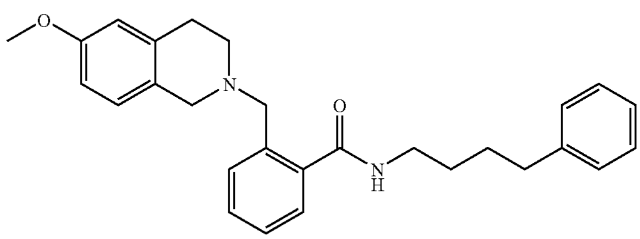 | Procedure YYY 0.30 g | 2.1 mg | 429 |
| 207 | 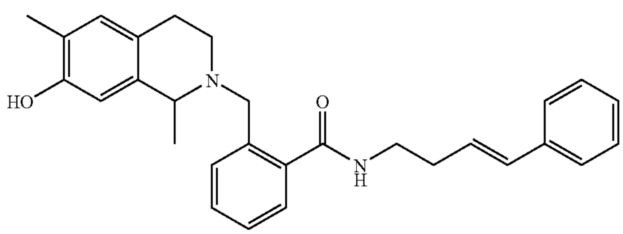 | Procedure C 0.25 g | 22 mg | 441 |
| 208 | 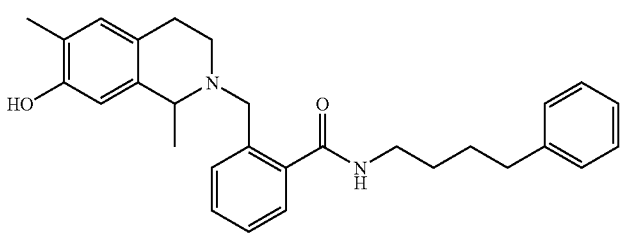 | Procedure C 0.20 g | 14 mg | 443 |
| 402 | 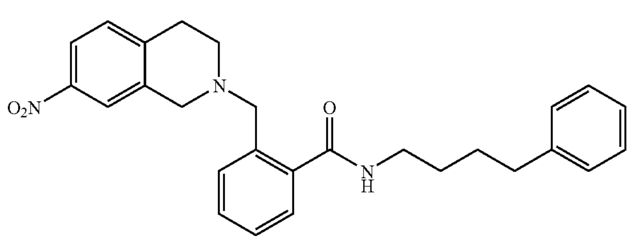 | Procedure C 0.20 g | 29 mg | 444 |

TABLE 1-continued
| Entry | Structure | Cleavage Procedure (Resin Cleaved in g) | Yield (mg) | m/z (M + H)+ |
|---|---|---|---|---|
| 209 | 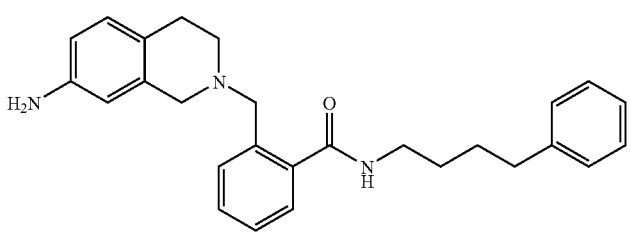 | Procedure C 0.15 g | 19 mg | 414 |
| 403 | 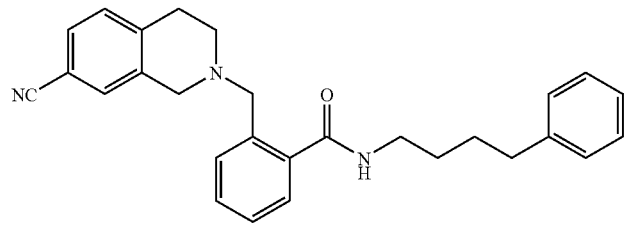 | Procedure C 0.15 g | 19 mg | 424 |
| 303 | 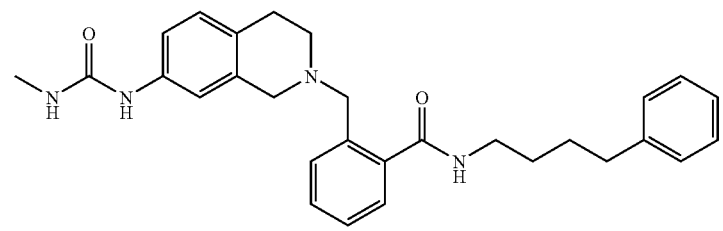 | Procedure C 0.15 g | 18 mg | 471 |
| 210 | 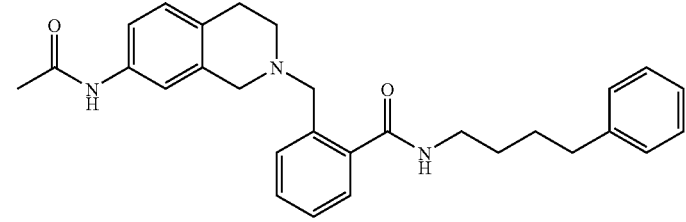 | Procedure C 0.15 g | 16 mg | 456 |
| 404 | 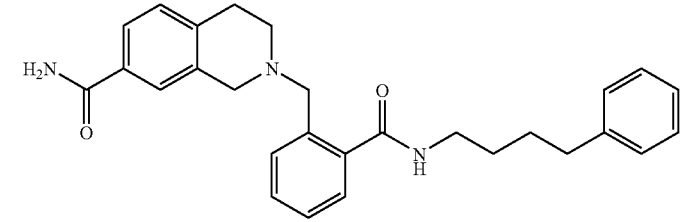 | N/A (Solution Phase Synthesis) | 3.4 mg | 442 |
| 405 | 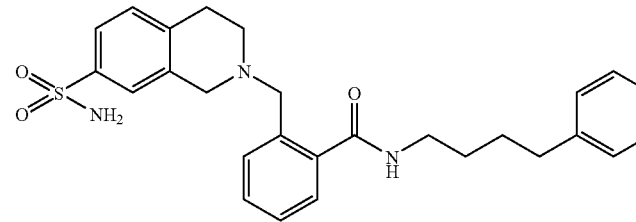 | Procedure C 0.30 g | 15 mg | 478 |

TABLE 1-continued

| Entry | Structure | Cleavage Procedure (Resin Cleaved in g) | Yield (mg) | m/z (M + H)+ |
|---|---|---|---|---|
| 406 | 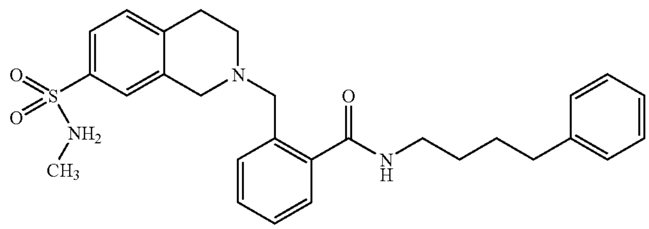 | Procedure C 0.30 g | 7.0 mg | 492 |
| 109 | 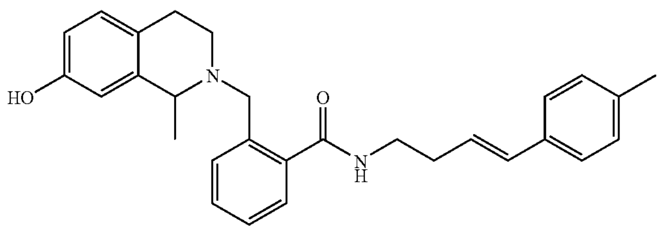 | Procedure C 0.25 g | 19 mg | 441 |
| 110 | 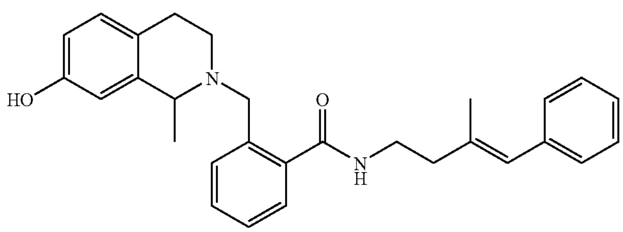 | Procedure C 0.25 g | 33 mg | 441 |
| 211 | 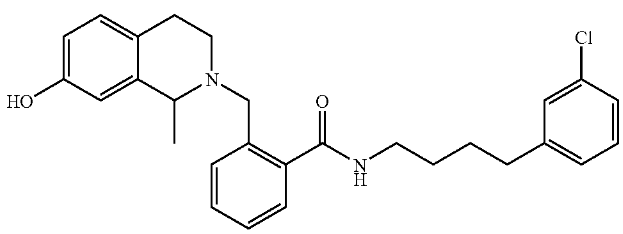 | Procedure C 0.25 g | 24 mg | 463 |
| 407 | 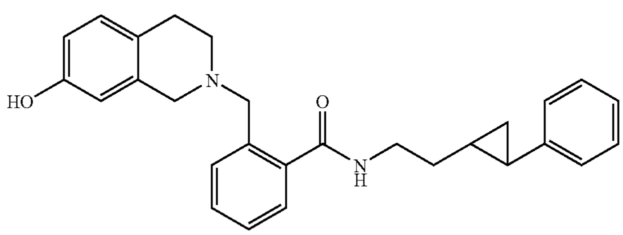 | Procedure C 0.25 g | 25 mg | 427 |
| 212 | 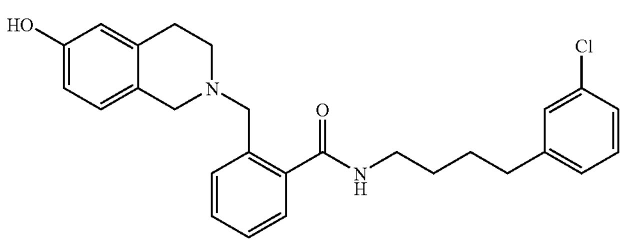 | Procedure C 0.20 g | 4.0 mg | 449 |

TABLE 1-continued

| Entry | Structure | Cleavage Procedure (Resin Cleaved in g) | Yield (mg) | m/z (M + H)+ |
|---|---|---|---|---|
| 408 | 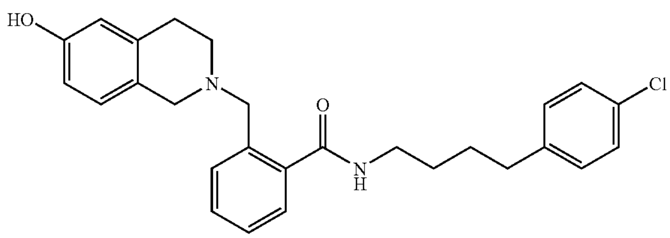 | Procedure C 0.15 g | 8.3 mg | 449 |
| 304 | 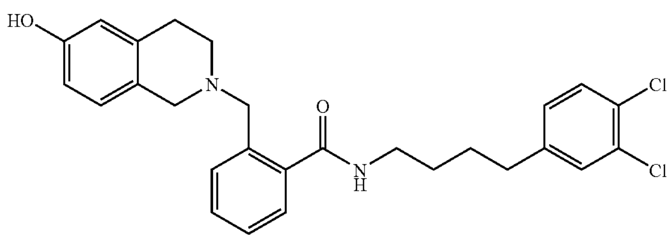 | Procedure C 0.15 g | 7.0 mg | 483/485 |
| 305 | 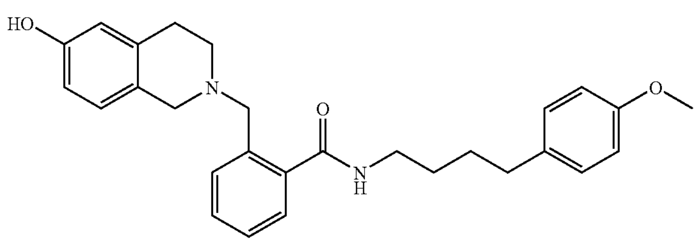 | Procedure C 0.20 g | 7.0 mg | 445 |
| 213 | 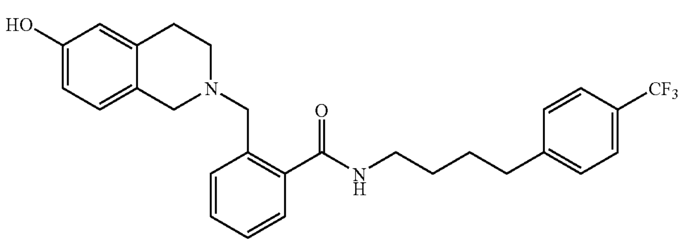 | Procedure C 0.20 g | 2.0 mg | 483 |
| 111 | 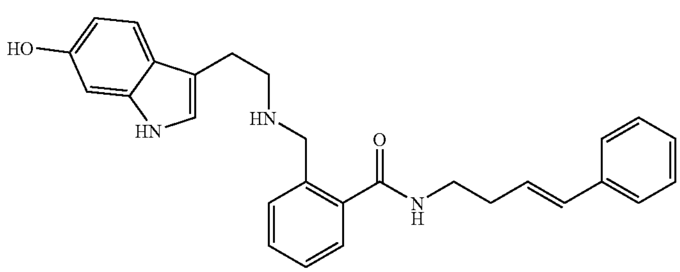 | Procedure D 0.30 g | 5.1 mg | 440 |
| 112 | 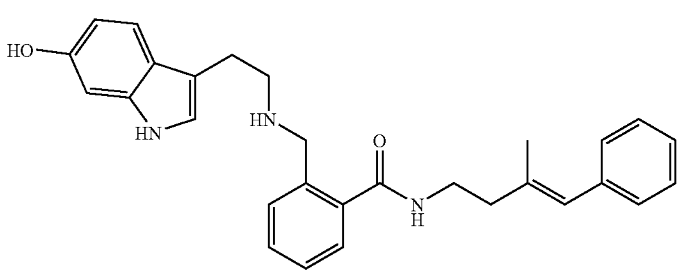 | Procedure C 0.25 g | 6.2 mg | 454 |

TABLE 1-continued

| Entry | Structure | Cleavage Procedure (Resin Cleaved in g) | Yield (mg) | m/z (M + H)+ |
|---|---|---|---|---|
| 409 | 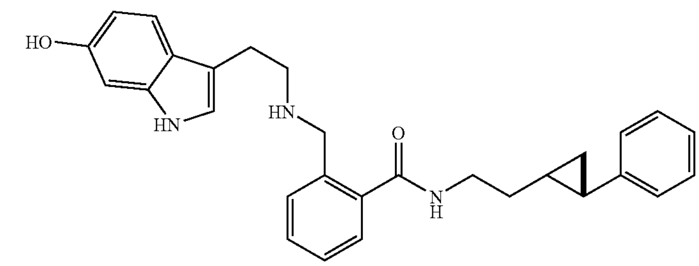 | Procedure C 0.25 g | 8.3 mg | 454 |
| 113 | 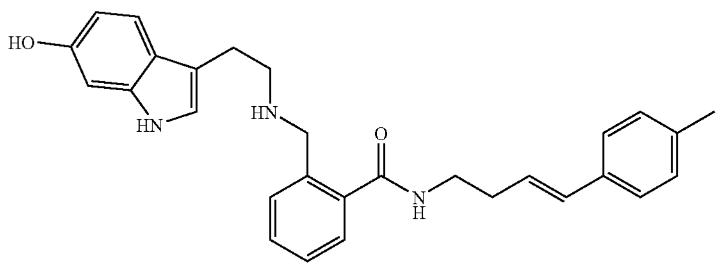 | Procedure D 0.15 g | 4.7 mg | 454 |
| 114 | 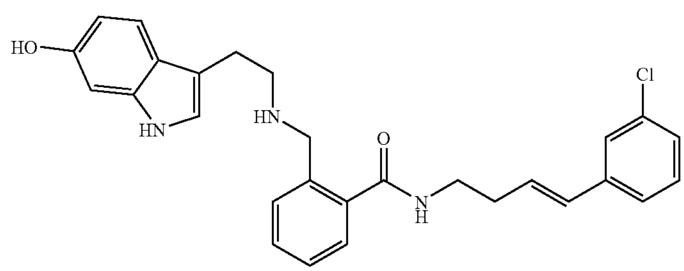 | Procedure D 0.15 g | 6.5 mg | 474 |
| 115 | 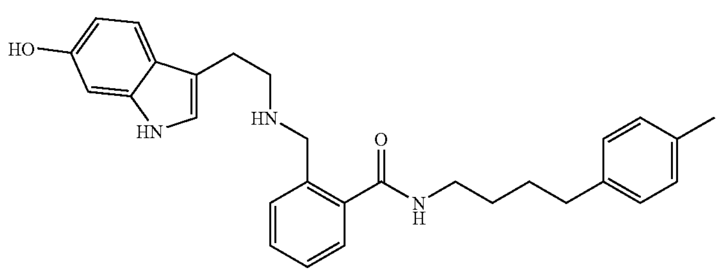 | Procedure C 0.10 g | 1.8 mg | 456 |
| 116 | 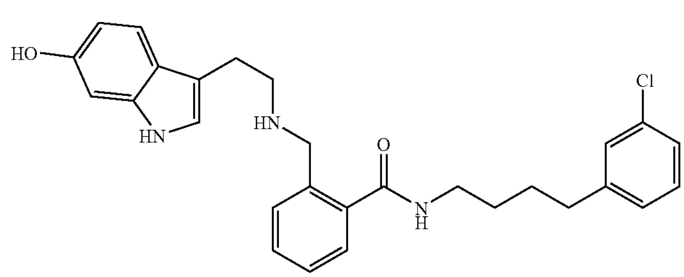 | Procedure C 0.25 g | 14 mg | 476 |

TABLE 1-continued

| Entry | Structure | Cleavage Procedure (Resin Cleaved in g) | Yield (mg) | m/z (M + H)+ |
|---|---|---|---|---|
| 214 | 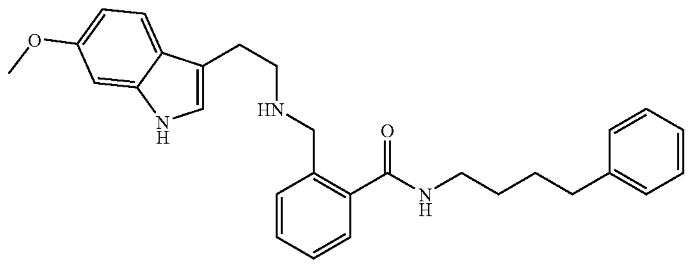 | Procedure C 0.10 g | 1.2 mg | 456 |
| 306 | 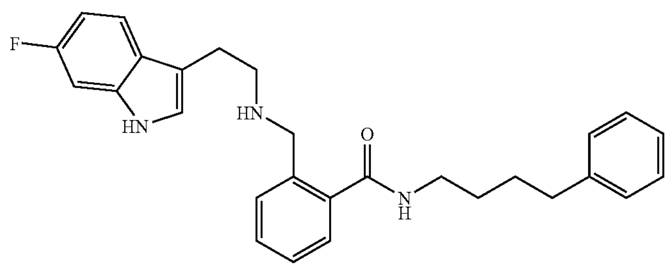 | Procedure C 0.10 g | 2.0 mg | 444 |
| 117 | 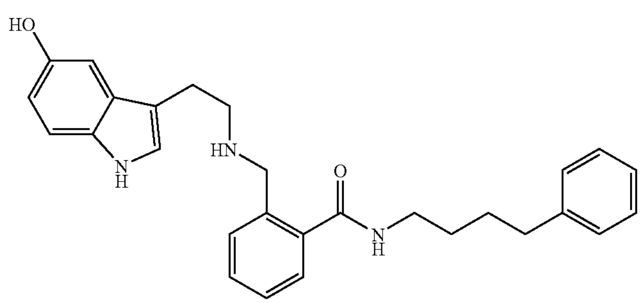 | Procedure C 0.10 g | 2.4 mg | 442 |
| 118 | 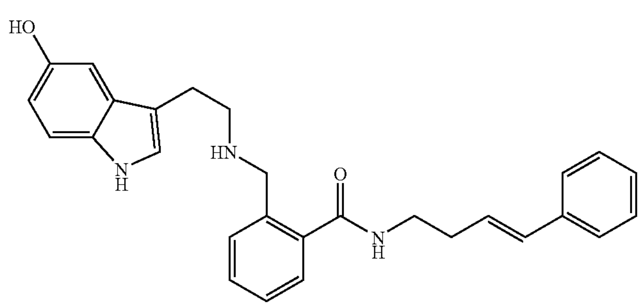 | Procedure C 0.20 g | 3.9 mg | 440 |
| 119 | 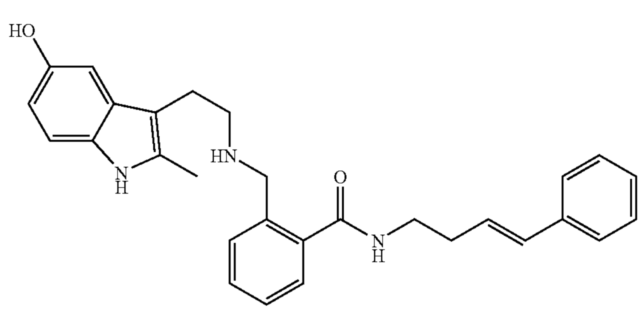 | Procedure C 0.12 g | 3.0 mg | 454 |

TABLE 1-continued

| Entry | Structure | Cleavage Procedure (Resin Cleaved in g) | Yield (mg) | m/z (M + H)+ |
|---|---|---|---|---|
| 215 | 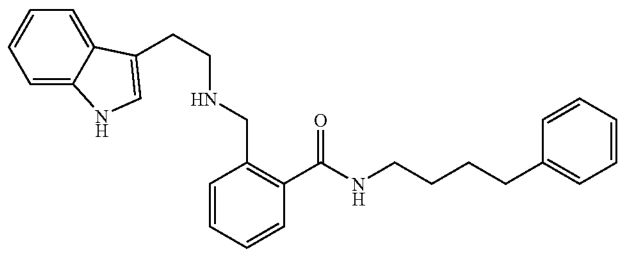 | Procedure C 0.10 g | 2.9 mg | 426 |
| 410 | 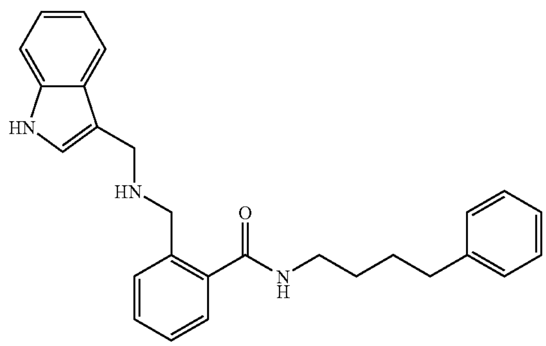 | Procedure C 0.10 g | 1.4 mg | 412 |
| 411 | 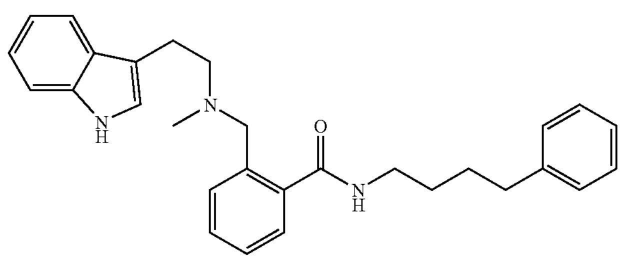 | Procedure C 0.15 g | 8.0 mg | 440 |
| 412 | 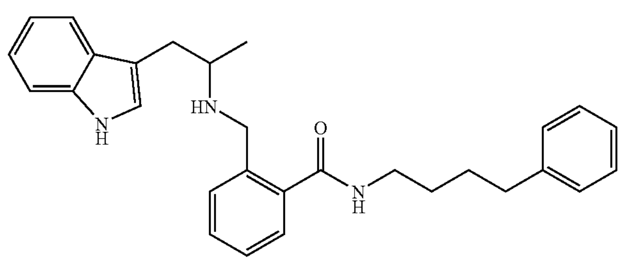 | Procedure C 0.10 g | 3.8 mg | 440 |
| 307 | 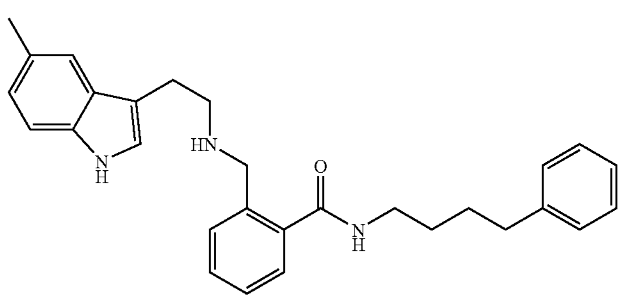 | Procedure C 0.10 g | 1.0 mg | 440 |

TABLE 1-continued

| Entry | Structure | Cleavage Procedure (Resin Cleaved in g) | Yield (mg) | m/z (M + H)+ |
|---|---|---|---|---|
| 308 | 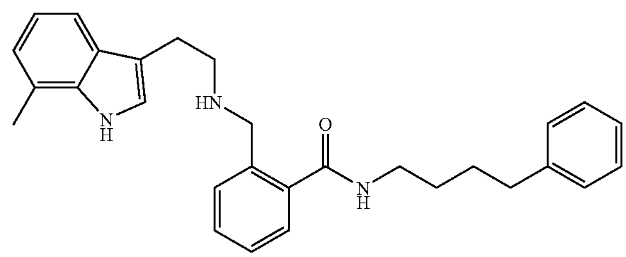 | Procedure C 0.13 g | 5.1 mg | 440 |
| 413 | 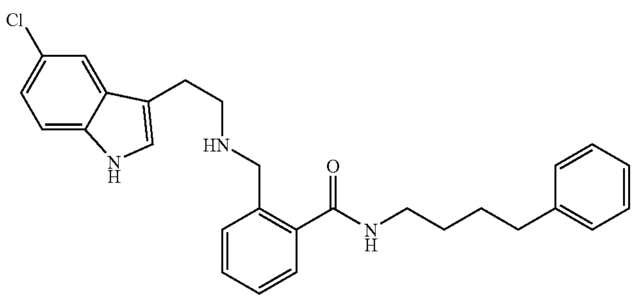 | Procedure C 0.10 g | 1.1 mg | 461 |
| 309 | 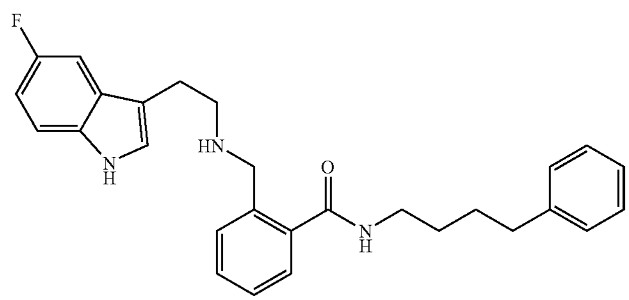 | Procedure C 0.10 g | 1.7 mg | 444 |
| 120 | 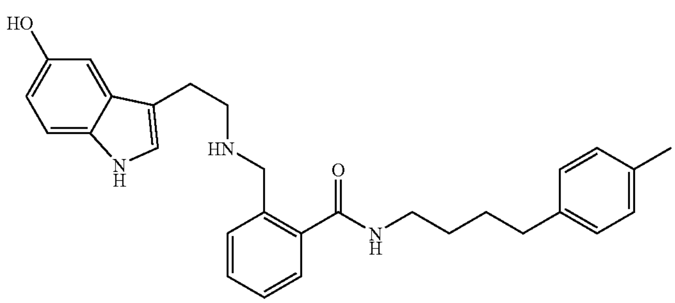 | Procedure D,E 0.45 g | 6.0 mg | 456 |
| 121 | 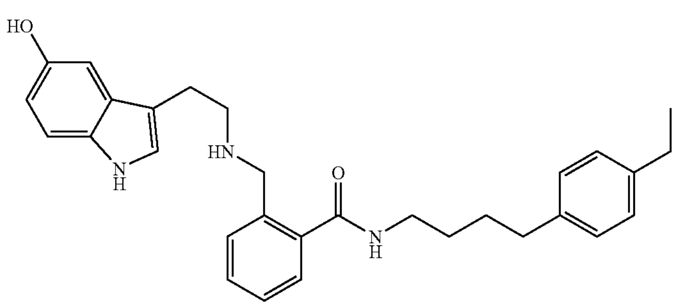 | Procedure C 0.25 g | 7.1 mg | 470 |

TABLE 1-continued

| Entry | Structure | Cleavage Procedure (Resin Cleaved in g) | Yield (mg) | m/z (M + H)+ |
|---|---|---|---|---|
| 122 | 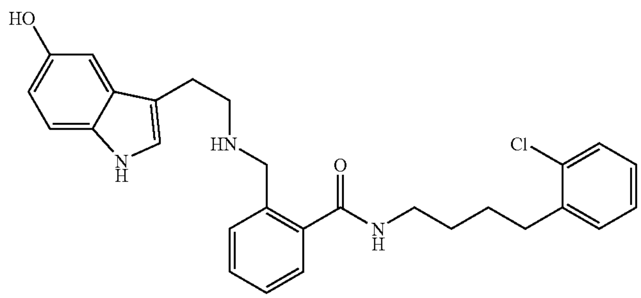 | Procedure C 0.25 g | 6.1 mg | 476 |
| 123 | 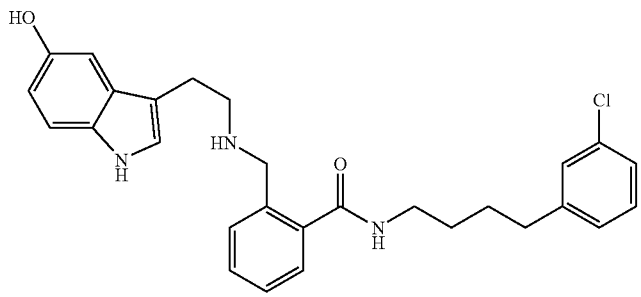 | Procedure D,E 0.70 g | 4.0 mg | 476 |
| 414 | 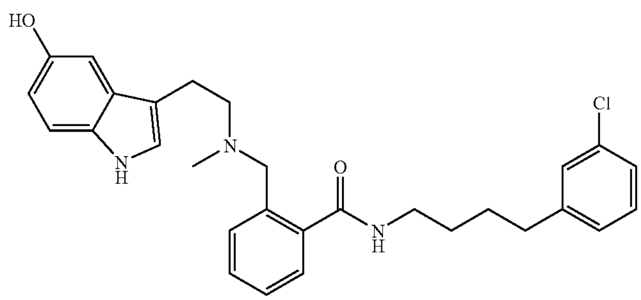 | Procedure D 0.15 g | 10 mg | 490 |
| 124 | 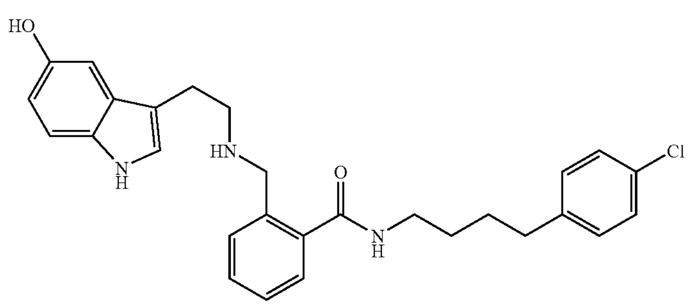 | Procedure D,E 0.40 g | 5.0 mg | 476 |
| 125 | 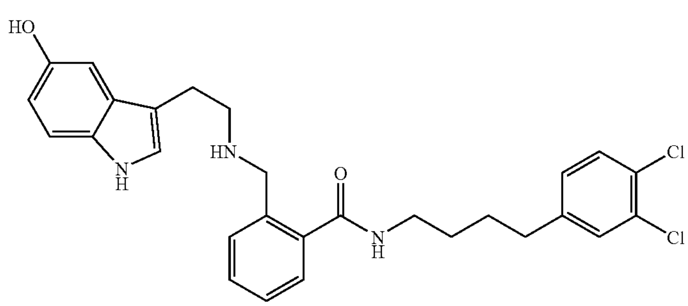 | Procedure D,E 0.45 g | 3.0 mg | 510/512 |

TABLE 1-continued
| Entry | Structure | Cleavage Procedure (Resin Cleaved in g) | Yield (mg) | m/z (M + H)+ |
|---|---|---|---|---|
| 126 | 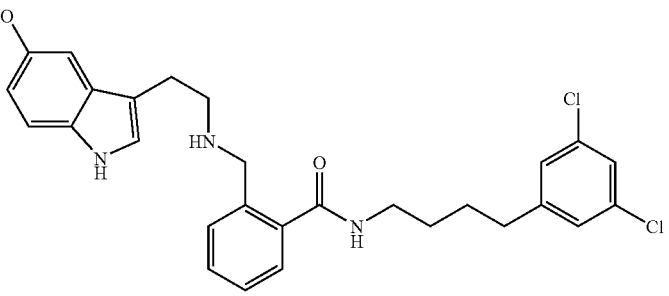 | Procedure C 0.25 g | 7.9 mg | 510/512 |
| 127 | 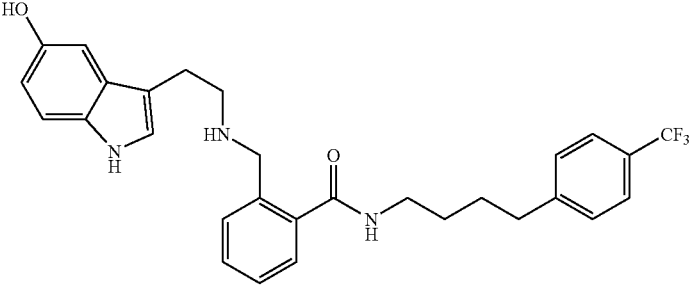 | Procedure D,E 0.30 g | 6.0 mg | 510 |
| 128 | 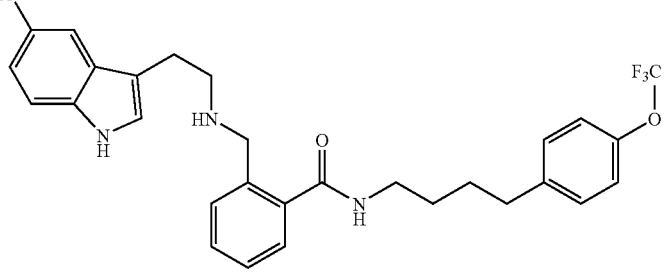 | Procedure D,E 0.35 g | 13 mg | 526 |
| 129 | 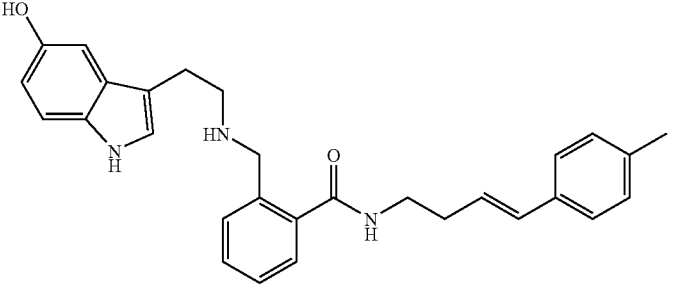 | Procedure C 0.35 g | 9.0 mg | 454 |
| 130 | 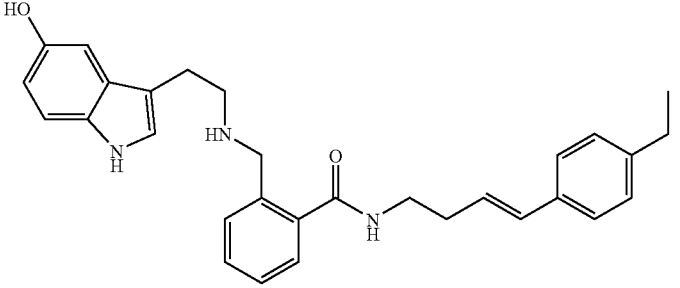 | Procedure C 0.25 g | 6.1 mg | 468 |

TABLE 1-continued

| Entry | Structure | Cleavage Procedure (Resin Cleaved in g) | Yield (mg) | m/z (M + H)+ |
|---|---|---|---|---|
| 131 | 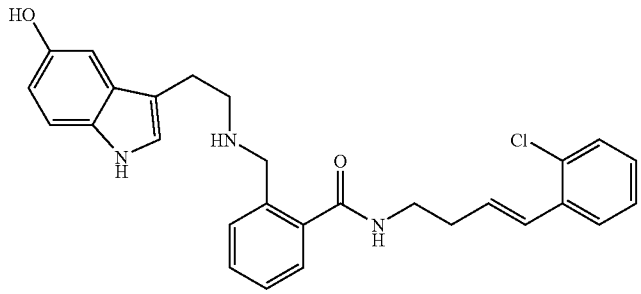 | Procedure C 0.25 g | 5.0 mg | 474 |
| 132 | 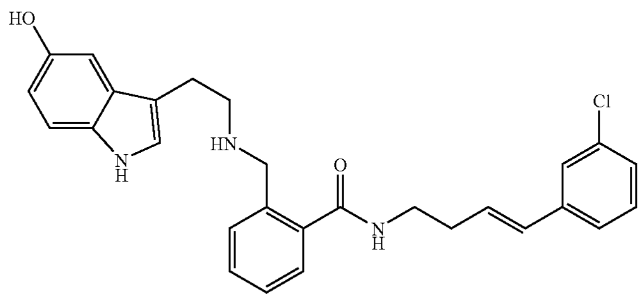 | Procedure D 0.25 g | 5.0 mg | 474 |
| 133 | 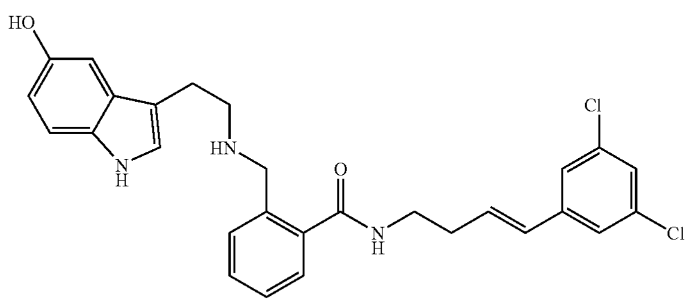 | Procedure C 0.25 g | 8.7 mg | 508 |
| 310 | 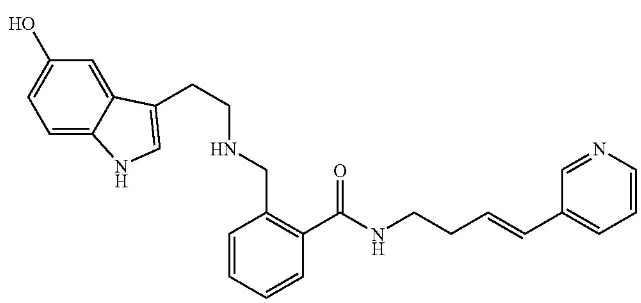 | Procedure C 0.25 g | 3.6 mg | 441 |
| 216 | 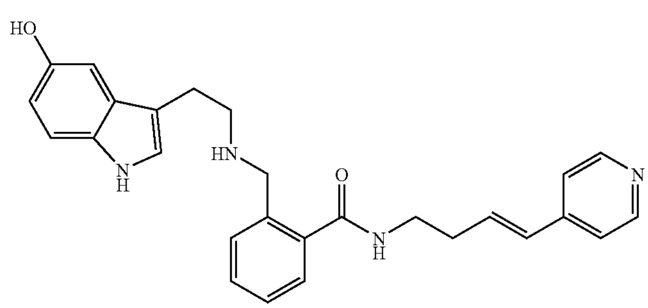 | Procedure C 0.25 g | 2.5 mg | 441 |

TABLE 1-continued

| Entry | Structure | Cleavage Procedure (Resin Cleaved in g) | Yield (mg) | m/z (M + H)+ |
|---|---|---|---|---|
| 217 | 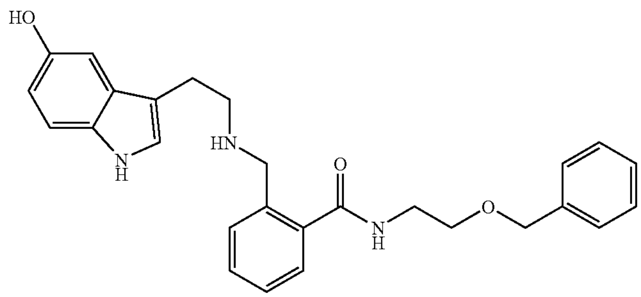 | Procedure C 0.25 g | 9.8 mg | 444 |
| 134 | 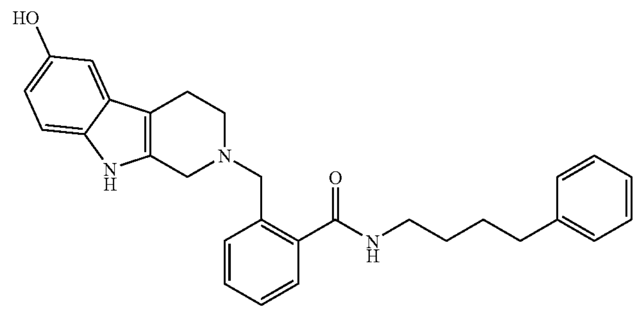 | Procedure C 0.13 g | 7.0 mg | 454 |
| 135 | 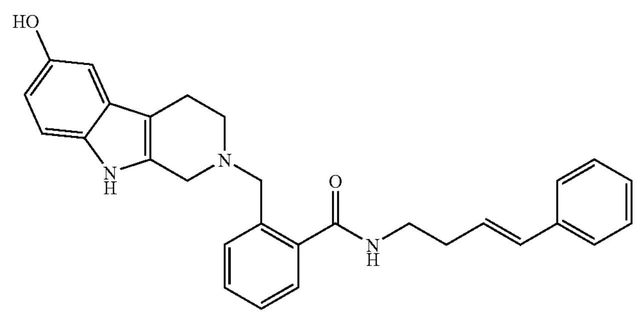 | Procedure C 0.19 g | 7.0 mg | 452 |
| 136 | 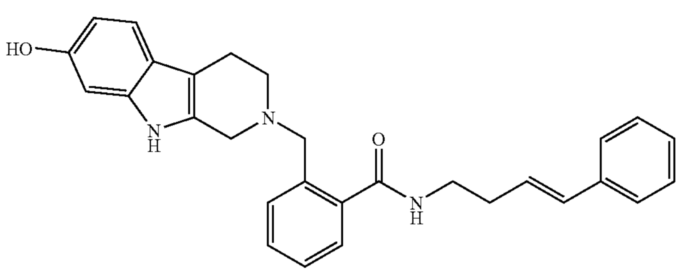 | Procedure D 0.20 g | 3.8 mg | 452 |
| 415 | 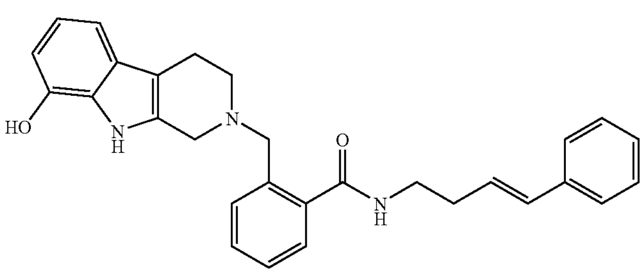 | Procedure C 0.35 g | 7 mg | 454 |

TABLE 1-continued

| Entry | Structure | Cleavage Procedure (Resin Cleaved in g) | Yield (mg) | m/z (M + H)+ |
|---|---|---|---|---|
| 218 | 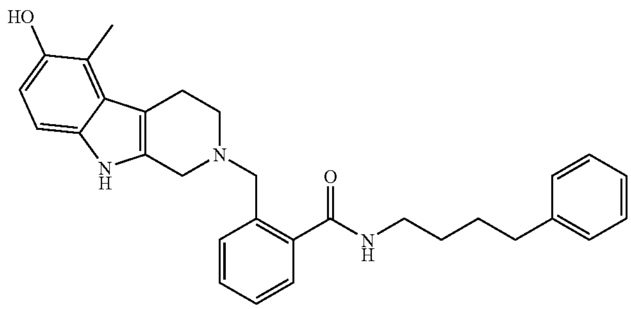 | Procedure C 0.30 g | 8.0 mg | 468 |
| 137 | 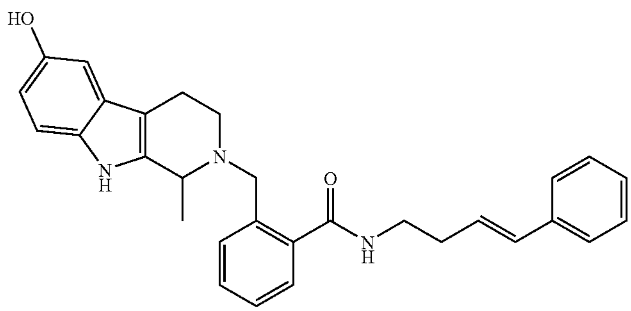 | Procedure C 0.15 g | 9.5 mg | 466 |
| 416 | 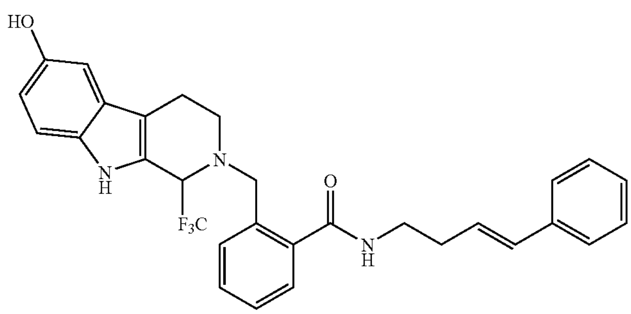 | Procedure C 0.15 g | 4.0 mg | 520 |
| 219 | 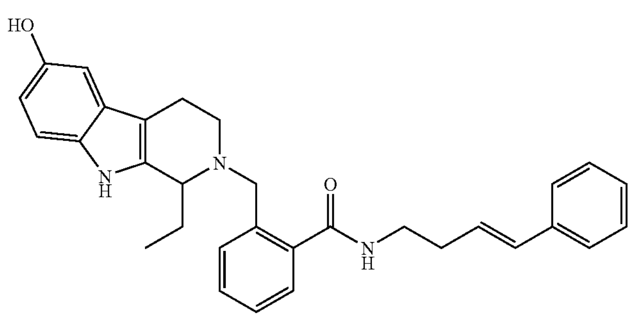 | Procedure D 0.20 g | 10 mg | 480 |
| 220 | 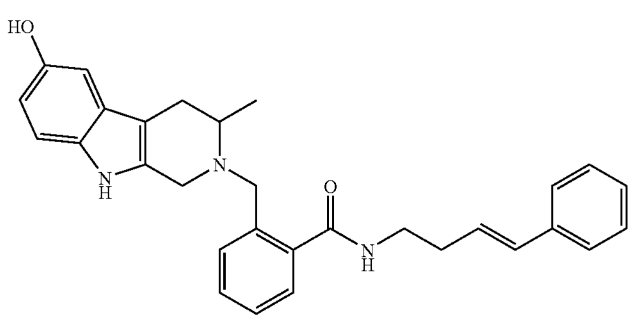 | Procedure C 0.15 g | 4.1 mg | 466 |

TABLE 1-continued
| Entry | Structure | Cleavage Procedure (Resin Cleaved in g) | Yield (mg) | m/z (M + H)+ |
|---|---|---|---|---|
| 221 | 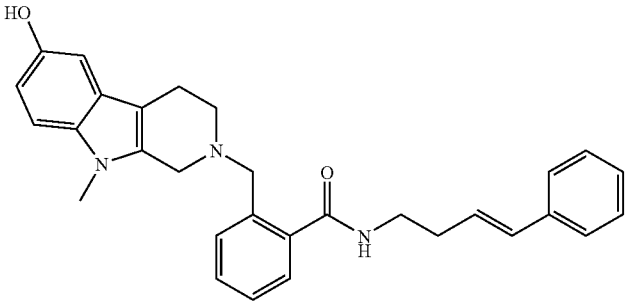 | Procedure C 0.15 g | 2.0 mg | 466 |
| 138 | 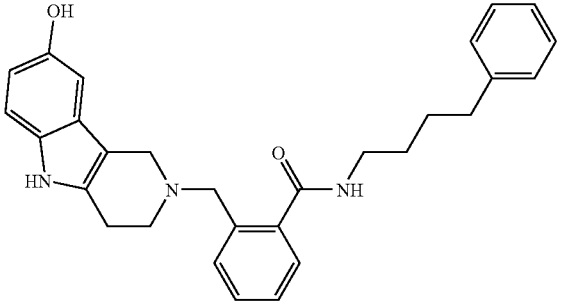 | Procedure C,E 0.40 g | 19 mg | 454 |
| 417 | 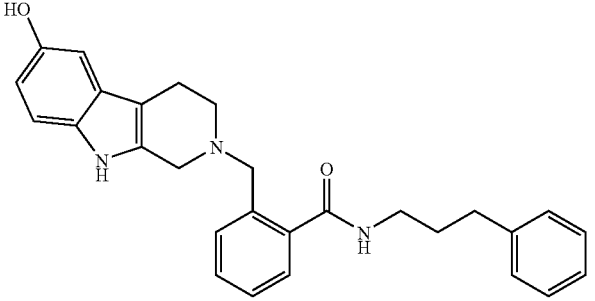 | Procedure C 0.25 g | 10 mg | 440 |
| 139 | 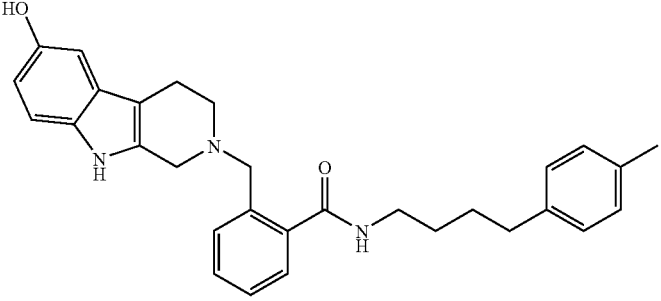 | Procedure C 0.20 g | 15 mg | 468 |

TABLE 1-continued

| Entry | Structure | Cleavage Procedure (Resin Cleaved in g) | Yield (mg) | m/z (M + H)+ |
|---|---|---|---|---|
| 222 | 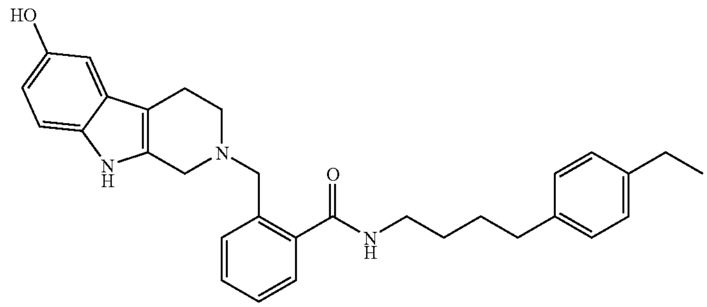 | Procedure C 0.25 g | 13 mg | 482 |
| 223 | 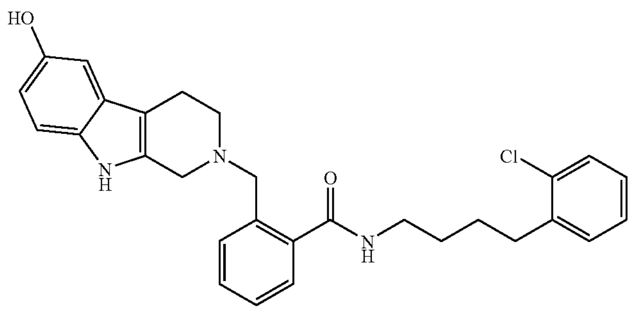 | Procedure C 0.25 g | 17 mg | 488 |
| 140 | 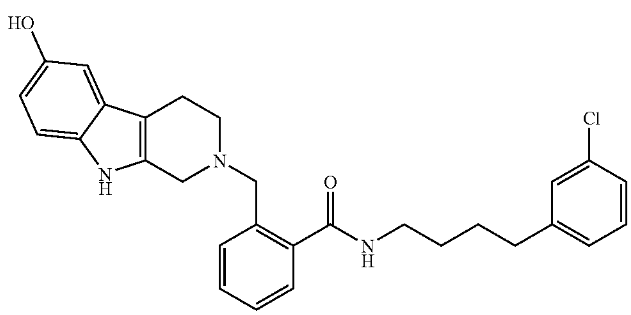 | Procedure C 0.20 g | 8.3 mg | 488 |
| 224 | 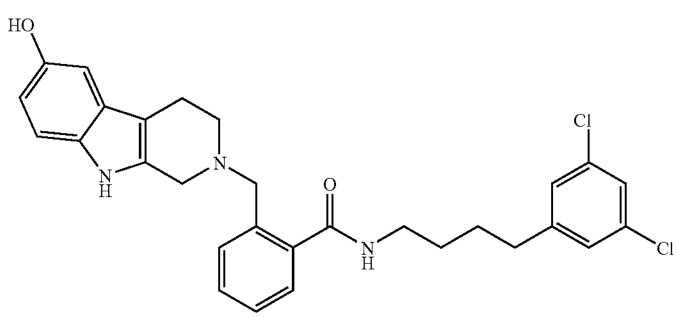 | Procedure C 0.25 g | 17 mg | 522 |
| 225 | 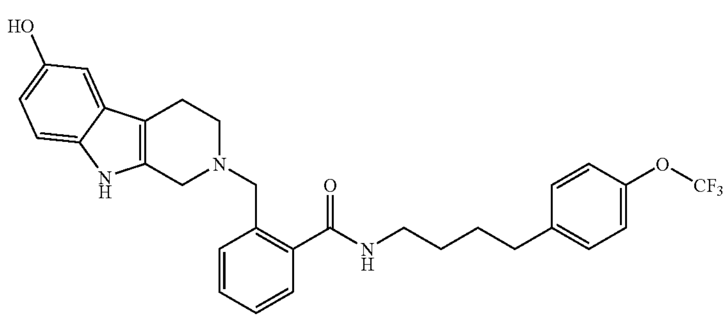 | Procedure C 0.10 g | 2.4 mg | 538 |

TABLE 1-continued
| Entry | Structure | Cleavage Procedure (Resin Cleaved in g) | Yield (mg) | m/z (M + H)+ |
|---|---|---|---|---|
| 141 | 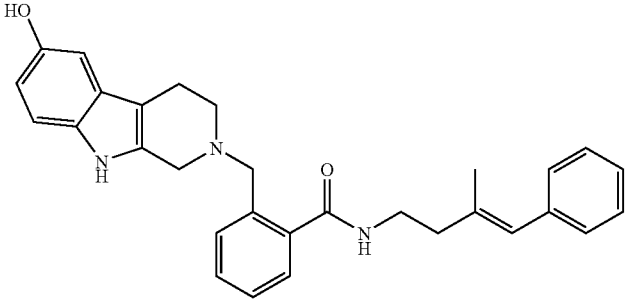 | Procedure C 0.25 g | 35 mg | 466 |
| 226 | 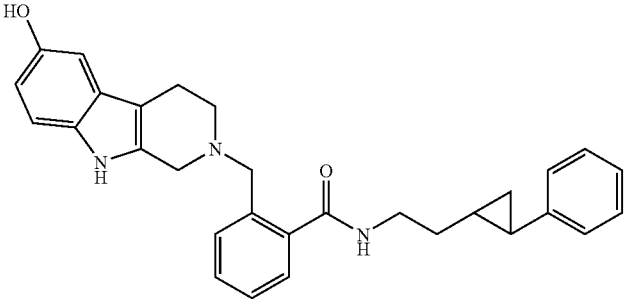 | Procedure C 0.25 g | 15 mg | 466 |
| 227 | 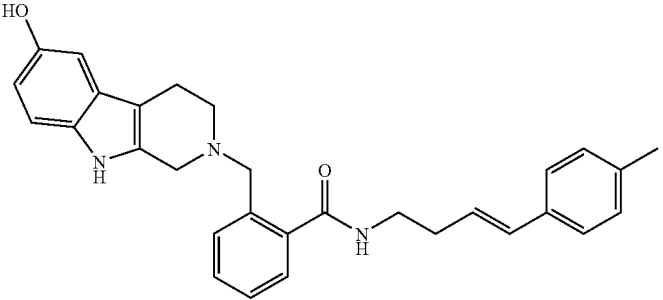 | Procedure C 0.20 g | 5 mg | 466 |
| 228 | 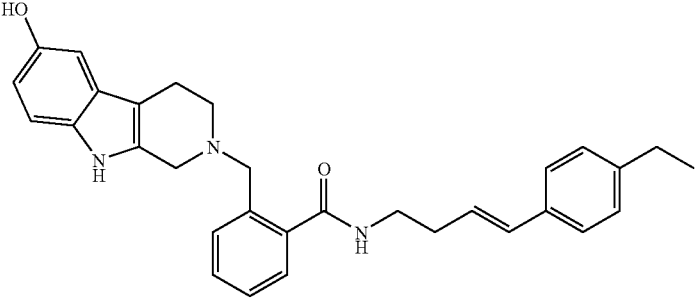 | Procedure C 0.25 g | 8.0 mg | 480 |

TABLE 1-continued

| Entry | Structure | Cleavage Procedure (Resin Cleaved in g) | Yield (mg) | m/z (M + H)+ |
|---|---|---|---|---|
| 229 | 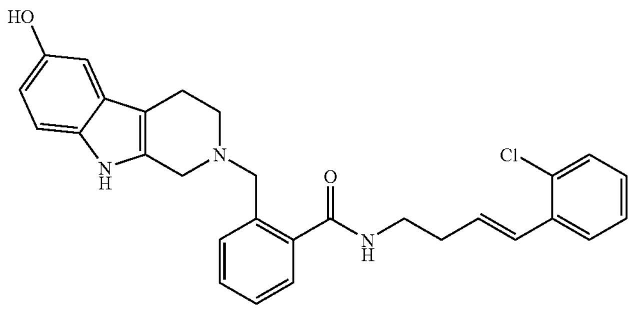 | Procedure C 0.25 g | 9.4 mg | 486 |
| 142 | 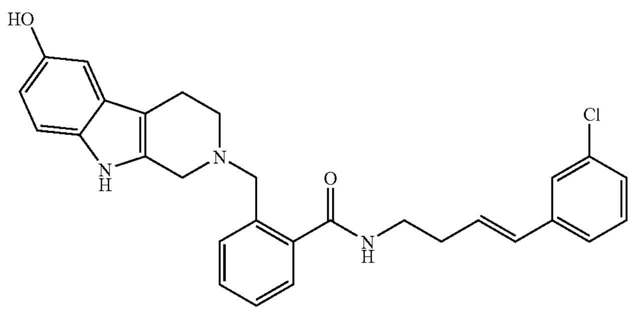 | Procedure C 0.15 g | 9.1 mg | 486 |
| 311 | 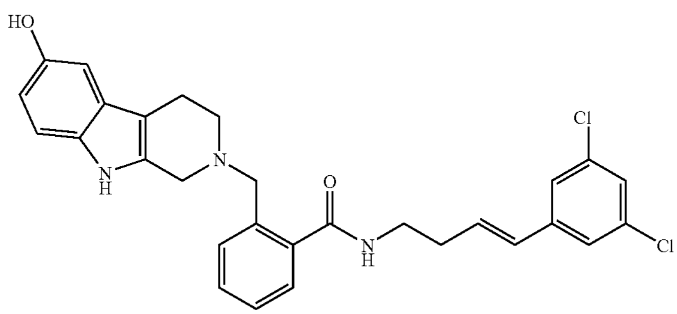 | Procedure C 0.25 g | 9.5 mg | 520 |
| 230 | 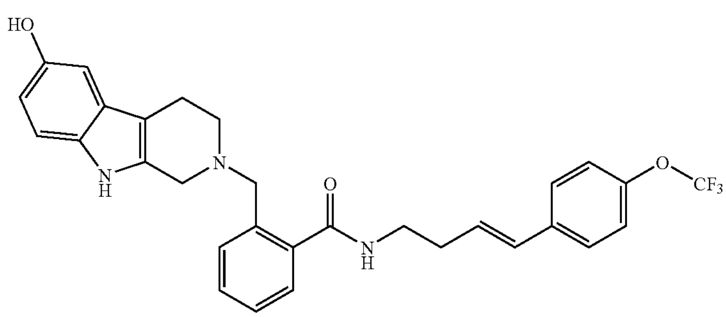 | Procedure C 0.25 g | 14 mg | 536 |
| 418 | 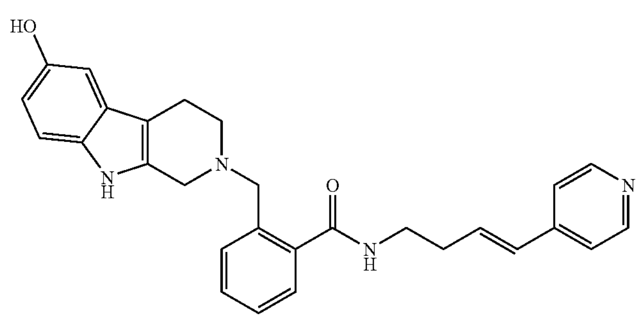 | Procedure C 0.25 g | 5.1 mg | 453 |

TABLE 1-continued
| Entry | Structure | Cleavage Procedure (Resin Cleaved in g) | Yield (mg) | m/z (M + H)+ |
|---|---|---|---|---|
| 419 | 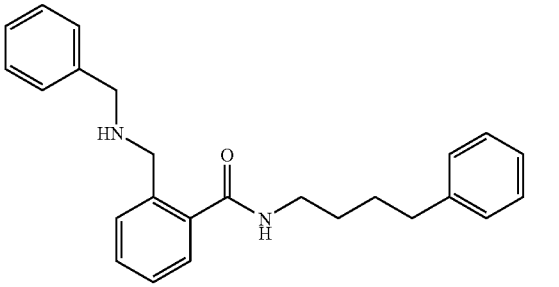 | Procedure C 0.03 g | 0.7 mg | 373 |
| 420 | 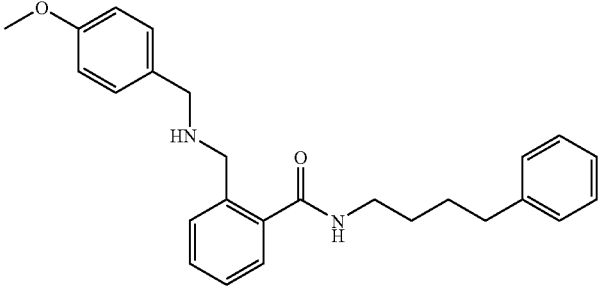 | Procedure YYY 0.10 g | 2.2 mg | 403 |
| 421 | 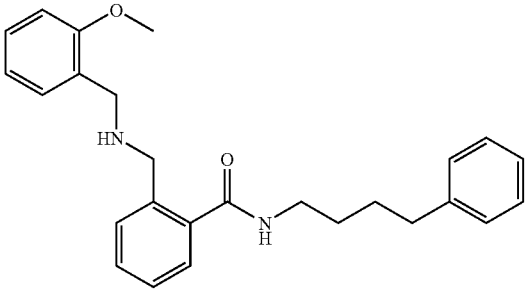 | Procedure C 0.03 g | 2.2 mg | 403 |
| 422 | 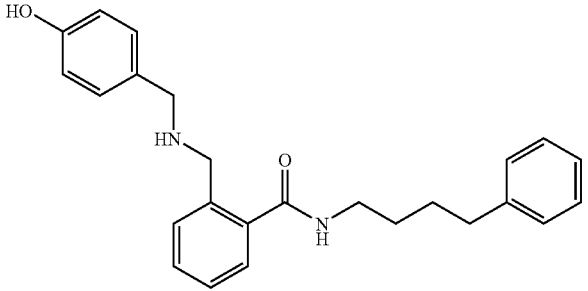 | Procedure YYY, then Procedure 0.20 g | 6.0 mg | 389 |
| 423 | 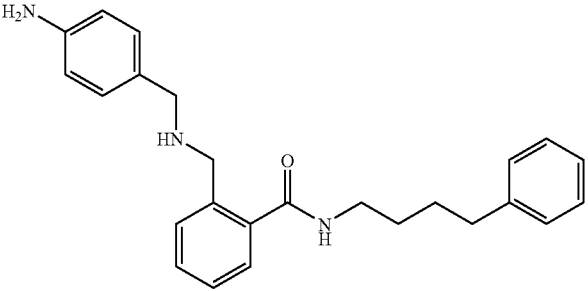 | Procedure C 0.20 g | 10 mg | 388 |

TABLE 1-continued

| Entry | Structure | Cleavage Procedure (Resin Cleaved in g) | Yield (mg) | m/z (M + H)+ |
|---|---|---|---|---|
| 424 | 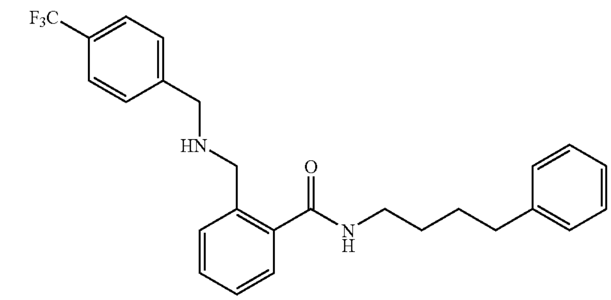 | Procedure C 0.05 g | 3.2 mg | 441 |
| 425 | 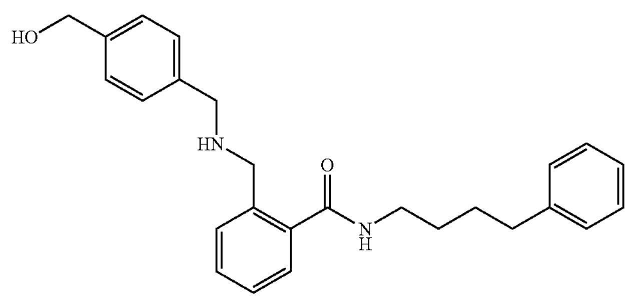 | Procedure C 0.05 g | 5.0 mg | 403 |
| 426 | 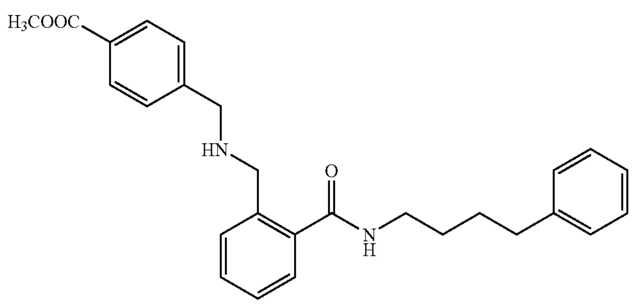 | Procedure C 0.10 g | 4.0 mg | 431 |
| 143 | 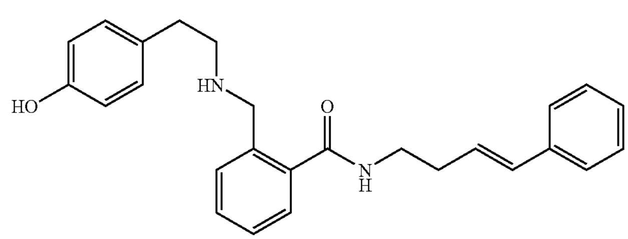 | Procedure C 0.20 g | 7.0 mg | 401 |
| 231 | 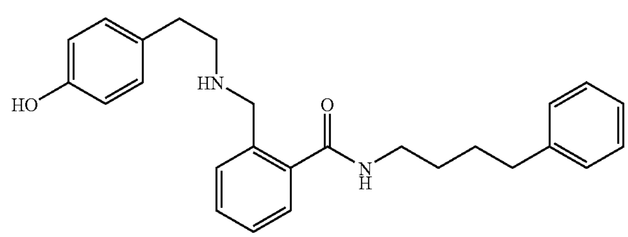 | Procedure C 0.03 g | 0.9 mg | 403 |

TABLE 1-continued

| Entry | Structure | Cleavage Procedure (Resin Cleaved in g) | Yield (mg) | m/z (M + H)+ |
|---|---|---|---|---|
| 232 | 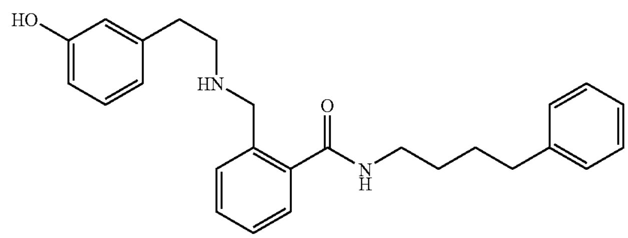 | Procedure C 0.30 g | 10 mg | 403 |
| 427 | 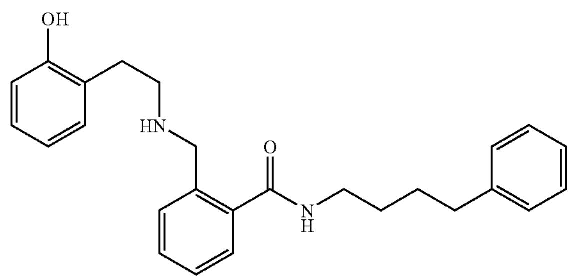 | Procedure C 0.30 g | 14 mg | 403 |
| 428 | 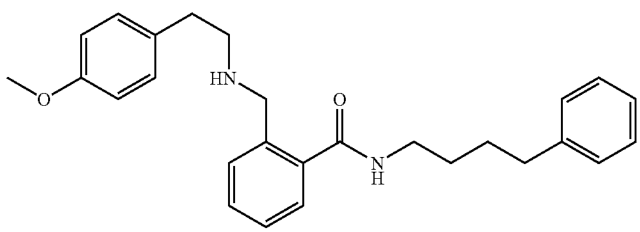 | Procedure C 0.03 g | 0.6 mg | 417 |
| 429 | 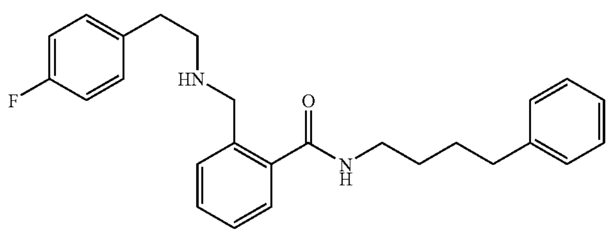 | Procedure C 0.20 g | 7.0 mg | 405 |
| 430 | 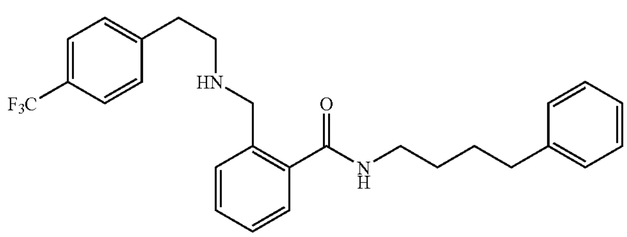 | Procedure C 0.10 g | 5.5 mg | 455 |
| 233 | 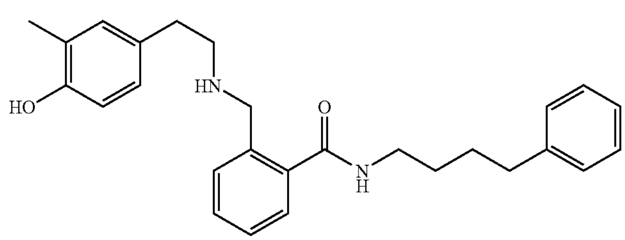 | Procedure C 0.10 g | 0.8 mg | 417 |

TABLE 1-continued

| Entry | Structure | Cleavage Procedure (Resin Cleaved in g) | Yield (mg) | m/z (M + H)+ |
|---|---|---|---|---|
| 234 | 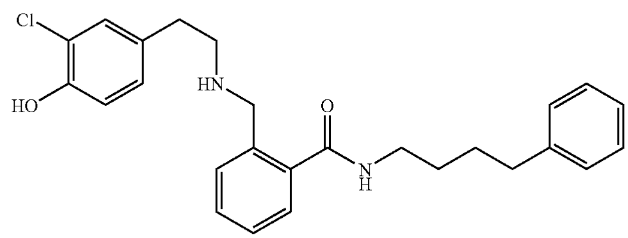 | Procedure C 0.10 g | 9.0 mg | 438 |
| 431 | 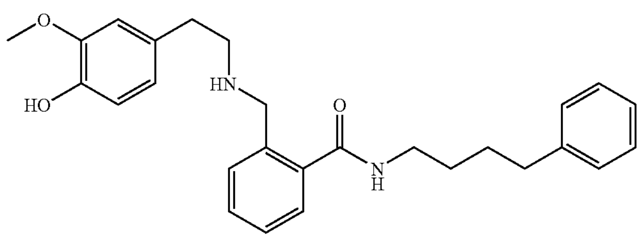 | Procedure C 0.20 g | 10 mg | 433 |
| 235 | 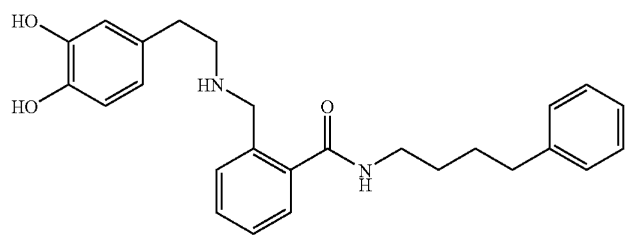 | Procedure C 0.20 g | 0.7 mg | 419 |
| 432 | 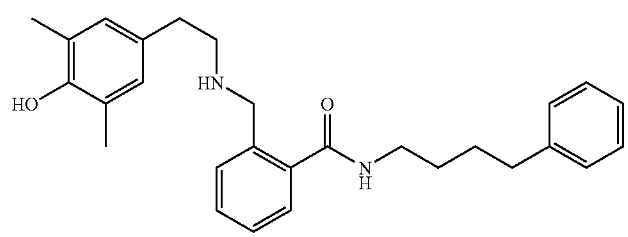 | Procedure C 0.15 g | 12 mg | 431 |
| 433 | 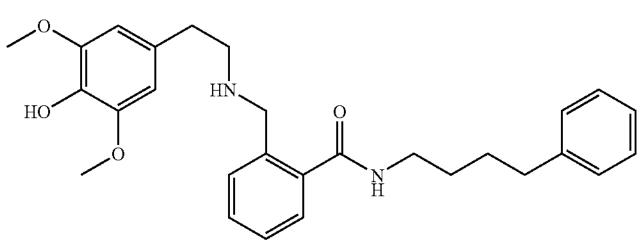 | Procedure C 0.05 g | 6.0 mg | 463 |
| 236 | 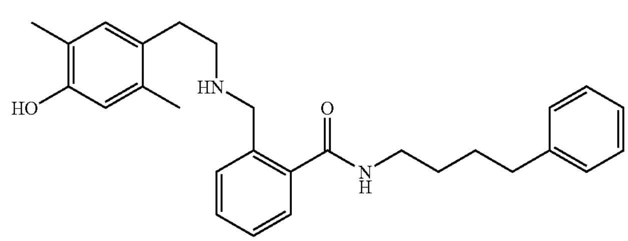 | Procedure C 0.20 g | 9.0 mg | 431 |

TABLE 1-continued

| Entry | Structure | Cleavage Procedure (Resin Cleaved in g) | Yield (mg) | m/z (M + H)+ |
|---|---|---|---|---|
| 312 | 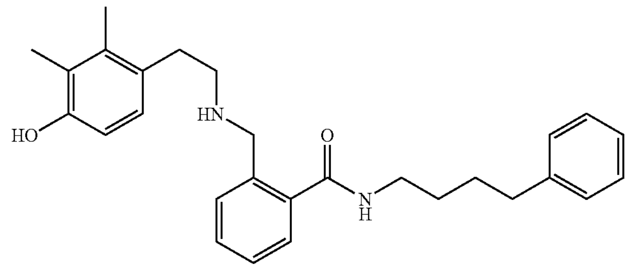 | Procedure C 0.20 g | 22 mg | 431 |
| 434 | 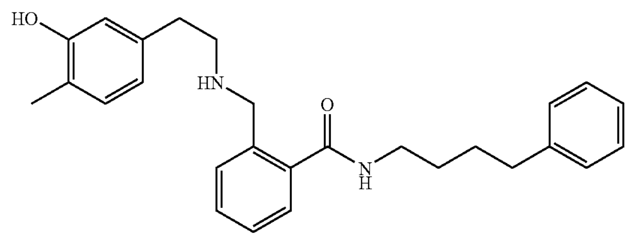 | Procedure C 0.20 g | 28 mg | 417 |
| 435 | 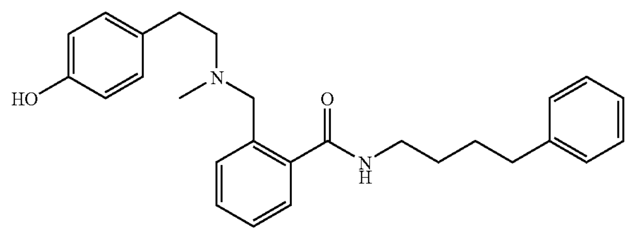 | Procedure C 0.13 g | 10 mg | 417 |
| 436 | 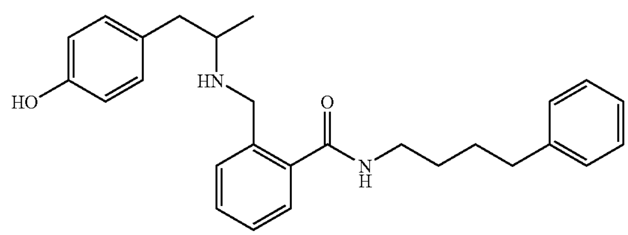 | Procedure YYY 0.50 g | 6.0 mg | 417 |
| 437 | 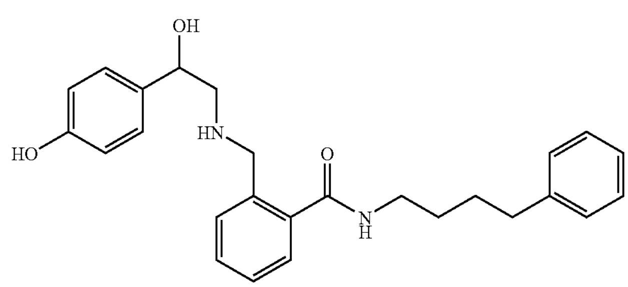 | Procedure YYY 0.10 g | 4.4 mg | 419 |
| 313 | 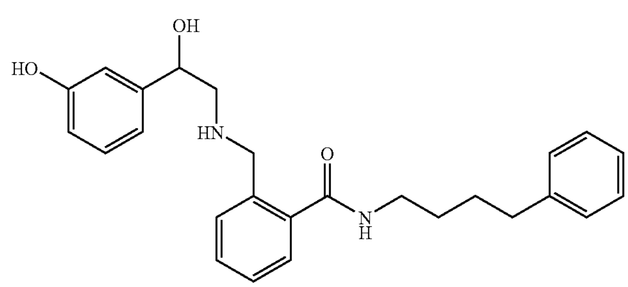 | Procedure C 0.10 g | 1.0 mg | 419 |

TABLE 1-continued

| Entry | Structure | Cleavage Procedure (Resin Cleaved in g) | Yield (mg) | m/z (M + H)+ |
|---|---|---|---|---|
| 438 | 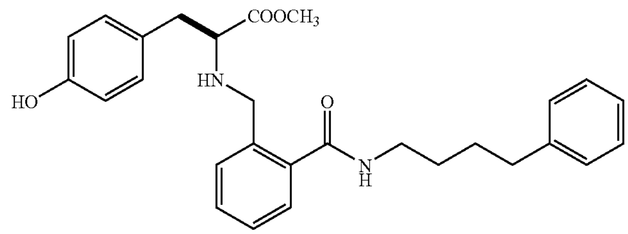 | Procedure C 0.10 g | 3.3 mg | 461 |
| 439 | 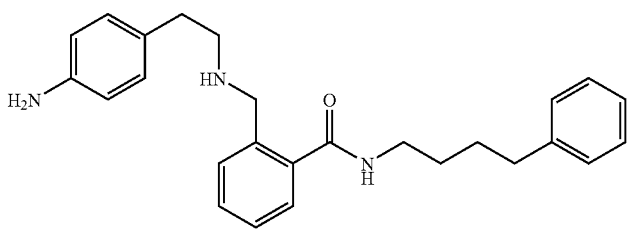 | Procedure C 0.20 g | 18 mg | 402 |
| 237 | 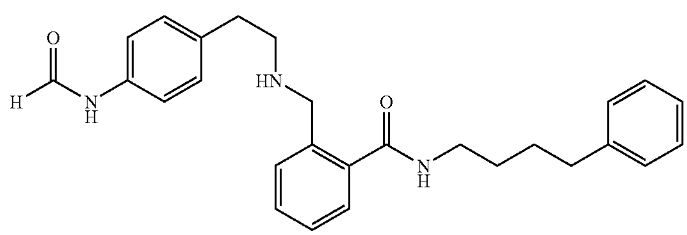 | Procedure C 0.15 g | 1.1 mg | 430 |
| 144 | 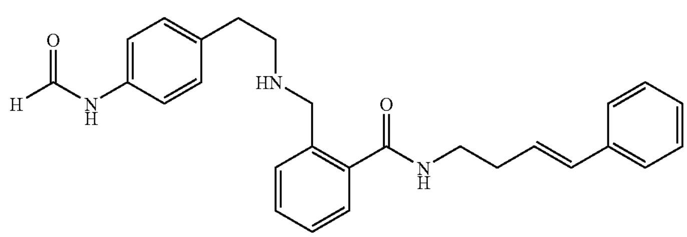 | Procedure D 0.30 g | 1.7 mg | 428 |
| 440 | 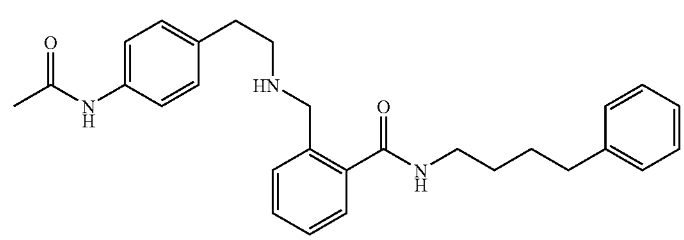 | Procedure C 0.13 g | 1.8 mg | 444 |
| 441 | 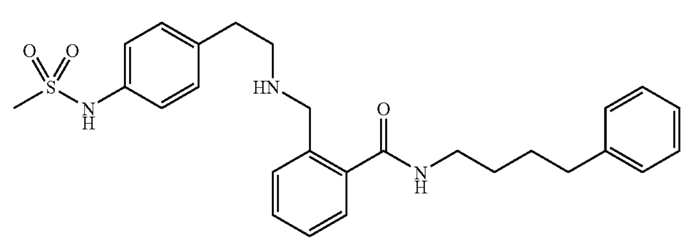 | Procedure C 0.15 g | 2.7 mg | 480 |

TABLE 1-continued

| Entry | Structure | Cleavage Procedure (Resin Cleaved in g) | Yield (mg) | m/z (M + H)+ |
|---|---|---|---|---|
| 442 | 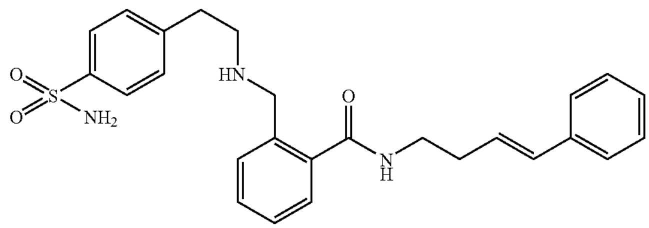 | Procedure C 0.15 g | 6.1 mg | 464 |
| 443 | 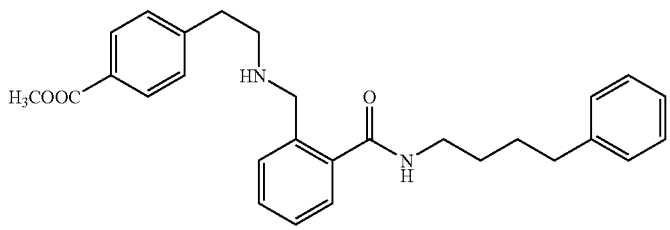 | Procedure C 0.05 g | 5.0 mg | 445 |
| 314 | 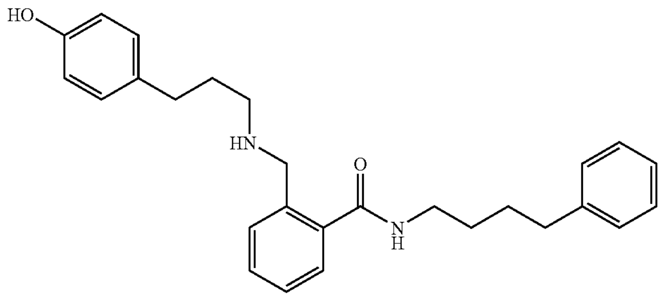 | Procedure C,E 0.30 g | 2 mg | 417 |
| 315 | 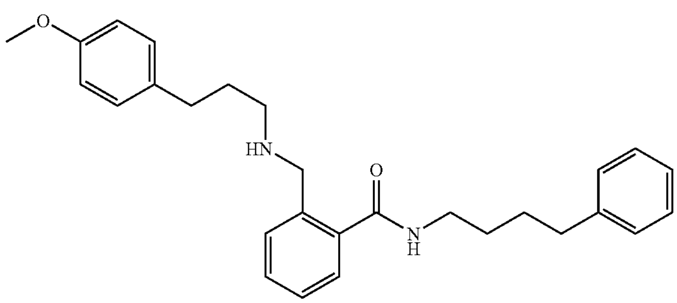 | Procedure C 0.05 g | 4 mg | 431 |
| 444 | 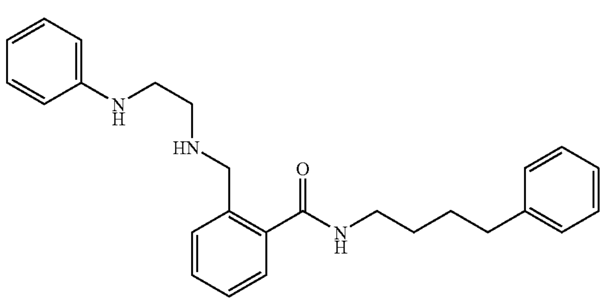 | Procedure C 0.05 g | 4.7 mg | 402 |

TABLE 1-continued

| Entry | Structure | Cleavage Procedure (Resin Cleaved in g) | Yield (mg) | m/z (M + H)+ |
|---|---|---|---|---|
| 445 | 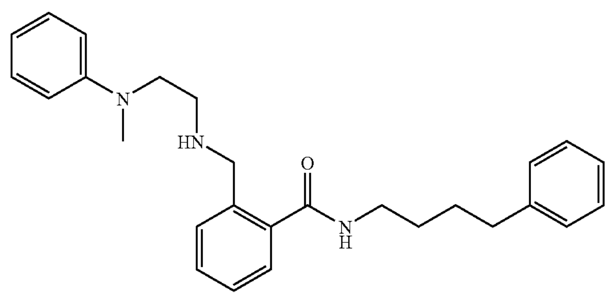 | Procedure C 0.05 g | 4.9 mg | 430 |
| 238 | 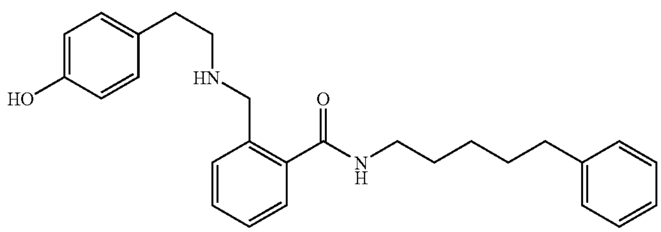 | Procedure YYY 0.29 g | 15 mg | 417 |
| 446 | 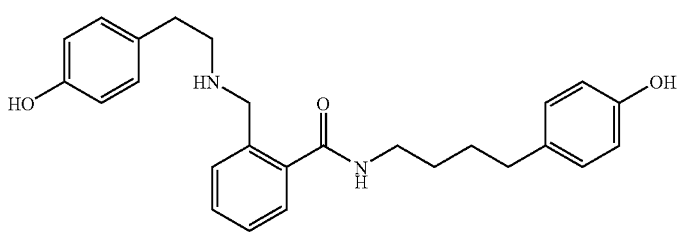 | Procedure C,E 0.25 g | 10 mg | 419 |
| 145 | 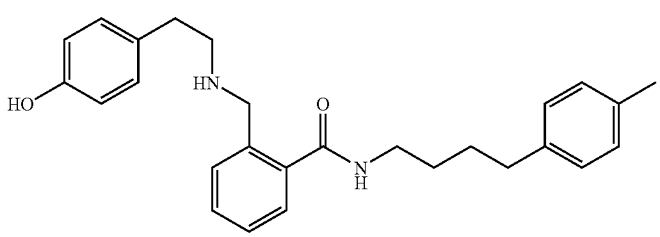 | Procedure C 0.20 g | 21 mg | 417 |
| 239 | 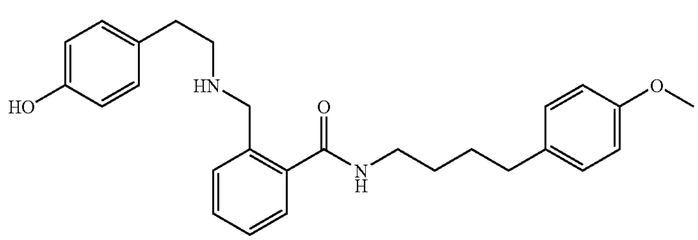 | Procedure C 0.20 g | 20 mg | 433 |
| 146 | 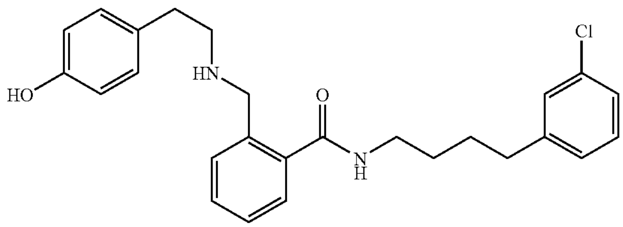 | Procedure C 0.20 g | 9 mg | 437 |

TABLE 1-continued
| Entry | Structure | Cleavage Procedure (Resin Cleaved in g) | Yield (mg) | m/z (M + H)+ |
|---|---|---|---|---|
| 147 | 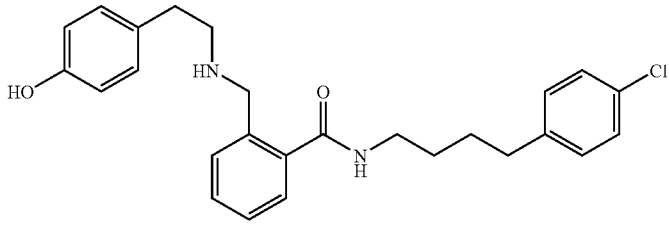 | Procedure C 0.20 g | 21 mg | 437 |
| 240 | 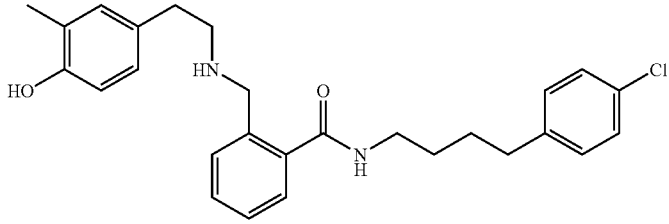 | Procedure C,E 0.40 g | 23 mg | 451 |
| 241 | 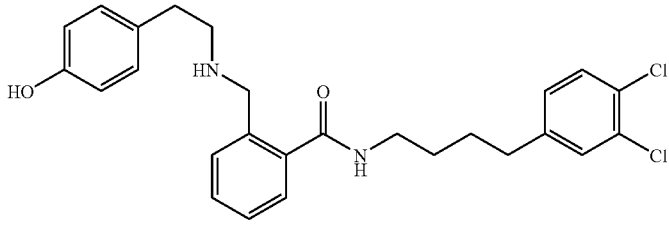 | Procedure C 0.20 g | 7.0 mg | 471 |
| 242 | 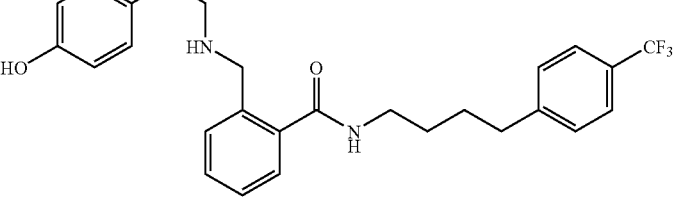 | Procedure C 0.20 g | 11 mg | 471 |
| 243 | 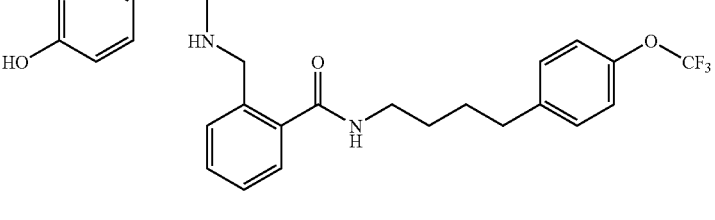 | Procedure C 0.15 g | 9 mg | 487 |
| 244 | 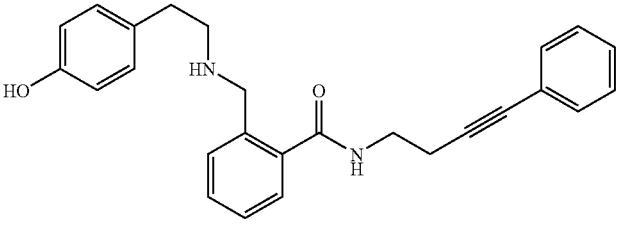 | Procedure C 0.10 g | 14 mg | 399 |

TABLE 1-continued

| Entry | Structure | Cleavage Procedure (Resin Cleaved in g) | Yield (mg) | m/z (M + H)+ |
|---|---|---|---|---|
| 245 | 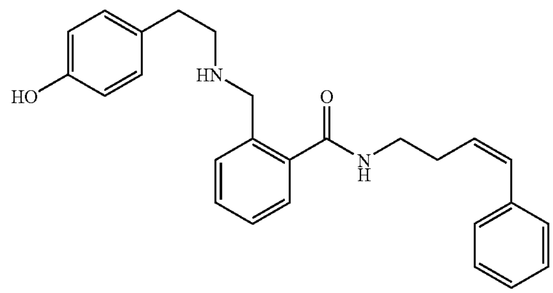 | Procedure C 0.10 g | 13 mg | 401 |
| 246 | 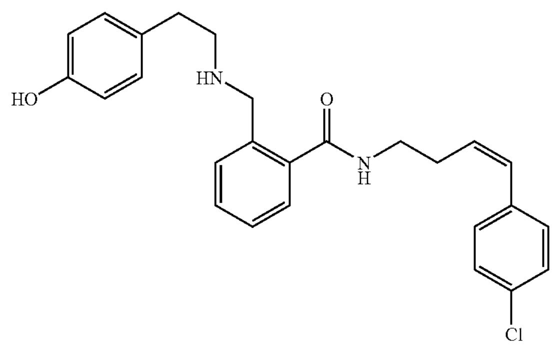 | Procedure C 0.30 g | 38 mg | 435 |
| 148 | 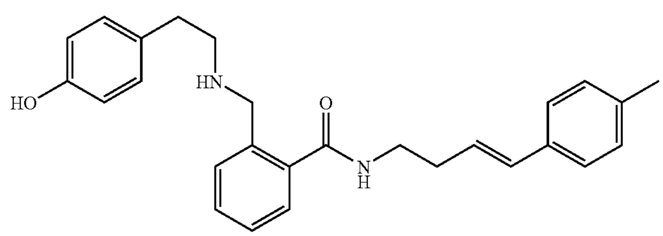 | Procedure C 0.20 g | 10 mg | 415 |
| 149 | 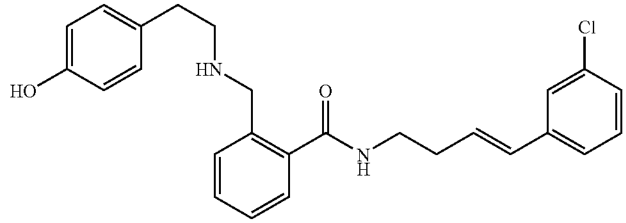 | Procedure C 0.25 g | 14 mg | 435 |
| 447 | 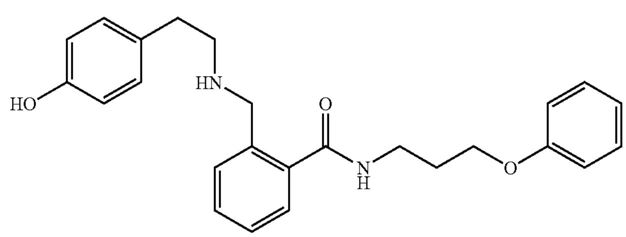 | Procedure C 0.05 g | 8.0 mg | 405 |

TABLE 1-continued

| Entry | Structure | Cleavage Procedure (Resin Cleaved in g) | Yield (mg) | m/z (M + H)+ |
|---|---|---|---|---|
| 247 | 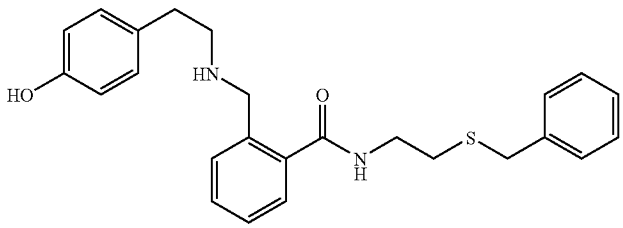 | Procedure C 0.07 g | 7.0 mg | 422 |
| 150 | 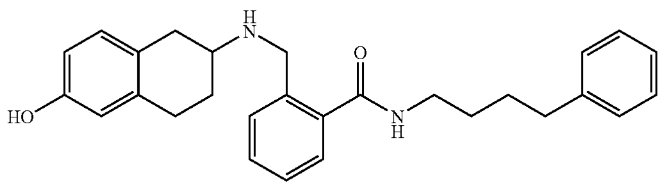 | Procedure C 0.20 g | 9.0 mg | 429 |
| 151 | 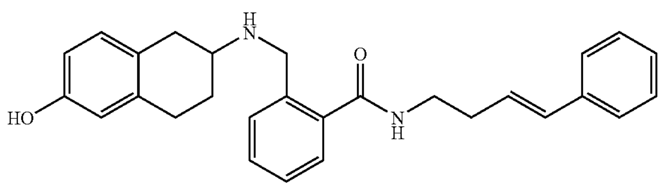 | Procedure C 0.13 g | 4.3 mg | 427 |
| 248 | 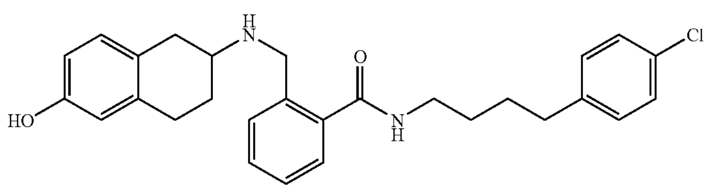 | Procedure C 0.20 g | 13 mg | 463 |
| 448 | 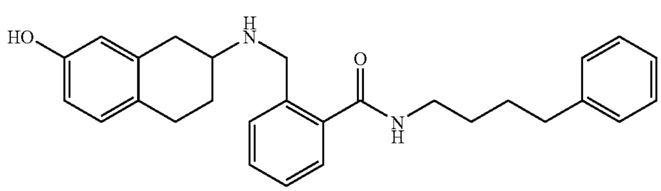 | Procedure C 0.20 g | 22 mg | 429 |
| 449 | 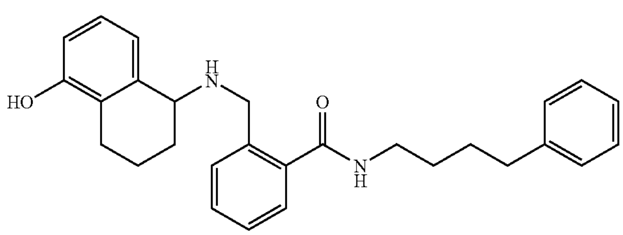 | Procedure C 0.10 g | 19 mg | 429 |
| 450 | 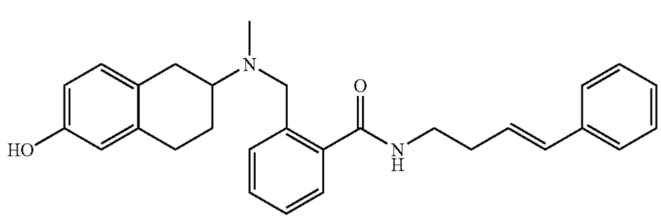 | Procedure C 0.13 g | 8.5 mg | 441 |

TABLE 1-continued

| Entry | Structure | Cleavage Procedure (Resin Cleaved in g) | Yield (mg) | m/z (M + H)+ |
|---|---|---|---|---|
| 249 | 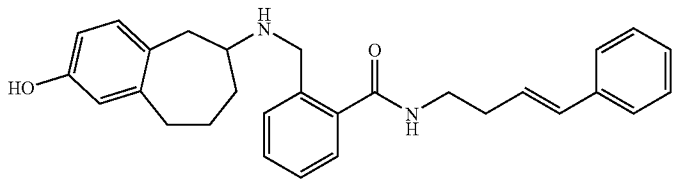 | Procedure C 0.13 g | 3.7 mg | 441 |
| 250 | 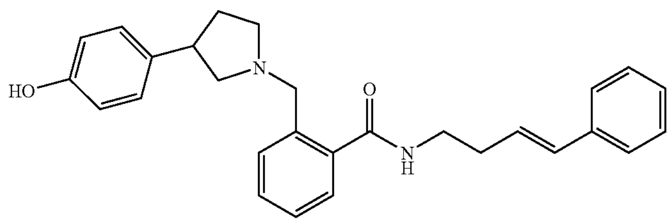 | Procedure C 0.13 g | 14 mg | 427 |
| 152 | 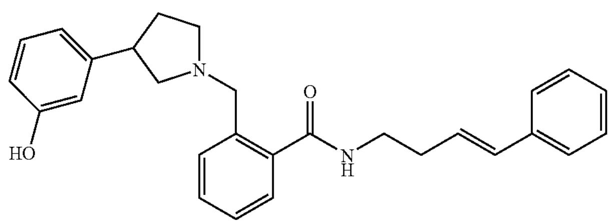 | Procedure C 0.20 g | 13 mg | 427 |
| 451 | 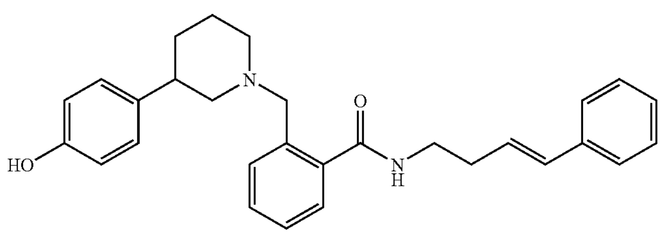 | Procedure C 0.20 g | 10 mg | 441 |
| 251 | 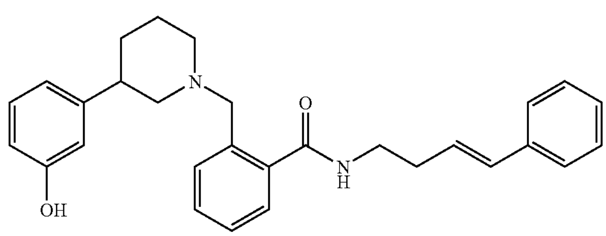 | Procedure C 0.10 g | 45 mg | 441 |
| 153 | 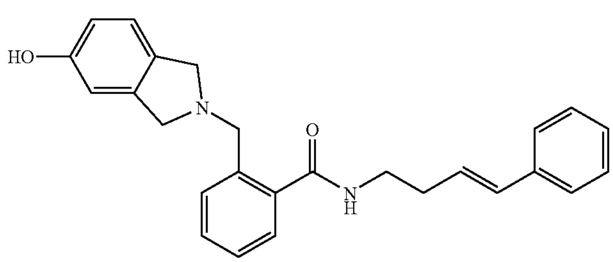 | Procedure C 0.15 g | 16 mg | 399 |

TABLE 1-continued

| Entry | Structure | Cleavage Procedure (Resin Cleaved in g) | Yield (mg) | m/z (M + H)+ |
|---|---|---|---|---|
| 154 | 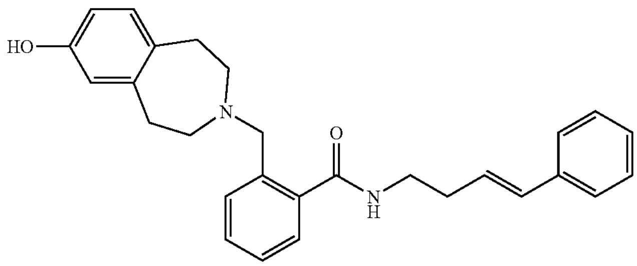 | Procedure C 0.15 g | 11 mg | 427 |
| 452 | 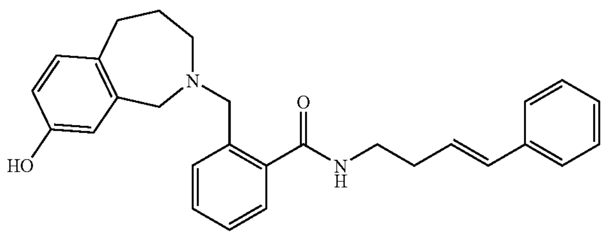 | Procedure C 0.21 g | 5.2 mg | 427 |
| 252 | 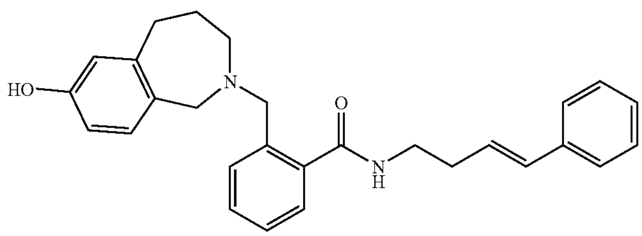 | Procedure C 0.24 g | 6.9 mg | 427 |
| 253 | 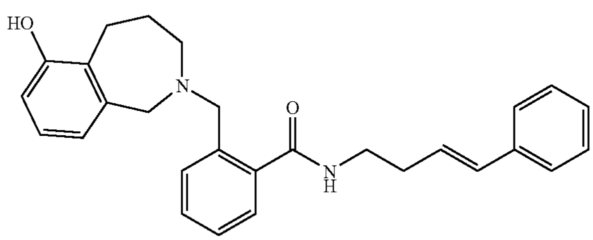 | Procedure C 0.24 g | 4.5 mg | 427 |
| 155 | 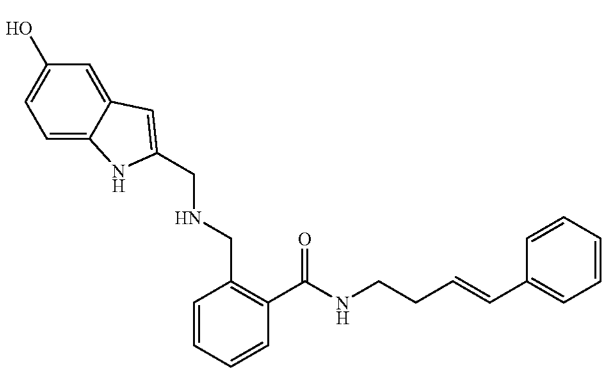 | Procedure D 0.25 g | 6.0 mg | 426 |

Table 2 illustrates several examples of compounds represented by Formula I. These compounds were synthesized using Procedure B and cleaved from the resin by cleavage Procedure C or D. The molecular weight of the compounds was confirmed by mass spectroscopy (m/z)

TABLE 2

| Entry | Structure | Cleavage Procedures (Resin Cleaved in g) | Yield (mg) | m/z (M + H)+ |
| --- | --- | --- | --- | --- |
| 453 | 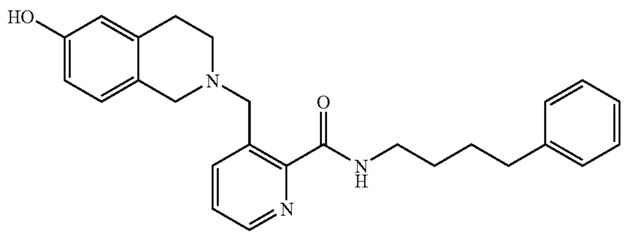 | Procedure C 0.40 g | 11 mg | 416 |
| 454 | 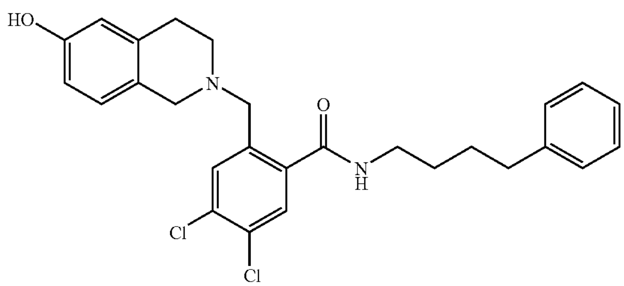 | Procedure C 0.25 g | 4.0 mg | 483/485 |
| 254 |  and  | Procedure C 0.25 mg | 6.0 mg | 433 |
| 316 |  and | Procedure C 0.25 g | 6.0 mg | 429 |

TABLE 2-continued
| Entry | Structure | Cleavage Procedures (Resin Cleaved in g) | Yield (mg) | m/z (M + H)+ |
|-------|-----------|------------------------------------------|------------|--------------|
| | 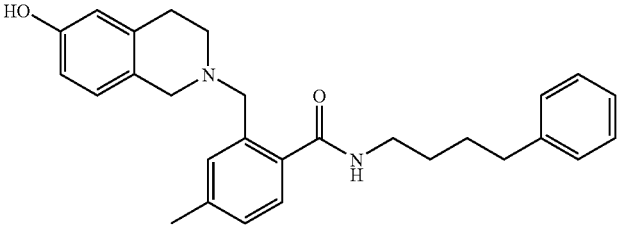 | | | |
| 156 | 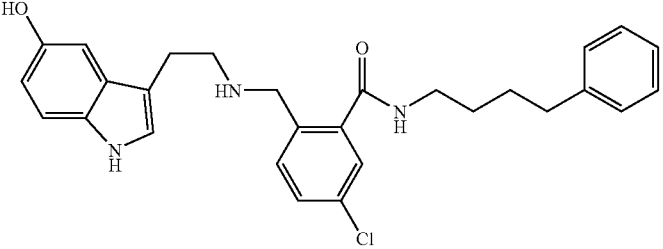 and 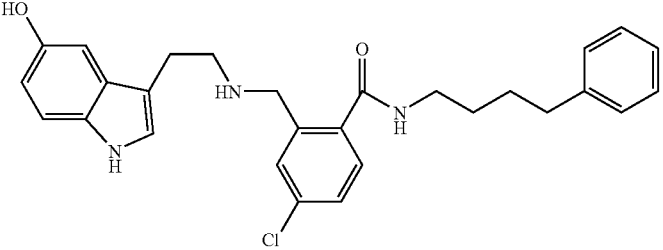 | Procedure C 0.6 g | 11 mg | 476 |
| 455 | 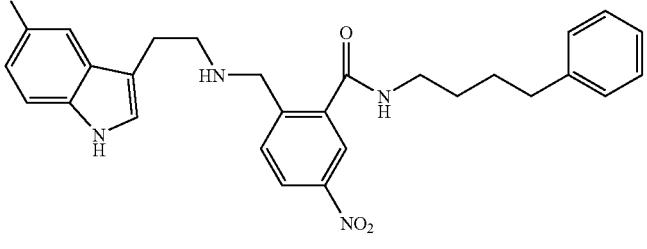 and 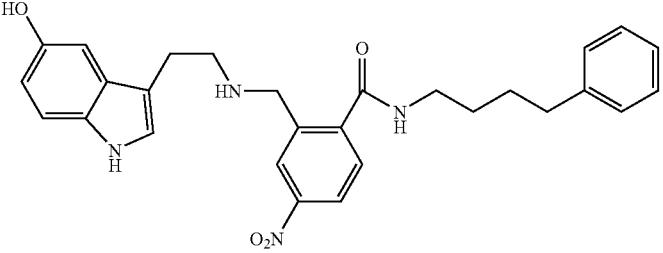 | Procedure C 0.3 g | 2.0 mg | 487 |

TABLE 2-continued

| Entry | Structure | Cleavage Procedures (Resin Cleaved in g) | Yield (mg) | m/z (M + H)+ |
|---|---|---|---|---|
| 456 | 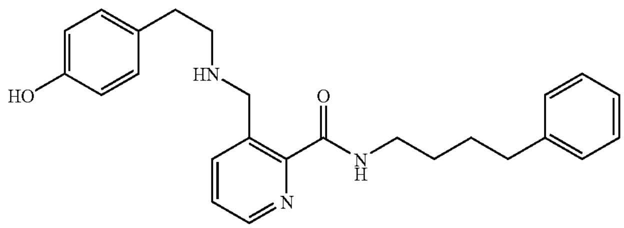 | Procedure C 0.25 g | 2.0 mg | 404 |
| 457 | (two structures shown, "and" between them) | Procedure C 0.20 g | 4.6 mg | 417 |
| 317 | (two structures shown, "and" between them) | Procedure C 0.30 g | 26 mg | 437 |

TABLE 2-continued

| Entry | Structure | Cleavage Procedures (Resin Cleaved in g) | Yield (mg) | m/z (M + H)+ |
|---|---|---|---|---|
| 458 | | Procedure C 0.12 g | 1.8 mg | 448 | and

| 255 | | Procedure C 0.20 g | 13 mg | 421 | and

The activity of the compounds in the in vitro screen was confirmed in vivo. Compound 103 was dissolved in saline and administrated to male mice (strain ICR) at 10 mg/kg i.v. in the tail vein. After 15 minutes, a 3% solution of formalin was administered sub-plantar and the time spent licking the paw was monitored in 5 minute segments over a 45 minute period. The experiment was conducted on 1–6 mice per group and compared to a control set (5 mice), which were given the vehicle alone prior to formalin injection. The first phase response was reduced by approximately 50%. The person of skill in the art would accept this test as predictive of therapeutic utility for analgesia.

Some of the compounds described herein contain one or more asymmetric centers and may thus give rise to enantiomers, diastereomers, and other stereoisometric forms which may be defined in terms of absolute stereochemistry as (R)- or (S)-. The present invention is meant to include all such possible diastereomers as well as their racemic and optically pure forms. Optically active (R)- and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The present invention includes compounds of formula (I) in the form of salts. Suitable salts include those formed with both organic and inorganic acids. Such salts will normally be pharmaceutically acceptable, although non-pharmaceutically acceptable salts may be of utility in the preparation and purification of the compound in question. The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

While it may be possible for the compounds of formula (I) or their salts and solvates to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers, such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, or an appropriate fraction thereof, of the active ingredient.

The pharmaceutical compositions will usually include a "pharmaceutically acceptable inert carrier" and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or nonaqueous techniques. "Pharmaceutically acceptable carrier" also encompasses controlled release means. Compositions of the present invention may also optionally include other therapeutic ingredients, anti-caking agents, preservatives, sweetening agents, colorants, flavors, desiccants, plasticizers, dyes, and the like.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

The invention claimed is:

1. A compound of formula

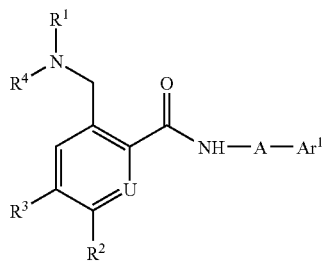

wherein
U is chosen from CH, N and CR$^5$;
A is chosen from the group consisting of (C$_4$ to C$_6$)alkane; (C$_2$ to C$_6$)fluoroalkane; (C$_2$ to C$_6$)alkene; (C$_2$ to C$_6$)alkyne; (C$_2$ to C$_6$)oxaalkane and (C$_2$ to C$_6$)thiaalkane;
Ar$^1$ is chosen from the group consisting of aryl, heteroaryl, substituted aryl and substituted heteroaryl;
R$^2$, R$^3$ and R$^5$ are independently chosen from —H, loweralkyl, fluoroloweralkyl, halo, loweralkoxy, fluoroloweralkoxy and NO$_2$; and
R$^1$ and R$^4$, together with the nitrogen to which they are attached, form a pyridoindole or substituted pyridoindole.

2. A compound according to claim 1 wherein U is N and R$^2$ and R$^3$ are H.

3. A compound according to claim 1 wherein U is CH.

4. A compound according to claim 3 wherein A is chosen from the group consisting of (C$_4$ to C$_6$)alkane; (C$_3$ to C$_5$)alkene; (C$_3$ to C$_5$)alkyne; (C$_3$ to C$_5$)oxaalkane and (C$_3$ to C$_5$)thiaalkane.

5. A compound according to claim 3 wherein A is chosen from the group consisting of —CH$_2$CH$_2$CH═CH—; —(CH$_2$)$_5$—; —(CH$_2$)$_4$—; —CH$_2$CH$_2$C(CH$_3$)═CH—; —CH$_2$CH$_2$C(CF$_3$)═CH—; —CH$_2$CH$_2$OCH$_2$—; —CH$_2$CH$_2$CH≡CH—; —(CH$_2$)$_3$O—; —CH$_2$CH$_2$SCH$_2$—; and

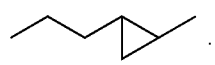

6. A compound according to claim 5 wherein A is (C$_4$ to C$_5$)alkane or (C$_3$ to C$_5$)alkene.

7. A compound according to claim 1 wherein Ar$^1$ is chosen from the group consisting of phenyl, halophenyl, dihalophenyl, methoxyphenyl, trifluoromethoxyphenyl, trifluoromethylphenyl, loweralkylphenyl, hydroxyphenyl, and pyridinyl.

8. A compound according to claim 1–7 wherein R$^1$ and R$^4$, together with the nitrogen to which they are attached form a residue of the formula chosen from the group consisting of:

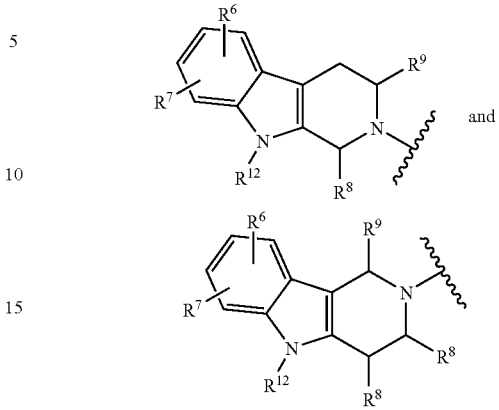

wherein
R$^6$ is chosen from the group consisting of hydrogen, hydroxy, loweralkyl, fluoroloweralkyl, loweralkoxyl, fluoroloweralkoxyl and halo;
R$^7$ is chosen from the group consisting of —R$^{16}$, —OR$^{16}$, —NH$_2$, NO$_2$, —CN, —NH(CO)NHR$^{17}$, —CONH$_2$, —NH(CO)CH$_3$, —SO$_2$NHR$^{17}$, -halo, —CH$_2$OH, —COOR$^{17}$, —NH(SO$_2$)CH$_3$, and —NH(CO)H;
R$^8$ and R$^9$ are independently chosen from the group consisting of —R$^{16}$, —CH$_2$OH, and —COOR$^{17}$;
R$^{16}$ is chosen from the group consisting of hydrogen, loweralkyl and fluoroloweralkyl; and
R$^{12}$ and R$^{17}$ are independently chosen from the group consisting of hydrogen and loweralkyl.

9. A compound according to claim 8 wherein
R$^6$ is hydrogen or hydroxy;
R$^7$ is hydrogen;
R$^8$ is hydrogen or methyl; and
R$^9$ is hydrogen, methyl or —CH$_2$OH.

10. A compound according to claim 9 wherein R$^2$ and R$^3$ are hydrogen.

11. A pharmaceutical composition comprising a pharmaceutically acceptable carrier and a compound according to claim 1.

12. A pharmaceutical composition comprising a pharmaceutically acceptable carrier and a compound according to claim 9.

13. A method for treating pain comprising administering to a mammal in need of such treatment a therapeutically effective amount of a compound according to claim 1.

14. A method for treating pain comprising administering to a mammal in need of such treatment a therapeutically effective amount of a compound according to claim 9.

* * * * *

UNITED STATES PATENT AND TRADEMARK OFFICE
CERTIFICATE OF CORRECTION

PATENT NO. : 7,084,154 B2 Page 1 of 1
APPLICATION NO. : 10/364039
DATED : August 1, 2006
INVENTOR(S) : Ho et al.

It is certified that error appears in the above-identified patent and that said Letters Patent is hereby corrected as shown below:

Title page:
(75) Inventors:
Delete "Koc-Kan Ho, West Windsor, NJ (US);" and insert --Koc-Kan Ho, Monmouth Junction, NJ (US);--

Claim 8
Col. 137, line 56, delete the word "claim" and insert the word --claims--

Column 138, lines 1 thru 19 – Second Structure:

Delete current structure and replace with structure below

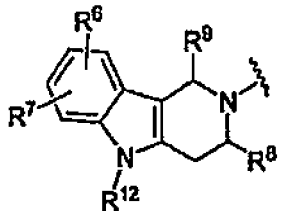

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,084,154 B2  Page 1 of 1
APPLICATION NO. : 10/364039
DATED : August 1, 2006
INVENTOR(S) : Ho et al.

It is certified that error appears in the above-identified patent and that said Letters Patent is hereby corrected as shown below:

Title page:
(75) Inventors:
Delete "Koc-Kan Ho, West Windsor, NJ (US);" and insert --Koc-Kan Ho, Monmouth Junction, NJ (US);--

Claim 8
Col. 137, line 56, delete the word "claim" and insert the word --claims--
line 56, insert --any of -- after the word "to".

Column 138, lines 1 thru 19 – Second Structure:

Delete current structure and replace with structure below

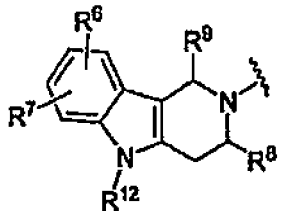

This certificate supersedes Certificate of Correction issued November 28, 2006.

Signed and Sealed this

Tenth Day of April, 2007

JON W. DUDAS
*Director of the United States Patent and Trademark Office*